United States Patent
Johansson et al.

(10) Patent No.: US 7,410,966 B2
(45) Date of Patent: Aug. 12, 2008

(54) USE OF AND SOME NOVEL IMIDAZOPYRIDINES

(75) Inventors: Henrik Johansson, Lund (SE); Karolina Lawitz, Lund (SE); Grigorios Nikitidis, Lund (SE); Peter Sjö, Lund (SE); Peter Storm, Lund (SE)

(73) Assignee: AstraZeneca AB, Södertälje (SE)

( * ) Notice: Subject to any disclaimer, the term of this patent is extended or adjusted under 35 U.S.C. 154(b) by 483 days.

(21) Appl. No.: 10/524,204

(22) PCT Filed: Aug. 13, 2003

(86) PCT No.: PCT/SE03/01279

§ 371 (c)(1),
(2), (4) Date: Feb. 10, 2005

(87) PCT Pub. No.: WO2004/016611

PCT Pub. Date: Feb. 26, 2004

(65) Prior Publication Data

US 2005/0261333 A1 Nov. 24, 2005

(30) Foreign Application Priority Data

Aug. 14, 2002 (SE) ........................ 020462

(51) Int. Cl.
*C07D 413/00* (2006.01)
*C07D 471/02* (2006.01)
*C07D 491/02* (2006.01)
*C07D 498/02* (2006.01)
*A61K 31/535* (2006.01)
*A61K 31/44* (2006.01)
*A01N 43/42* (2006.01)

(52) U.S. Cl. .................. 514/234.5; 514/303; 546/118; 544/117

(58) Field of Classification Search .................. 546/118; 514/303, 234.5; 544/117
See application file for complete search history.

(56) References Cited

U.S. PATENT DOCUMENTS 3,985,891 A 10/1976 Kutter et al.

FOREIGN PATENT DOCUMENTS

| EP | 0 049 407 | 4/1982 |
|----|-----------|--------|
| WO | WO 01/96336 | 12/2001 |
| WO | 02/48152 | * 6/2002 |

OTHER PUBLICATIONS

Dubey et al., Indian Journal of Chemistry, Section B: Organic chemistry including medicinal chemistry, 2001, vol. 40B, pp. 361-367.*

* cited by examiner

*Primary Examiner*—D. Margaret Seaman
*Assistant Examiner*—Niloofar Rahmani

(57) ABSTRACT

The use of compounds of formula (I) wherein $R^1$, $R^3$, $R^{10}$, m and Ar are as defined in the Specification and pharmaceutically acceptable salts thereof in the manufacture of a medicament for the treatment or prophylaxis of diseases or conditions in which inhibition of kinase Itk activity is beneficial is disclosed. Certain novel compounds of formula (I), together with processes for their preparation, compositions containing them and their use in therapy are also disclosed

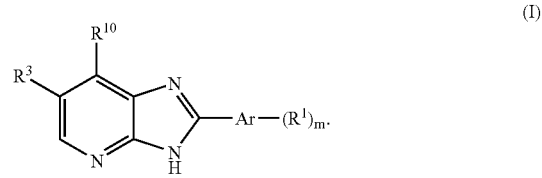

4 Claims, No Drawings

USE OF AND SOME NOVEL IMIDAZOPYRIDINES

CROSS-REFERENCE TO RELATED APPLICATIONS

This application is the national phase application under 35 U.S.C. § 371 of PCT International Application No. PCT/SE2003/001279, filed Aug. 13, 2003, which claims priority to Swedish Application Serial No. 0202462-8, filed Aug. 14, 2002.

FIELD OF THE INVENTION

This invention relates to the use of imidazopyridine derivatives as inhibitors of the kinase Itk. Certain novel imidazopyridine derivatives are also disclosed together with processes for their preparation, pharmaceutical compositions comprising them, and their use in therapy.

BACKGROUND OF THE INVENTION

Inducible T cell Kinase (Itk) is a member of the Tec-family of cytosolic protein tyrosine kinases. In mammalians, this family also includes Btk, Tec, Bmx, and Txk. These kinases regulate various immune cell functions that integrate signals given by the other cytosolic tyrosine kinases as well as serine/threonine kinases, lipid kinases, and small G proteins. Tec-family kinases have the following general structure: a N-terminal pleckstrin-homology (PH) domain, a Tec-homology domain that includes a Btk motif and one or two proline-rich (PR) motifs, a SH3 domain, a SH2 domain and a c-terminal catalytic (SH1) domain. These kinases are expressed exclusively in hematopoietic tissues, with the exception of Tec and Bmx that have also been detected in endothelial cells. The cellular distribution is different for the Tec-family members. For example, Itk is expressed by T cells, NK cells and mast cells, whereas Btk is expressed by all hematopoietic cells except T cells. Thus, hematopoietic cells may express one or several Tec-family kinases. For example, T cells express Itk, Tec and Txk, and mast cells express Btk, Itk and Tec. Btk is by far the most extensively studied among the Tec-family kinases, due to its association with X-linked agammaglobulinemia (XLA), and Btk is currently the only Tec-family kinase with a known human phenotype. XLA patients are virtually devoid of mature B cells and their Ig levels are strongly reduced. Itk$^{-/-}$ mice show defects in T cell activation and differentiation. T helper 2 (Th2) differentiation is disrupted in these mice, whereas Th1 differentiation is apparently intact. In T and B cells, signalling through T cell receptors and B cell receptors leads to activation of Itk and Btk, respectively. Downstream of Itk and Btk a number of different messengers are engaged; scaffolding proteins (SLP-76, LAT, SLP-65), Src kinases, MAP kinases, and PI3-K. These events are followed by PLC-γ activation that leads to IP3 generation and sustained Ca$^{2+}$ flux, and subsequently activation of transcription factors. PLC-γ1 has been suggested as a direct substrate for Itk. In T cells, Itk (and Tec) may also mediate signalling through the CD28 co-receptor. Furthermore, Itk has in T cells been implicated in the activation of β-integrin. Signalling from Tec-family kinases can also be regulated by PH domain-mediated plasma membrane localization, and by Src-family-mediated phosphorylation of critical tyrosine residues. Interestingly, Itk, Btk and Txk have recently been shown to translocate to the nucleus after activation.

From studies using Itk–/– mice, it has been proposed that Itk is required for Th2 but not Th1 cell development. This was demonstrated in the *N. brasiliensis* and *L. major* infection models where the Itk–/– animals are protected in the *Leishmania* model indicating an intact Th1 response, whereas they are susceptible to infection with *N. Brasiliensis* that requires an intact Th2 response for resolution of the infection. This indicates that modulation of Itk activity may prove useful for treatment of Th2-driven disorders and conditions.

We have identified the critical role of Itk in regulating important mast cell and basophil functions and established that the activity of mast cells or basophils may be inhibited through inhibition of Itk. Thus Itk inhibitors may be used as pharmaceutical agents for the treatment of mast cell-driven or basophil-driven conditions or diseases. In particular, we have identified Itk as a target for inhibiting several key events in both acute and late phase allergic reactions common to allergic rhinitis and asthma.

EP 209 707 discloses particular fused imidazo derivatives, including some imidazopyridines, and their use as potential cardiovascular agents.

DE 2 305 339 and U.S. Pat. No. 3,985,891 disclose certain imidazopyridine derivatives potentially useful as cardiotonics, anticoagulants and as agents for altering blood pressure.

WO 01/96336 discloses certain imidazopyridine derivatives that are useful as inhibitors of the enzyme 15-lipoxygenase.

None of the above publications are concerned with compounds that have utility as inhibitors of the kinase Itk.

The present invention discloses 2-aryl-substituted derivatives of 6-substituted-3H-imidazo[4,5-b]pyridines that are useful as Itk inhibitors.

DISCLOSURE OF THE INVENTION

The present invention provides the use of a compound of formula (I)

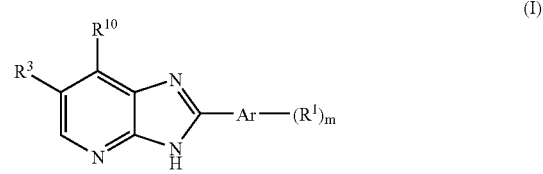

wherein:

$R^3$ represents halogen, CN, C1 to 3 alkyl or C1 to 3 alkoxy;

Ar represents phenyl, a 5- or 6-membered heteroaromatic ring or an indole ring; said heteroaromatic ring incorporating 1 to 3 heteroatoms independently selected from O, N and S;

$R^1$ represents H, halogen, CN, C1 to 6 alkyl, $NO_2$, $SO_2Me$, C1 to 6 alkynyl, $CH_2OH$, $OR^2$, $(CH_2)_nNR^4R^5$ or phenyl optionally substituted by $NH_2$;

m represents an integer 1 or 2; and when m represents 2, each $R^1$ may be selected independently;

n represents an integer 0 or 1;

$R^2$ represents H or C1 to 4 alkyl; said C1 to 4 alkyl being optionally further substituted by a group selected from $Ar^1$, $CONH_2$, $CO_2Et$, OH, $NR^6R^7$ halogen and epoxy; and when substituted by $NR^6R^7$ or halogen, said alkyl is optionally further substituted by OH;

$R^4$ represents H, C1 to 4 alkyl or $CH_2Ar^2$;

$R^5$ represents H, C1 to 6 alkyl, C2 to 6 alkanoyl, $SO_2$—$Ar^5$ or $CH_2Ar^2$; said alkyl group being optionally further substituted by a 5 to 7 membered saturated azacyclic ring optionally incorporating one additional heteroatom selected from O, S and $NR^8$;

or the group —$NR^4R^5$ together represents a 5 to 7 membered saturated azacyclic ring optionally incorporating one additional heteroatom selected from O, S and $NR^8$;

$R^6$ represents H, C1 to 4 alkyl or $CH_2CH_2OCH_3$;

$R^7$ represents H, C1 to 6 alkyl, C3 to 6 cycloalkyl, $Ar^3$, a 5 or 6 membered saturated or partially unsaturated heterocyclic ring incorporating 1 or 2 heteroatoms selected independently from O, N and S and optionally substituted by Me, Et or $CO_2Et$; said C1 to 6 alkyl being optionally substituted by one or more groups selected independently from OH, CN, $CONMe_2$, CONHMe, C1 to 4 alkoxy, halogen, $NMe_2$, $Ar^4$, and a 5 or 6 membered saturated heterocyclic ring incorporating 1 or 2 heteroatoms selected independently from O, N and S and optionally also incorporating a carbonyl group; said C3 to 6 cycloalkyl being optionally substituted by OH or CN;

or the group —$NR^6R^7$ together represents a 5 to 7 membered saturated azacyclic ring optionally incorporating 1 additional heteroatom selected from O and $NR^9$; and optionally substituted by one or more substituents selected independently from OH, $NMe_2$, $CONH_2$, $CH_2OH$, $CH_2CH_2OH$, phenyl, pyridyl, piperidinyl or methoxyphenyl;

$R^8$ represents H, C1 to 6 alkyl or $CH_2Ph$;

$R^9$ represents $CH_2CH_2OH$, $COCH_3$, Me, $CO_2Et$, $CH_2CH_2OMe$ or a six membered aromatic or azaaromatic ring optionally further substituted by one or more substituents selected independently from Cl, CN, OMe and $CF_3$;

$R^{10}$ represents H, halogen, CN, C1 to 4 alkyl, C1 to 4 alkoxy, $NR^{14}R^{15}$ or a group —X—Y—Z;

$R^{14}$ and $R^{15}$ independently represent H or C1 to 4 alkyl; said alkyl being optionally further substituted by OH;

X represents O, S, a bond or $NR^{16}$ wherein $R^{16}$ represents H or C1 to 4 alkyl; said alkyl being optionally further substituted by OH;

Y represents C1 to 4 alkyl or a bond;

Z represents:
i) phenyl, naphthyl or a 5- or 6-membered heteroaromatic ring system containing one to three heteroatoms independently selected from O, N and S; or
ii) a five- or six-membered saturated heterocyclic ring containing one or two heteroatoms independently selected from O; N and S; said ring optionally being benzo fused; or
iii) C3 to 6 cycloalkyl;

said ring Z being optionally substituted by one or more substituents independently selected from halogen, OH, C1 to 4 alkyl, C1 to 4 alkoxy, hydroxymethyl, methylsulphonyl and $NR^{17}R^{18}$;

$R^{17}$ and $R^{18}$ independently represent H, C1 to 4 alkyl, formyl or C2 to alkanoyl; or the group $NR^{17}R^{18}$ together represents a saturated 5 to 7 membered azacyclic ring optionally containing one further heteroatom selected from O, N and S;

$Ar^1$ represents phenyl, thiazolyl or thiadiazolyl, optionally further substituted by halogen;

$Ar^2$ represents phenyl, a 5- or 6-membered heteroaromatic ring or a benzimidazole ring; said heteroaromatic ring incorporating 1 to 3 heteroatoms independently selected from O, N and S; said phenyl or heteroaromatic or benzimidazole ring being optionally further substituted by one or two groups independently selected from halogen, C1 to 4 alkyl, CN, $CH_2OH$, C1 to 4 alkoxy, $CO_2Me$, $CH_2OAc$ and pyridyl;

$Ar^3$ represents thiazolyl, triazolyl or tetrazolyl;

$Ar^4$ represents phenyl, a 5- or 6-membered heteroaromatic ring or an indole ring; said heteroaromatic ring incorporating 1 to 3 heteroatoms independently selected from O, N and S; said phenyl, heteroaromatic or indole ring being optionally further substituted by one or two groups independently selected from halogen and OMe;

$Ar^5$ represents phenyl, a 5- or 6-membered heteroaromatic ring or a quinoline ring; said heteroaromatic ring incorporating 1 to 3 heteroatoms independently selected from O, N and S; said phenyl or heteroaromatic or quinoline ring being optionally further substituted by halogen, C1 to 4 alkyl, CN, C1 to 4 alkoxy, and $OCH_2CH_2CN$;

or a pharmaceutically acceptable salt thereof, in the manufacture of a medicament for the treatment or prophylaxis of diseases or conditions in which inhibition of kinase Itk activity is beneficial.

The compounds of formula (I) may exist in enantiomeric forms. All enantiomers, diastereoisomers, racemates and mixtures thereof are included within the scope of the invention.

It will be readily apparent to the man skilled in the art that compounds of general formula (I) may exist in tautomeric forms as illustrated below:

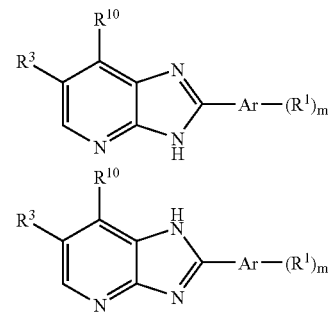

All such tautomeric forms and mixtures thereof are included within the scope of the present invention.

In one embodiment, $R^3$ in formula (I) represents halogen.
In another embodiment, $R^3$ in formula (I) represents bromo.
In another embodiment, $R^3$ in formula (I) represents chloro.
In another embodiment, Ar in formula (I) represents phenyl.
In another embodiment, m is 1 and $R^1$ in formula (I) represents $OR^2$ or $(CH_2)_nNR^4R^5$.
In another embodiment, $R^2$ in formula (I) represents $CH_2CHOHCH_2NR^6R^7$.
In another embodiment, $R^2$ in formula (D) represents $CH_2CH_2NR^6R^7$.
In another embodiment, m is 1 and $R^1$ in formula (I) represents $NR^4 CH_2Ar^2$.
In one embodiment, $R^{10}$ represents H.
In another embodiment, $R^{10}$ represents halogen, CN, C1 to 4 alkyl, C1 to 4 alkoxy, $NR^{14}R^{15}$ or a group —X—Y—Z;

In one aspect, the invention provides the use of a compound of formula (I) wherein $R^3$ represents halogen; Ar represents phenyl; m is 1; $R^1$ represents $OR^2$ or $(CH_2)_nNR^4R^5$; $R^2$ represents C2 to 4 alkyl; said C2 to 4 alkyl being optionally further substituted by $NR^6R^7$ or by both OH and $NR^6R^7$; and $NR^4R^5$ represents $NR^4CH_2Ar^2$; or a pharmaceutically acceptable salt thereof; in the manufacture of a medicament for the treatment or prophylaxis of diseases or conditions in which inhibition of the kinase Itk activity is beneficial.

In one aspect the present invention provides the use of a compound of formula (Ie)

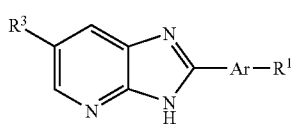

(Ie)

wherein:
R³ represents halogen, C1 to 3 alkyl or C1 to 3 alkoxy;
Ar represents phenyl, a 5- or 6-membered heteroaromatic ring or an indole ring; said heteroaromatic ring incorporating 1 to 3 heteroatoms independently selected from O, N and S; said phenyl, heteroaromatic or indole ring being optionally further substituted by chloro or OMe;
R¹ represents H, halogen, CN, C1 to 6 alkyl, NO₂, SO₂Me, C1 to 6 alkynyl, CH₂OH, phenyl, OR² or (CH₂)ₙNR⁴R⁵;
n represents an integer 0 or 1;
R² represents H or C1 to 4 alkyl; said C1 to 4 alkyl being optionally further substituted by a group selected from Ar¹, CONH₂, CO₂Et, OH, NR⁶R⁷, halogen and epoxy; and when substituted by NR⁶R⁷ or halogen, said alkyl is optionally further substituted by OH;
R⁴ represents H or C1 to 4 alkyl;
R⁵ represents H, C1 to 6 alkyl, C2 to 6 alkanoyl or CH₂Ar²;
or the group —NR⁴R⁵ together represents a 5 to 7 membered saturated azacyclic ring optionally incorporating one additional heteroatom selected from O, S and NR⁸;
R⁶ represents H, C1 to 4 alkyl or CH₂CH₂OCH₃;
R⁷ represents H, C1 to 6 alkyl, C3 to 6 cycloalkyl, Ar³, a 5 or 6 membered saturated or partially unsaturated heterocyclic ring incorporating 1 or 2 heteroatoms selected independently from O, N and S and optionally substituted by Me, Et or CO₂Et; said C1 to 6 alkyl being optionally substituted by one or more groups selected independently from OH, CN, CONMe₂, CONHMe, C1 to 4 alkoxy, halogen, NMe₂, Ar⁴, and a 5 or 6 membered saturated heterocyclic ring incorporating 1 or 2 heteroatoms selected independently from O, N and S and optionally also incorporating a carbonyl group; said C3 to 6 cycloalkyl being optionally substituted by OH or CN;
or the group —NR⁶R⁷ together represents a 5 to 7 membered saturated azacyclic ring optionally incorporating 1 additional heteroatom selected from O and NR⁹; and optionally substituted by one or more substituents selected independently from OH, NMe₂, CONH₂, CH₂OH, CH₂CH₂OH, phenyl, pyridyl, piperidinyl or methoxyphenyl;
R⁸ represents H, C1 to 6 alkyl or CH₂Ph;
R⁹ represents CH₂CH₂OH, COCH₃, Me, CO₂Et, CH₂CH₂OMe or a six membered aromatic or azaaromatic ring optionally further substituted by one or more substituents selected independently from Cl, CN, OMe and CF₃;
Ar¹ represents phenyl, thiazolyl or thiadiazolyl, optionally further substituted by halogen;
Ar² represents phenyl, a 5- or 6-membered heteroaromatic ring or a benzimidazole ring; said heteroaromatic ring incorporating 1 to 3 heteroatoms independently selected from O, N and S; said phenyl or heteroaromatic or benzimidazole ring being optionally further substituted by one or two groups independently selected from halogen, C1 to 4 alkyl, CN, CH₂OH, C1 to 4 alkoxy, CO₂Me, CH₂OAc and pyridyl;
Ar³ represents thiazolyl, triazolyl or tetrazolyl;

Ar⁴ represents phenyl, a 5- or 6-membered heteroaromatic ring or an indole ring; said heteroaromatic ring incorporating 1 to 3 heteroatoms independently selected from O, N and S; said phenyl, heteroaromatic or indole ring being optionally further substituted by one or two groups independently selected from halogen and OMe;

or a pharmaceutically acceptable salt thereof, in the manufacture of a medicament for the treatment or prophylaxis of diseases or conditions in which inhibition of kinase Itk activity is beneficial.

Unless otherwise indicated, the term "C1 to 6 alkyl" referred to herein denotes a straight or branched chain alkyl group having from 1 to 6 carbon atoms. Examples of such groups include methyl, ethyl, n-propyl, i-propyl, n-butyl, i-butyl, t-butyl, pentyl and hexyl. The terms C1 to 4 alkyl, C1 to 3 alkyl and C2 to 4 alkyl are to be interpreted analogously.

Unless otherwise indicated, the term "C1 to 6 alkynyl" referred to herein denotes a straight or branched chain alkyl group having from 1 to 6 carbon atoms and including at least one carbon-carbon triple bond. Examples of such groups include ethynyl, propynyl and butynyl.

Unless otherwise indicated, the term "C3 to 6 cycloalkyl" referred to herein denotes a saturated carbocyclic ring having from 3 to 6 carbon atoms. Examples of such groups include cyclopropyl, cyclopentyl and cyclohexyl.

Unless otherwise indicated, the term "C2 to 6 alkanoyl" referred to herein denotes a straight or branched chain alkyl group having from 1 to 5 carbon atoms bonded to the remainder of the molecule via a carbonyl group. Examples of such groups include acetyl, propionyl and butyryl.

Unless otherwise indicated, the term "C1 to 4 alkoxy" referred to herein denotes an oxygen substituent bonded to a straight or branched chain alkyl group having from 1 to 4 carbon atoms. Examples of such groups include methoxy, ethoxy, n-propoxy, i-propoxy, n-butoxy, i-butoxy and s-butoxy. The term "C1 to 3 alkoxy" referred to herein is to be interpreted analogously.

Unless otherwise indicated, the term "halogen" referred to herein denotes fluorine, chlorine, bromine and iodine.

Examples of a 5- or 6-membered heteroaromatic ring incorporating 1 to 3 heteroatoms independently selected from O, N and S, include pyridyl, thienyl, furyl, pyrrolyl, imidazolyl, triazolyl, thiadiazolyl, pyrazolyl, pyrazinyl, thiazolyl and isoxazolyl.

Examples of a 5 to 7 membered saturated azacyclic ring optionally incorporating one additional heteroatom selected from O, S and N include pyrrolidine, piperidine, piperazine, morpholine and thiomorpholine.

Examples of a 5 or 6 membered saturated or partially unsaturated heterocyclic ring incorporating 1 or 2 heteroatoms selected independently from O, S and N include tetrahydrofuran, tetrahydropyran, pyrrolidine, pyrroline, piperidine, piperazine and morpholine.

Examples of a 5 or 6 membered saturated heterocyclic ring incorporating 1 or 2 heteroatoms selected independently from O, S and N and optionally also incorporating a carbonyl group include tetrahydrofuran, tetrahydropyran, tetrahydropyranone, pyrrolidine, pyrrolidinone, piperidine, piperidinone, piperazine and morpholine.

Examples of a 6 membered aromatic or azaaromatic ring include phenyl, pyridyl, pyrazinyl and pyrimidinyl.

The use of each of the compounds of formula (I) that are specifically exemplified within the Examples section of the present specification, either as such, or as the corresponding free bases, or as pharmaceutically acceptable salts thereof, is specifically included within the present invention:

A more particular aspect of the invention provides the use of a compound of formula (I), or a pharmaceutically acceptable salt thereof, in the manufacture of a medicament for the treatment or prophylaxis of allergic, autoimmune, inflammatory, proliferative and hyperproliferative diseases and immune-mediated diseases including rejection of transplanted organs or tissues and Acquired Immunodeficiency Syndrome (AIDS).

According to the invention there is also provided a method of treating, or reducing the risk of, diseases or conditions in which inhibition of kinase Itk activity is beneficial, which comprises administering to a person suffering from or at risk of said disease or condition, a therapeutically effective amount of a compound of formula (I) or a pharmaceutically acceptable salt thereof.

More particularly, there is also provided a method of treating, or reducing the risk of allergic, autoimmune, inflammatory, proliferative and hyperproliferative diseases and immune-mediated diseases including rejection of transplanted organs or tissues and Acquired Immunodeficiency Syndrome (AIDS), which comprises administering to a person suffering from or at risk of said disease or condition, a therapeutically effective amount of a compound of formula (I) or a pharmaceutically acceptable salt thereof.

Examples of these conditions are:

(1) (the respiratory tract) airways diseases including chronic obstructive pulmonary disease (COPD) such as irreversible COPD; asthma, such as bronchial, allergic, intrinsic, extrinsic and dust asthma, particularly chronic or inveterate asthma (for example, late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia; sinusitis, chronic rhinosinusitis, nasosinusal polyposis; pulmonary fibrosis;

(2) (bone and joints) rheumatoid arthritis, seronegative spondyloarthropathies (including ankylosing spondylitis, psoriatic arthritis and Reiter's disease), Behcet's disease, Sjogren's syndrome and systemic sclerosis;

(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia areata and vernal conjunctivitis;

(4) (gastrointestinal tract) Coeliac disease, proctitis, eosinopilic gastro-enteritis, mastocytosis, Crohn's disease, ulcerative colitis, food-related allergies which have effects remote from the gut, for example, migraine, rhinitis and eczema;

(5) (other tissues and systemic disease) multiple sclerosis, atherosclerosis, Acquired Immunodeficiency Syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatious leprosy, sezary syndrome and idiopathic thrombocytopenia pupura; tuberculosis;

(6) (allograft rejection) acute and chronic following, for example, transplantation of kidney, heart, liver, lung, bone marrow, skin and cornea; and chronic graft versus host disease.

We are particularly interested in Th2-driven and/or mast cell-driven and/or basophil-driven conditions or diseases.

Thus, a more particular aspect of the invention provides the use of a compound of formula (I) or a pharmaceutically acceptable salt thereof, in the manufacture of a medicament for the treatment or prophylaxis of Th2-driven and/or mast cell-driven and/or basophil driven diseases or conditions; and a method of treating, or reducing the risk of, Th2-driven and/or mast cell-driven and/or basophil driven diseases or conditions which comprises administering to a person suffering from or at risk of, said disease or condition, a therapeutically effective amount of a compound of formula (I) or a pharmaceutically acceptable salt thereof.

In a preferred aspect of the invention, we provide a method for the treatment or prevention of a reversible obstructive airway disease, especially asthma, which comprises administering a therapeutically effective amount of a compound of formula (I) or a pharmaceutically acceptable salt thereof to a human that is suffering from or susceptible to the disease. We also provide the use of a compound of formula (I) or a pharmaceutically acceptable salt thereof in the manufacture of a medicament for the treatment or prevention of a reversible obstructive airway disease, especially asthma.

In another preferred aspect of the invention, we provide a method for the treatment or prevention of rhinitis which comprises administering a therapeutically effective amount of a compound of formula (I) or a pharmaceutically acceptable salt thereof to a human that is suffering from or susceptible to rhinitis, especially allergic rhinitis. We also provide the use of a compound of formula (I) or a pharmaceutically acceptable salt thereof in the manufacture of a medicament for the treatment or prevention of rhinitis, especially allergic rhinitis.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

For the above mentioned therapeutic indications, the dose of the compound to be administered will depend on the compound employed, the disease being treated, the mode of administration, the age, weight and sex of the patient. Such factors may be determined by the attending physician. However, in general, satisfactory results are obtained when the compounds are administered to a human at a daily dosage of between 0.1 mg/kg to 100 mg/kg (measured as the active ingredient).

The compounds of formula (I) may be used on their own, or in the form of appropriate pharmaceutical formulations comprising the compound of the invention in combination with a pharmaceutically acceptable diluent, adjuvant or carrier. Particularly preferred are compositions not containing material capable of causing an adverse reaction, for example, an allergic reaction. Conventional procedures for the selection and preparation of suitable pharmaceutical formulations are described in, for example, "Pharmaceuticals—The Science of Dosage Form Designs", M. E. Aulton, Churchill Livingstone, 1988.

In another aspect the invention provides a pharmaceutical formulation comprising a therapeutically effective amount of a compound of formula (I), or a pharmaceutically acceptable salt thereof, in admixture with a pharmaceutically acceptable adjuvant, diluent or carrier, for use in the treatment or prophylaxis of diseases or conditions in which inhibition of kinase Itk activity is beneficial.

In a more particular aspect, the invention provides a pharmaceutical formulation comprising a therapeutically effective amount of a compound of formula (I), or a pharmaceutically acceptable salt thereof, in admixture with a pharmaceutically acceptable adjuvant, diluent or carrier, for use in the treatment or prophylaxis of allergic, autoimmune, inflammatory, proliferative and hyperproliferative diseases and immune-mediated diseases including rejection of transplanted organs or tissues and Acquired Immunodeficiency Syndrome (AIDS).

According to the invention, there is provided a pharmaceutical formulation comprising preferably less than 95% by weight and more preferably less than 50% by weight of a compound of formula (I) in admixture with a pharmaceutically acceptable diluent or carrier.

We also provide a method of preparation of such pharmaceutical formulations that comprises mixing the ingredients.

The compounds may be administered topically, for example, to the lungs and/or the airways, in the form of solutions, suspensions, HFA aerosols or dry powder formulations, for example, formulations in the inhaler device known as the Turbuhaler®; or systemically, for example, by oral administration in the form of tablets, pills, capsules, syrups, powders or granules; or by parenteral administration, for example, in the form of sterile parenteral solutions or suspensions; or by rectal administration, for example, in the form of suppositories.

Dry powder formulations and pressurized HFA aerosols of the compounds of the invention may be administered by oral or nasal inhalation. For inhalation, the compound is desirably finely divided. The finely divided compound preferably has a mass median diameter of less than 10 μm, and may be suspended in a propellant mixture with the assistance of a dispersant, such as a $C_8$-$C_{20}$ fatty acid or salt thereof, (for example, oleic acid), a bile salt, a phospholipid, an alkyl saccharide, a perfluorinated or polyethoxylated surfactant, or other pharmaceutically acceptable dispersant.

The compounds of the invention may also be administered by means of a dry powder inhaler. The inhaler may be a single or a multi dose inhaler, and may be a breath actuated dry powder inhaler.

One possibility is to mix the finely divided compound with a carrier substance, for example, a mono-, di- or polysaccharide, a sugar alcohol, or an other polyol. Suitable carriers are sugars, for example, lactose, glucose, raffinose, melezitose, lactitol, maltitol, trehalose, sucrose, mannitol; and starch. Alternatively the finely divided compound may be coated by another substance. The powder mixture may also be dispensed into hard gelatine capsules, each containing the desired dose of the active compound.

Another possibility is to process the finely divided powder into spheres which break up during the inhalation procedure. This spheronized powder may be filled into the drug reservoir of a multidose inhaler, for example, that known as the Turbuhaler® in which a dosing unit meters the desired dose which is then inhaled by the patient. With this system the active compound, with or without a carrier substance, is delivered to the patient.

For oral administration the active compound may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum, titanium dioxide, and the like. Alternatively, the tablet may be coated with a suitable polymer dissolved in a readily volatile organic solvent.

For the preparation of soft gelatine capsules, the compound may be admixed with, for example, a vegetable oil or polyethylene glycol. Hard gelatine capsules may contain granules of the compound using either the above mentioned excipients for tablets. Also liquid or semisolid formulations of the drug may be filled into hard gelatine capsules.

Liquid preparations for oral application may be in the form of syrups or suspensions, for example, solutions containing the compound, the balance being sugar and a mixture of ethanol, water, glycerol and propylene glycol. Optionally such liquid preparations may contain colouring agents, flavouring agents, saccharine and/or carboxymethylcellulose as a thickening agent or other excipients known to those skilled in art.

The compounds of the invention may also be administered in conjunction with other compounds used for the treatment of the above conditions.

Certain compounds of formula (I) are novel.

Therefore a further aspect of the invention provides a compound of formula (Ia)

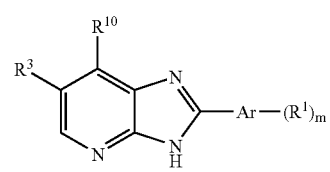

(Ia)

wherein:

$R^3$ represents halogen, C1 to 3 alkyl or C1 to 3 alkoxy;

$R^{10}$ represents H;

Ar represents phenyl, a 5- or 6-membered heteroaromatic ring or an indole ring; said heteroaromatic ring incorporating 1 to 3 heteroatoms independently selected from O, N and S;

m represents an integer 1 or 2;

when m represents 1, $R^1$ represents $(CH_2)_n NR^4 R^5$ and n represents an integer 0 or 1;

when m represents 2, one $R^1$ represents chloro or OMe and the other $R^1$ represents $(CH_2)_n NR^4 R^5$ and n represents an integer 0 or 1;

$R^4$ represents H or C1 to 4 alkyl;

$R^5$ represents $CH_2 Ar$;

$Ar^2$ represents phenyl, a 5- or 6-membered heteroaromatic ring or a benzimidazole ring; said heteroaromatic ring incorporating 1 to 3 heteroatoms independently selected from O, N and S; said phenyl, heteroaromatic or benzimidazole ring being optionally further substituted by one or two groups independently selected from halogen, C1 to 4 alkyl, CN, $CH_2OH$, C1 to 4 alkoxy, $CO_2 Me$, $CH_2 OAc$ and pyridyl;

or a pharmaceutically acceptable salt thereof.

In one embodiment, $R^1$ in formula (Ia) represents $(CH_2)_n NR^4 R^5$ and n represents the integer 0.

In one embodiment, $R^3$ in formula (Ia) represents halogen. In another embodiment, $R^3$ in formula (Ia) represents bromo.

In another embodiment, Ar in formula (Ia) represents phenyl.

Particular novel compounds of formula (Ia) include:
4-({[4-(6-bromo-3H-imidazo[4,5-b]pyridin-2-yl)phenyl]amino}methyl)benzonitrile
N-benzyl-N-[4-(6-bromo-3H-imidazo[4,5-b]pyridin-2-yl)phenyl]amine
N-[4-(6-bromo-3H-imidazo[4,5-b]pyridin-2-yl)phenyl]-N-(1H-imidazol-2-ylmethyl)amine
N-[4-(6-bromo-3H-imidazo[4,5-b]pyridin-2-yl)phenyl]-N-(1H-imidazol-5-ylmethyl)amine
3-({[4-(6-bromo-3H-imidazo[4,5-b]pyridin-2-yl)phenyl]amino}methyl)benzonitrile
N-[4-(6-bromo-3H-imidazo[4,5-b]pyridin-2-yl)phenyl]-N-(4-methoxybenzyl)amine
N-[4-(6-bromo-3H-imidazo[4,5-b]pyridin-2-yl)phenyl]-N-(2-methoxybenzyl)amine
N-[4-(6-bromo-3H-imidazo[4,5-b]pyridin-2-yl)phenyl]-N-(3-methoxybenzyl)amine
N-[4-(6-bromo-3H-imidazo[4,5-b]pyridin-2-yl)phenyl]-N-(2-chlorobenzyl)amine
N-[4-(6-bromo-3H-imidazo[4,5-b]pyridin-2-yl)phenyl]-N-(4-chlorobenzyl)amine
N-[4-(6-bromo-3H-imidazo[4,5-b]pyridin-2-yl)phenyl]-N-(1H-pyrazol-3-ylmethyl)amine
N-[4-(6-bromo-3H-imidazo[4,5-b]pyridin-2-yl)phenyl]-N-(3-chlorobenzyl)amine
[5-({[4-(6-bromo-3H-imidazo[4,5-b]pyridin-2-yl)phenyl]amino}methyl)-2-furyl]methanol
N-[4-(6-bromo-3H-imidazo[4,5-b]pyridin-2-yl)phenyl]-N-(thien-2-ylmethyl)amine
N-[4-(6-bromo-3H-imidazo[4,5-b]pyridin-2-yl)phenyl]-N-(2-furylmethyl)amine
N-[4-(6-bromo-3H-imidazo[4,5-b]pyridin-2-yl)phenyl]-N-(thien-3-ylmethyl)amine
N-[4-(6-bromo-3H-imidazo[4,5-b]pyridin-2-yl)phenyl]-N-[(4-methyl-1H-imidazol-5-yl)methyl]amine
N-[4-(6-bromo-3H-imidazo[4,5-b]pyridin-2-yl)phenyl]-N-(3-furylmethyl)amine
N-[4-(6-bromo-3H-imidazo[4,5-b]pyridin-2-yl)phenyl]-N-(1,3-thiazol-2-ylmethyl)amine
N-[4-(6-bromo-3H-imidazo[4,5-b]pyridin-2-yl)phenyl]-N-[(4-bromothien-2-yl)methyl]amine
N-[4-(6-bromo-3H-imidazo[4,5-b]pyridin-2-yl)phenyl]-N-(1H-imidazol-4-ylmethyl)amine
N-[4-(6-bromo-3H-imidazo[4,5-b]pyridin-2-yl)phenyl]-N-[(2-methyl-1H-imidazol-5-yl)methyl]amine
N-[4-(6-bromo-3H-imidazo[4,5-b]pyridin-2-yl)phenyl]-N-[(3,5-dimethylisoxazol-4-yl)methyl]amine
[5-({[4-(6-bromo-3H-imidazo[4,5-b]pyridin-2-yl)phenyl]amino}methyl)-2-furyl]methyl acetate
N-[4-(6-bromo-3H-imidazo[4,5-b]pyridin-2-yl)phenyl]-N-[(5-pyridin-2-ylthien-2-yl)methyl]amine
N-[4-(6-bromo-3H-imidazo[4,5-b]pyridin-2-yl)phenyl]-N-[(1-methyl-1H-benzimidazol-2-yl)methyl]amine
N-[4-(6-bromo-3H-imidazo[4,5-b]pyridin-2-yl)phenyl]-N-[(2-ethyl-1H-imidazol-5-yl)methyl]amine
N-[4-(6-bromo-3H-imidazo[4,5-b]pyridin-2-yl)phenyl]-N-[(1-methyl-1H-imidazol-5-yl)methyl]amine
methyl 4-({[4-(6-bromo-3H-imidazo[4,5-b]pyridin-2-yl)phenyl]amino}methyl)-1-methyl-1H-pyrrole-2-carboxylate
N-benzyl-5-(6-bromo-3H-imidazo[4,5-b]pyridin-2-yl)pyridin-2-amine
5-(6-bromo-3H-imidazo[4,5-b]pyridin-2-yl)-N-(3-methoxybenzyl)pyridin-2-amine and pharmaceutically acceptable salts thereof.

Another aspect of the invention provides a compound of formula (Ib)

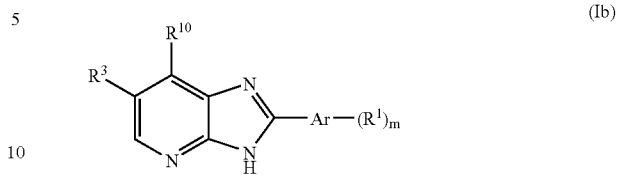

wherein:
$R^3$ represents halogen, C1 to 3 alkyl or C1 to 3 alkoxy;
$R^{10}$ represents H;
Ar represents phenyl, a 5- or 6-membered heteroaromatic ring or an indole ring; said heteroaromatic ring incorporating 1 to 3 heteroatoms independently selected from O, N and S;
m represents an integer 1 or 2;
when m represents 1, $R^1$ represents $OR^2$;
when m represents 2, one $R^1$ represents chloro or OMe and the other $R^1$ represents $OR^2$;
$R^2$ represents C3 to 4 alkyl substituted by $NR^6R^7$ and by OH;
$R^6$ represents H, C1 to 4 alkyl or $CH_2CH_2OCH_3$;
$R^7$ represents H, C1 to 6 alkyl, C3 to 6 cycloalkyl, $Ar^3$, a 5 or 6 membered saturated or partially unsaturated heterocyclic ring incorporating 1 or 2 heteroatoms selected independently from O, N and S and optionally substituted by Me, Et or $CO_2Et$; said C1 to 6 alkyl being optionally substituted by one or more groups selected independently from OH, CN, $CONMe_2$, CONHMe, C1 to 4 alkoxy, halogen, $NMe_2$, $Ar^4$, and a 5 or 6 membered saturated heterocyclic ring incorporating 1 or 2 heteroatoms selected independently from O, N and S and optionally also incorporating a carbonyl group; said C3 to 6 cycloalkyl being optionally substituted by OH or CN;
or the group —$NR^6R^7$ together represents a 5 to 7 membered saturated azacyclic ring optionally incorporating 1 additional heteroatom selected from O and $NR^9$; and optionally substituted by one or more substituents selected independently from OH, $NMe_2$, $CONH_2$, $CH_2OH$, $CH_2CH_2OH$, phenyl, pyridyl, piperidinyl and methoxyphenyl;
$R^9$ represents $CH_2CH_2OH$, $COCH_3$, Me, $CO_2Et$, $CH_2CH_2OMe$ or a six membered aromatic or azaaromatic ring optionally further substituted by one or more substituents selected independently from Cl, CN, OMe and $CF_3$;
$Ar^3$ represents thiazolyl, triazolyl or tetrazolyl;
$Ar^4$ represents phenyl, a 5- or 6-membered heteroaromatic ring or an indole ring; said heteroaromatic ring incorporating 1 to 3 heteroatoms independently selected from O, N and S; said phenyl, heteroaromatic or indole ring being optionally further substituted by one or two groups independently selected from halogen and OMe;

or a pharmaceutically acceptable salt thereof.

In one embodiment, $R^1$ in formula (Ib) represents $OCH_2CHOHCH_2NR^6R^7$.

In one embodiment, $R^3$ in formula (Ib) represents halogen.
In another embodiment, $R^3$ in formula (Ib) represents bromo.
In another embodiment, Ar in formula (Ib) represents phenyl.

Particular novel compounds of formula (Ib) include:
1-[4-(6-bromo-3H-imidazo[4,5-b]pyridin-2-yl)phenoxy]-3-pyrrolidin-1-ylpropan-2-ol
1-[4-(6-bromo-3H-imidazo[4,5-b]pyridin-2-yl)phenoxy]-3-morpholin-4-ylpropan-2-ol
1-{(3-[4-(6-bromo-3H-imidazo[4,5-b]pyridin-2-yl)phenoxy]-2-hydroxypropyl}pyrrolidin-3-ol 1-[4-(6-bromo-3H-imidazo[4,5-b]pyridin-2-yl)phenoxy]-3-piperidin-1-ylpropan-2-ol
1-[4-(6-bromo-3H-imidazo[4,5-b]pyridin-2-yl)phenoxy]-3-(diethylamino)propan-2-ol
1-{3-[4-(6-bromo-3H-imidazo[4,5-b]pyridin-2-yl)phenoxy]-2-hydroxypropyl}piperidin-4-ol
1-(4-acetylpiperazin-1-yl)-3-[4-(6-bromo-3H-imidazo[4,5-b]pyridin-2-yl)phenoxy]propan-2-ol
1-[4-(6-bromo-3H-imidazo[4,5-b]pyridin-2-yl)phenoxy]-3-[3-(dimethylamino)pyrrolidin-1-yl]propan-2-ol
4-[({2-hydroxy-3-[4-(6-methyl-3H-imidazo[4,5-b]pyridin-2-yl)phenoxy]propyl}amino)methyl]phenol 1-[4-(6-bromo-3H-imidazo[4,5-b]pyridin-2-yl)phenoxy]-3-[(2-hydroxyethyl)(methyl)amino]propan-2-ol
3-[{3-[4-(6-bromo-3H-imidazo[4,5-b]pyridin-2-yl)phenoxy]-2-hydroxypropyl}(methyl)amino]propanenitrile
4-{3-[4-(6-bromo-3H-imidazo[4,5-b]pyridin-2-yl)phenoxy]-2-hydroxypropyl}piperazin-1-ol
$N^2$-{3-[4-(6-bromo-3H-imidazo[4,5-b]pyridin-2-yl)phenoxy]-2-hydroxypropyl}-$N^1$,$N^1$,$N^2$-trimethylglycinamide
1-[benzyl(methyl)amino]-3-[4-(6-bromo-3H-imidazo[4,5-b]pyridin-2-yl)phenoxy]propan-2-ol
1-[4-(6-bromo-3H-imidazo[4,5-b]pyridin-2-yl)phenoxy]-3-[methyl(2-phenylethyl)amino]propan-2-ol
1-[4-(6-bromo-3H-imidazo[4,5-b]pyridin-2-yl)phenoxy]-3-(4-phenylpiperazin-1-yl)propan-2-ol
1-[4-(6-bromo-3H-imidazo[4,5-b]pyridin-2-yl)phenoxy]-3-(4-pyridin-2-ylpiperazin-1-yl)propan-2-ol
1-[2-({3-[4-(6-bromo-3H-imidazo[4,5-b]pyridin-2-yl)phenoxy)-2-hydroxypropyl}amino)ethyl]imidazolidin-2-one
1-[4-(6-bromo-3H-imidazo[4,5-b]pyridin-2-yl)phenoxy]-3-[(3-methoxybenzyl)amino]propan-2-ol
1-[4-(6-bromo-3H-imidazo[4,5-b]pyridin-2-yl)phenoxy]-3-[(2-chlorobenzyl)amino]propan-2-ol
1-[4-(6-bromo-3H-imidazo[4,5-b]pyridin-2-yl)phenoxy]-3-[(4-chlorobenzyl)amino]propan-2-ol
1-[4-(6-bromo-3H-imidazo[4,5-b]pyridin-2-yl)phenoxy]-3-[(3-chlorobenzyl)amino]propan-2-ol
ethyl 4-({3-[4-(6-bromo-3H-imidazo[4,5-b]pyridin-2-yl)phenoxy]-2-hydroxypropyl}amino)piperidine-1-carboxylate
1-[4-(6-bromo-3H-imidazo[4,5-b]pyridin-2-yl)phenoxy]-3-[4-(2-methoxyethyl)piperazin-1-yl]propan-2-ol
1-[4-(6-bromo-3H-imidazo[4,5-b]pyridin-2-yl)phenoxy]-3-(cyclopropylamino)propan-2-ol
3-({3-[4-(6-bromo-3H-imidazo[4,5-b]pyridin-2-yl)phenoxy]-2-hydroxypropyl}amino)propan-2-ol
1-[4-(6-bromo-3H-imidazo[4,5-b]pyridin-2-yl)phenoxy]-3-[(2-methoxyethyl)amino]propan-2-ol
2-({3-[4-(6-bromo-3H-imidazo[4,5-b]pyridin-2-yl)phenoxy]-2-hydroxypropyl}amino)propan-1-ol
1-(benzylamino)-3-[4-(6-bromo-3H-imidazo[4,5-b]pyridin-2-yl)phenoxy]propan-2-ol
1-[4-(6-bromo-3H-imidazo[4,5-b]pyridin-2-yl)phenoxy]-3-[(pyridin-3-ylmethyl)amino]propan-2-ol
1-[4-(6-bromo-3H-imidazo[4,5-b]pyridin-2-yl)phenoxy]-3-[(pyridin-4-ylmethyl)amino]propan-2-ol
1-[4-(6-bromo-3H-imidazo[4,5-b]pyridin-2-yl)phenoxy]-3-[(1-ethylpiperidin-3-yl)amino]propan-2-ol
1-[4-(6-bromo-3H-imidazo[4,5-b]pyridin-2-yl)phenoxy]-3-[(2-morpholin-4-ylethyl)amino]propan-2-ol
1-[3-({3-[4-(6-bromo-3H-imidazo[4,5-b]pyridin-2-yl)phenoxy]-2-hydroxypropyl}amino)propyl]pyrrolidin-2-one
1-{3-[4-(6-bromo-3H-imidazo[4,5-b]pyridin-2-yl)phenoxy]-2-hydroxypropyl) piperidin-3-ol
1-{3-[4-(6-bromo-3H-imidazo[4,5-b]pyridin-2-yl)phenoxy]-2-hydroxypropyl}prolinamide
1-[4-(6-bromo-3H-imidazo[4,5-b]pyridin-2-yl)phenoxy]-3-[4-(hydroxymethyl)piperidin-1-yl]propan-2-ol
1-[4-(6-bromo-3H-imidazo[4,5-b]pyridin-2-yl)phenoxy]-3-[2-(hydroxymethyl)piperidin-1-yl]propan-2-ol
1-{3-[4-(6-bromo-3H-imidazo[4,5-b]pyridin-2-yl)phenoxy]-2-hydroxypropyl}piperidine-4-carboxamide
1-{3-[4-(6-bromo-3H-imidazo[4,5-b]pyridin-2-yl)phenoxy]-2-hydroxypropyl}piperidine-3-carboxamide
1-[4-(6-bromo-3H-imidazo[4,5-b]pyridin-2-yl)phenoxy]-3-[4-(2-hydroxyethyl)piperazin-1-yl]propan-2-ol
2-(4-{3-[4-(6-bromo-3H-imidazo[4,5-b]pyridin-2-yl)phenoxy]-2-hydroxypropyl}piperazin-1-yl)benzonitrile
6-(4-{3-[4-(6-bromo-3H-imidazo[4,5-b]pyridin-2-yl)phenoxy)-2-hydroxypropyl}piperazin-1-yl)nicotinonitrile
1-[4-(6-bromo-3H-imidazo[4,5-b]pyridin-2-yl)phenoxy]-3-(1,3-thiazol-2-ylamino)propan-2-ol
1-[4-(6-bromo-3H-imidazo[4,5-b]pyridin-2-yl)phenoxy]-3-(4-pyrazin-2-ylpiperazin-1-yl)propan-2-ol
1-[4-(6-bromo-3H-imidazo[4,5-b]pyridin-2-yl)phenoxy]-3-[(2-methoxybenzyl)amino]propan-2-ol
4-[(3-[4-(6-bromo-3H-imidazo[4,5-b]pyridin-2-yl)phenoxy]-2-hydroxypropyl}(methyl)amino]cyclohexanecarbonitrile
1-[4-(6-bromo-3H-imidazo[4,5-b]pyridin-2-yl)phenoxy]-3-(2-pyridin-3-ylpiperidin-1-yl)propan-2-ol
1-{3-[4-(6-bromo-3H-imidazo[4,5-b]pyridin-2-yl)phenoxy]-2-hydroxypropyl}-4-phenylpiperidin-4-ol
2-({3-[4-(6-bromo-3H-imidazo[4,5-b]pyridin-2-yl)phenoxy]-2-hydroxypropyl}amino)-3-methylbutan-1-ol
1-[4-(6-bromo-3H-imidazo[4,5-b]pyridin-2-yl)phenoxy]-3-[4-(3-methoxyphenyl)piperazin-1-yl]propan-2-ol and pharmaceutically acceptable salts thereof.

Another aspect of the invention provides a compound of formula (Ic)

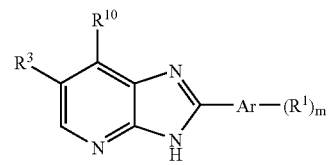

(Ic)

wherein:
$R^3$ represents halogen, C1 to 3 alkyl or C1 to 3 alkoxy;
$R^{10}$ represents H;
Ar represents phenyl, a 5- or 6-membered heteroaromatic ring or an indole ring; said heteroaromatic ring incorporating 1 to 3 heteroatoms independently selected from O, N and S;
m represents an integer 1 or 2;
when m represents 1, $R^1$ represents OR;
when m represents 2, one $R^1$ represents chloro, $NO_2$ or OMe and the other $R^1$ represents $OR^2$;
$R^2$ represents C2 to 4 alkyl substituted by a group $NR^6R^7$;
$R^6$ represents H, C1 to 4 alkyl or $CH_2CH_2OCH_3$;
$R^7$ represents H, C1 to 6 alkyl, C3 to 6 cycloalkyl, $Ar^3$, a 5 or 6 membered saturated or partially unsaturated heterocyclic ring incorporating 1 or 2 heteroatoms selected independently from O, N and S and optionally substituted by Me, Et or $CO_2Et$; said C1 to 6 alkyl being optionally substituted by one or more groups selected independently from OH, CN, $CONMe_2$, CONHMe, C1 to 4 alkoxy, halogen, $NMe_2$, $Ar^4$, and a 5 or 6 membered saturated heterocyclic ring incorporating 1 or 2 heteroatoms selected independently from O, N and S and optionally also incorporating a carbonyl group; said C3 to 6 cycloalkyl being optionally substituted by OH or CN; or the group —NR$^6$R$^7$ together represents a 5 or 6 membered saturated azacyclic ring optionally incorporating 1 additional heteroatom selected from O and NR$^9$; and optionally substituted by one or more substituents selected independently from OH, NMe$_2$, CONH$_2$, CH$_2$OH, CH$_2$CH$_2$OH, phenyl, pyridyl, piperidinyl or methoxyphenyl;

R$^9$ represents CH$_2$CH$_2$OH, COCH$_3$, Me, CO$_2$Et, CH$_2$CH$_2$OMe or a six membered aromatic or azaaromatic ring optionally further substituted by one or more substituents selected independently from Cl, CN, OMe and CF$_3$;

Ar$^3$ represents thiazolyl, triazolyl or tetrazolyl;

Ar$^4$ represents phenyl, a 5- or 6-membered heteroaromatic ring or an indole ring; said heteroaromatic ring incorporating 1 to 3 heteroatoms independently selected from O, N and S; said phenyl, heteroaromatic or indole ring being optionally further substituted by one or two groups independently selected from halogen and OMe;

or a pharmaceutically acceptable salt thereof, with the provisos that:

i) when R$^6$ represents H or C1 to 4 alkyl, R$^3$ does not represent unsubstituted C1 to 4 alkyl; and ii) that the group —NR$^6$R$^7$ does not represent unsubstituted morpholine, thiomorpholine, 4-methylpiperazine or 4-phenylpiperazine.

In one embodiment, R$^3$ in formula (Ic) represents halogen.
In another embodiment, R$^3$ in formula (Ic) represents bromo.
In another embodiment, Ar in formula (Ic) represents phenyl.

Particular novel compounds of formula (Ic) include:
6-bromo-2-[4-(2-{4-[3-chloro-5-(trifluoromethyl)pyridin-2-yl]piperazin-1-yl}ethoxy)phenyl]-3H-imidazo[4,5-b]pyridine 6-bromo-2-[4-(2-piperidin-1-ylethoxy)phenyl]-3H-imidazo[4,5-b]pyridine
6-bromo-2-[4-(3-piperidin-1-ylpropoxy)phenyl]-3H-imidazo[4,5-b]pyridine
6-bromo-2-[4-(3-pyrrolidin-1-ylpropoxy)phenyl]-3H-imidazo[4,5-b]pyridine
N-{2-[4-(6-bromo-3H-imidazo[4,5-b]pyridin-2-yl)phenoxy]ethyl}-N-(tetrahydrofuran-2-ylmethyl)amine
6-bromo-2-[4-(2-pyrrolidin-1-ylethoxy)phenyl]-3H-imidazo[4,5-b]pyridine
2-[{2-[4-(6-bromo-3H-imidazo[4,5-b]pyridin-2-yl)phenoxy]ethyl}(methyl)amino]ethanol
3-[{2-[4-(6-bromo-3H-imidazo[4,5-b]pyridin-2-yl)phenoxy]ethyl}(methyl)amino]propanenitrile
1-{2-[4-(6-bromo-3H-imidazo[4,5-b]pyridin-2-yl)phenoxy]ethyl}pyrrolidin-3-ol
1-{2-[4-(6-bromo-3H-imidazo[4,5-b]pyridin-2-yl)phenoxy]ethyl}-N,N-dimethylpyrrolidin-3-amine
N-{2-[4-(6-bromo-3H-imidazo[4,5-b]pyridin-2-yl)phenoxy]ethyl}-N,1-dimethylpyrrolidin-3-amine
N$^2$-{2-[4-(6-bromo-3H-imidazo[4,5-b]pyridin-2-yl)phenoxy]ethyl}-N$^1$,N$^1$,N$^2$-trimethylglycinamide
N-{2-[4-(6-bromo-3H-imidazo[4,5-b]pyridin-2-yl)phenoxy]ethyl}-N-ethyl-N',N'-dimethylethane-1,2-diamine
N-benzyl-N-{2-[4-(6-bromo-3H-imidazo[4,5-b]pyridin-2-yl)phenoxy]ethyl}-N-methylamine
2-{4-[2-(4-acetylpiperazin-1-yl)ethoxy]phenyl}-6-bromo-3H-imidazo[4,5-b]pyridine
N-{2-[4-(6-bromo-3H-imidazo[4,5-b]pyridin-2-yl)phenoxy]ethyl}-N,N-bis(2-methoxyethyl)amine
N-{2-[4-(6-bromo-3H-imidazo[4,5-b]pyridin-2-yl)phenoxy]ethyl}-N-methyl-N-(2-phenylethyl)amine
6-bromo-2-{4-[2-(4-pyridin-2-ylpiperazin-1-yl)ethoxy]phenyl}-3H-imidazo[4,5-b]pyridine
N-{2-[4-(6-bromo-3H-imidazo[4,5-b]pyridin-2-yl)phenoxy]ethyl}-N-[3-(1H-imidazol-1-yl)propyl]amine
N-{2-[4-(6-bromo-3H-imidazo[4,5-b]pyridin-2-yl)phenoxy]ethyl}-N-(4-methoxybenzyl)amine
N-{2-[4-(6-bromo-3H-imidazo[4,5-b]pyridin-2-yl)phenoxy]ethyl}-N-(3-methoxybenzyl)amine
N-{2-[4-(6-bromo-3H-imidazo[4,5-b]pyridin-2-yl)phenoxy]ethyl}-N-(4-chlorobenzyl)amine
N-{2-[4-(6-bromo-3H-imidazo[4,5-b]pyridin-2-yl)phenoxy]ethyl}-N-(3-chlorobenzyl)amine ethyl 4-({2-[4-(6-bromo-3H-imidazo[4,5-b]pyridin-2-yl)phenoxy]ethyl}amino)piperidine-1-carboxylate
6-bromo-2-(4-{2-[4-(2-methoxyethyl)piperazin-1-yl]ethoxy}phenyl)-3H-imidazo[4,5-b]pyridine
1-({2-[4-(6-bromo-3H-imidazo[4,5-b]pyridin-2-yl)phenoxy]ethyl}amino)propan-2-ol
N-{2-[4-(6-bromo-3H-imidazo[4,5-b]pyridin-2-yl)phenoxy]ethyl}-N-(2-methoxyethyl)amine
2-({2-[4-(6-bromo-3H-imidazo[4,5-b]pyridin-2-yl)phenoxy]ethyl}amino)propan-1-ol
N-{2-[4-(6-bromo-3H-imidazo[4,5-b]pyridin-2-yl)phenoxy]ethyl}-N-(2-furylmethyl)amine
N-{2-[4-(6-bromo-3H-imidazo[4,5-b]pyridin-2-yl)phenoxy]ethyl}-N-(tetrahydrofuran-2-ylmethyl)amine
N-benzyl-N-{2-[4-(6-bromo-3H-imidazo[4,5-b]pyridin-2-yl)phenoxy]ethyl}amine
N-{2-[4-(6-bromo-3H-imidazo[4,5-b]pyridin-2-yl)phenoxy]ethyl}-N-(pyridin-3-ylmethyl)amine
N-{2-[4-(6-bromo-3H-imidazo[4,5-b]pyridin-2-yl)phenoxy]ethyl}-N-(pyridin-4-ylmethyl)amine
N-{2-[4-(6-bromo-3H-imidazo[4,5-b]pyridin-2-yl)phenoxy]ethyl}-N-(thien-2-ylmethyl)amine
N-{2-[4-(6-bromo-3H-imidazo[4,5-b]pyridin-2-yl)phenoxy]ethyl}-N-(1-phenylethyl)amine
N-{2-[4-(6-bromo-3H-imidazo[4,5-b]pyridin-2-yl)phenoxy]ethyl}-1-ethylpiperidin-3-amine
N-{2-[4-(6-bromo-3H-imidazo[4,5-b]pyridin-2-yl)phenoxy]ethyl 1-N-(2-morpholin-4-ylethyl)amine
N-{2-[4-(6-bromo-3H-imidazo[4,5-b]pyridin-2-yl)phenoxy]ethyl}-N-(2-methoxybenzyl)amine
1-[3-({2-[4-(6-bromo-3H-imidazo[4,5-b]pyridin-2-yl)phenoxy]ethyl}amino)propyl]pyrrolidin-2-one
N-{2-[4-(6-bromo-3H-imidazo[4,5-b]pyridin-2-yl)phenoxy]ethyl 1-N-[2-(4-chlorophenyl)ethyl]amine
4-[{2-[4-(6-bromo-3H-imidazo[4,5-b]pyridin-2-yl)phenoxy]ethyl}(methyl)amino]cyclohexanecarbonitrile
1-{2-[4-(6-bromo-3H-imidazo[4,5-b]pyridin-2-yl)phenoxy]ethyl}piperidin-3-ol
6-bromo-2-{4-[2-(2-pyridin-3-ylpiperidin-1-yl)ethoxy]phenyl}-3H-imidazo[4,5-b]pyridine
N-{2-[4-(6-bromo-3H-imidazo[4,5-b]pyridin-2-yl)phenoxy]ethyl}-N-cyclopentylamine
1-{2-[4-(6-bromo-3H-imidazo[4,5-b]pyridin-2-yl)phenoxy]ethyl}-4-phenylpiperidin-4-ol
N-{2-[4-(6-bromo-3H-imidazo[4,5-b]pyridin-2-yl)phenoxy]ethyl}-N-[2-(1H-imidazol-4-yl)ethyl]amine
1-{2-[4-(6-bromo-3H-imidazo[4,5-b]pyridin-2-yl)phenoxy]ethyl}piperidine-3-carboxamide
6-bromo-2-{4-[2-(4-pyrazin-2-ylpiperazin-1-yl)ethoxy]phenyl}-3H-imidazo[4,5-b]pyridine
(1S,2S)-2-({2-[4-(6-bromo-3H-imidazo[4,5-b]pyridin-2-yl)phenoxy]ethyl}amino)cyclohexanol 6-bromo-2-(4-{2-[4-(3-methoxyphenyl)piperazin-1-yl]ethoxy}phenyl)-3H-imidazo[4,5-b]pyridine
(1-{2-[4-(6-bromo-3H-imidazo[4,5-b]pyridin-2-yl)phenoxy]ethyl}piperidin-4-yl)methanol
4-({2-[4-(6-bromo-3H-imidazo[4,5-b]pyridin-2-yl)phenoxy]ethyl}amino)cyclohexanol (1-{2-[4-(6-bromo-3H-imidazo[4,5-b]pyridin-2-yl)phenoxy]ethyl}piperidin-2-yl)methanol
1'-(2-[4-(6-bromo-3H-imidazo[4,5-b]pyridin-2-yl)phenoxy]ethyl}-1,4'-bipiperidine
N-{2-[4-(6-bromo-3H-imidazo[4,5-b]pyridin-2-yl)phenoxy]ethyl}-1,3-thiazol-2-amine
1-{2-[4-(6-bromo-3H-imidazo[4,5-b]pyridin-2-yl)phenoxy]ethyl}piperidine-4-carboxamide
N-{2-[4-(6-bromo-3H-imidazo[4,5-b]pyridin-2-yl)phenoxy]ethyl}-1H-1,2,4-triazol-3-amine
2-(4-{2-[4-(6-bromo-3H-imidazo[4,5-b]pyridin-2-yl)phenoxy]ethyl}piperazin-1-yl)benzonitrile
6-(4-{2-[4-(6-bromo-3H-imidazo[4,5-b]pyridin-2-yl)phenoxy]ethyl}piperazin-1-yl)nicotinonitrile
1-{2-[4-(6-bromo-3H-imidazo[4,5-b]pyridin-2-yl)phenoxy]ethyl}prolinamide
6-bromo-2-(4-{2-[4-(2-methoxyphenyl)piperidin-1-yl]ethoxy}phenyl)-3H-imidazo[4,5-b]pyridine
2-(4-{2-[4-(6-bromo-3H-imidazo[4,5-b]pyridin-2-yl)phenoxy]ethyl}piperazin-1-yl)ethanol
1-{2-[4-(6-bromo-3H-imidazo[4,5-b]pyridin-2-yl)phenoxy]ethyl}piperidin-4-ol
6-bromo-2-(4-{2-[4-(2-methoxyphenyl)piperazin-1-yl]ethoxy}phenyl)-3H-imidazo[4,5-b]pyridine
(2S)-2-({2-[4-(6-bromo-3H-imidazo[4,5-b]pyridin-2-yl)phenoxy]ethyl}amino)-3-methylbutan-1-ol
N-{2-[4-(6-bromo-3H-imidazo[4,5-b]pyridin-2-yl)phenoxy]ethyl}-4,5-dihydro-1,3-thiazol-2-amine
N-{2-[4-(6-bromo-3H-imidazo[4,5-b]pyridin-2-yl)phenoxy]ethyl}-N-[2-(1H-indol-3-yl)ethyl]amine
(2S)-2-({2-[4-(6-bromo-3H-imidazo[4,5-b]pyridin-2-yl)phenoxy]ethyl}amino)-2-phenylethanol
N-{2-[4-(6-bromo-3H-imidazo[4,5-b]pyridin-2-yl)phenoxy]ethyl}-1H-tetrazol-5-amine
(1S,2R)-2-({2-[4-(6-bromo-3H-imidazo[4,5-b]pyridin-2-yl)phenoxy]ethyl}amino)cyclohexanol
6-chloro-2-[4-(2-piperidin-1-ylethoxy)phenyl]-3H-imidazo[4,5-b]pyridine
6-bromo-2-[4-(2-morpholin-4-ylethoxy)-3-nitrophenyl]-3H-imidazo[4,5-b]pyridine and pharmaceutically acceptable salts thereof.

Another aspect of the invention provides a compound of formula (Id)

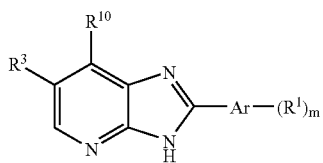

(Id)

wherein:
$R^3$ represents halogen, CN, C1 to 3 alkyl or C1 to 3 alkoxy;
Ar represents phenyl, a 5- or 6-membered heteroaromatic ring or an indole ring; said heteroaromatic ring incorporating 1 to 3 heteroatoms independently selected from O, N and S;
$R^1$ represents H, halogen, CN, C1 to 6 alkyl, $NO_2$, $SO_2Me$, C1 to 6 alkynyl, $CH_2OH$, $OR^2$, $(CH_2)_nNR^4R^5$ or phenyl optionally substituted by $NH_2$;
m represents an integer 1 or 2; and when m represents 2, each $R^1$ may be selected independently;
n represents an integer 0 or 1;
$R^2$ represents H or C1 to 4 alkyl; said C1 to 4 alkyl being optionally further substituted by a group selected from $Ar^1$, $CONH_2$, $CO_2Et$, OH, $NR^6R^7$, halogen and epoxy; and when substituted by $NR^6R^7$ or halogen, said alkyl is optionally further substituted by OH;
$R^4$ represents H, C1 to 4 alkyl or $CH_2Ar^2$;
$R^5$ represents H, C1 to 6 alkyl, C2 to 6 alkanoyl, $SO_2$—Ar or $CH_2Ar^2$; said alkyl group being optionally further substituted by a 5 to 7 membered saturated azacyclic ring optionally incorporating one additional heteroatom selected from O, S and $NR^8$;
or the group —$NR^4R^5$ together represents a 5 to 7 membered saturated azacyclic ring optionally incorporating one additional heteroatom selected from O, S and $NR^8$;
$R^6$ represents H, C1 to 4 alkyl or $CH_2CH_2OCH_3$;
$R^7$ represents H, C1 to 6 alkyl, C3 to 6 cycloalkyl, Ar, a 5 or 6 membered saturated or partially unsaturated heterocyclic ring incorporating 1 or 2 heteroatoms selected independently from O, N and S and optionally substituted by Me, Et or $CO_2Et$; said C1 to 6 alkyl being optionally substituted by one or more groups selected independently from OH, CN, $CONMe_2$, CONHMe, C1 to 4 alkoxy, halogen, $NMe_2$, Ar, and a 5 or 6 membered saturated heterocyclic ring incorporating 1 or 2 heteroatoms selected independently from O, N and S and optionally also incorporating a carbonyl group; said C3 to 6 cycloalkyl being optionally substituted by OH or CN;
or the group —$NR^6R^7$ together represents a 5 to 7 membered saturated azacyclic ring optionally incorporating 1 additional heteroatom selected from O and $NR^9$; and optionally substituted by one or more substituents selected independently from OH, $NMe_2$, $CONH_2$, $CH_2OH$, $CH_2CH_2OH$, phenyl, pyridyl, piperidinyl or methoxyphenyl;
$R^8$ represents H, C1 to 6 alkyl or $CH_2Ph$;
$R^9$ represents $CH_2CH_2OH$, $COCH_3$, Me, $CO_2Et$, $CH_2CH_2OMe$ or a six membered aromatic or azaaromatic ring optionally further substituted by one or more substituents selected independently from Cl, CN, OMe and $CF_3$;
$R^{10}$ represents halogen, CN, C1 to 4 alkyl, C1 to 4 alkoxy, $NR^{14}R^{15}$ or a group —X—Y—Z;
$R^{14}$ and $R^{15}$ independently represent H or C1 to 4 alkyl; said alkyl being optionally further substituted by OH;
X represents O, S, a bond or $NR^{16}$ wherein $R^{16}$ represents H or C1 to 4 alkyl; said alkyl being optionally further substituted by OH;
Y represents C1 to 4 alkyl or a bond;
Z represents:
i) phenyl, naphthyl or a 5- or 6-membered heteroaromatic ring system containing one to three heteroatoms independently selected from O, N and S; or
ii) a five- or six-membered saturated heterocyclic ring containing one or two heteroatoms independently selected from O, N and S; said ring optionally being benzo fused; or
iii) C3 to 6 cycloalkyl;
said ring Z being optionally substituted by one or more substituents independently selected from halogen, OH, C1 to 4 alkyl, C1 to 4 alkoxy, hydroxymethyl, methylsulphonyl and $NR^{17}R^{18}$;
$R^{17}$ and $R^{18}$ independently represent H, C1 to 4 alkyl, formyl or C2 to 4 alkanoyl; or the group $NR^{17}R^{18}$ together represents a saturated 5 to 7 membered azacyclic ring optionally containing one further heteroatom selected from O, N and S;

$Ar^1$ represents phenyl, thiazolyl or thiadiazolyl, optionally further substituted by halogen;

$Ar^2$ represents phenyl, a 5- or 6-membered heteroaromatic ring or a benzimidazole ring; said heteroaromatic ring incorporating 1 to 3 heteroatoms independently selected from O, N and S; said phenyl or heteroaromatic or benzimidazole ring being optionally further substituted by one or two groups independently selected from halogen, C1 to 4 alkyl, CN, $CH_2OH$, C1 to 4 alkoxy, $CO_2Me$, $CH_2OAc$ and pyridyl;

$Ar^3$ represents thiazolyl, triazolyl or tetrazolyl;

$Ar^4$ represents phenyl, a 5- or 6-membered heteroaromatic ring or an indole ring; said heteroaromatic ring incorporating 1 to 3 heteroatoms independently selected from O, N and S; said phenyl, heteroaromatic or indole ring being optionally further substituted by one or two groups independently selected from halogen and OMe;

$Ar^5$ represents phenyl, a 5- or 6-membered heteroaromatic ring or a quinoline ring; said heteroaromatic ring incorporating 1 to 3 heteroatoms independently selected from O, N and S; said phenyl or heteroaromatic or quinoline ring being optionally further substituted by halogen, C1 to 4 alkyl, CN, C1 to 4 alkoxy, and $OCH_2CH_2CN$;

With the proviso that when $R^{10}$ represents halogen, C1 to 4 alkyl, C1 to 4 alkoxy or $NH_2$; and Ar represents phenyl; then said phenyl is not substituted at the 4-position by C1 to 2 alkoxy, OH, halogen or C1 to 4 alkyl.

In one embodiment, $R^3$ in formula (Id) represents halogen. In another embodiment, $R^3$ in formula (Id) represents bromo. In another embodiment, $R^3$ in formula (Id) represents chloro.

In another embodiment, Ar in formula (Id) represents phenyl.

In another embodiment, m represents 1 and $R^1$ represents $OR^2$.

In another embodiment, $R^2$ represents C2 to 4 alkyl substituted by a group $NR^6R^7$.

Particular novel compounds of formula (Id) include:

6,7-dichloro-2-[4-(2-morpholin-4-ylethoxy)phenyl]-3H-imidazo[4,5-b]pyridine
6-chloro-N-(2-methoxyphenyl)-2-{4-[2-(4-morpholinyl)ethoxy]phenyl}-1H-imidazo[4,5-b]pyridin-7-amine
2-[(6-chloro-2-{4-[2-(4-morpholinyl)ethoxy]phenyl}-1H-imidazo[4,5-b]pyridin-7-yl)amino]phenol
6-chloro-N-[1-(methylsulfonyl)-3-pyrrolidinyl]-2-{4-[2-(4-morpholinyl)ethoxy]phenyl}-1H-imidazo[4,5-b]pyridin-7-amine
6-chloro-N-cyclopentyl-2-{4-[2-(4-morpholinyl)ethoxy]phenyl}-1H-imidazo[4,5-b]pyridin-7-amine
N-benzyl-6-chloro-2-{4-[2-(4-morpholinyl)ethoxy]phenyl}-1H-imidazo[4,5-b]pyridin-7-amine
6-chloro-2-{4-[2-(4-morpholinyl)ethoxy]phenyl}-1H-imidazo[4,5-b]pyridin-7-amine
6-chloro-2-{4-[2-(4-morpholinyl)ethoxy]phenyl}-7-(1H-pyrrol-1-yl)-1H-imidazo[4,5-b]pyridine
1-(6-chloro-2-{4-[2-(4-morpholinyl)ethoxy]phenyl}-1H-imidazo[4,5-b]pyridin-7-yl)-3-pyrrolidinamine
1-(6-chloro-2-{4-[2-(4-morpholinyl)ethoxy]phenyl}-1H-imidazo[4,5-b]pyridin-7-yl)-3-pyrrolidinylformamide
6-chloro-N-(2-ethylphenyl)-2-{4-[2-(4-morpholinyl)ethoxy]phenyl}-1H-imidazo[4,5-b]pyridin-7-amine
6-chloro-7-(2,3-dihydro-1H-indol-1-yl)-2-{4-[2-(4-morpholinyl)ethoxy]phenyl}-1H-imidazo[4,5-b]pyridine
6-chloro-7-(4-morpholinyl)-2-{4-[2-(4-morpholinyl)ethoxy]phenyl}-1H-imidazo[4,5-b]pyridine
6-chloro-2-[4-(2-morpholin-4-ylethoxy)phenyl]-N-pyridin-3-yl-3H-imidazo[4,5-b]pyridin-7-amine
[3-({6-chloro-2-[4-(2-morpholin-4-ylethoxy)phenyl(−3H{imidazo[4,5-b]pyridin-7-yl}amino)phenyl]methanol
6-chloro-N-(2-fluorophenyl)-2-[4-(2-morpholin-4-ylethoxy)phenyl]-3H-imidazo[4,5-b]pyridin-7-amine
6-chloro-2-{4-[2-(4-morpholinyl)ethoxy]phenyl}-N-phenyl-1H-imidazo[4,5-b]pyridin-7-amine
6-chloro-N-(3-ethylphenyl)-2-{4-[2-(4-morpholinyl)ethoxy]phenyl}-1H-imidazo[4,5-b]pyridin-7-amine
2-[benzyl(6-chloro-2-{4-[2-(4-morpholinyl)ethoxy]phenyl}-1H-imidazo[4,5-b]pyridin-7-yl)amino]ethanol
2-[(6-chloro-2-{4-[2-(4-morpholinyl)ethoxy]phenyl}-1H-imidazo[4,5-b]pyridin-7-yl)amino]ethanol
N-benzyl-6-chloro-N-methyl-2-{4-[2-(4-morpholinyl)ethoxy]phenyl}-1H-imidazo[4,5-b]pyridin-7-amine
6-chloro-N-methyl-2-[4-[2-(4-morpholinyl)ethoxy]phenyl}-1H-imidazo[4,5-b]pyridin-7-amine
7-(benzylthio)-6-chloro-2-(4-[2-(4-morpholinyl)ethoxy]phenyl}-1H-imidazo[4,5-b]pyridine
6-chloro-N-[4-(methylsulfonyl)phenyl]-2-{4-[2-(4-morpholinyl)ethoxy]phenyl}-1H-imidazo[4,5-b]pyridin-7-amine
6-chloro-2-{4-[2-(4-morpholinyl)ethoxy]phenyl}-N-[4-(4-morpholinyl)phenyl]-1H-imidazo[4,5-b]pyridin-7-amine
N'-(6-chloro-2-{4-[2-(4-morpholinyl)ethoxy]phenyl}-1H-imidazo[4,5-b]pyridin-7-yl)-N,N-diethyl-1,4-benzenediamine
N-{4-[(6-chloro-2-{4-[2-(4-morpholinyl)ethoxy]phenyl}-1H-imidazo[4,5-b]pyridin-7-yl)amino]phenyl}acetamide
6-chloro-2-{4-[2-(4-morpholinyl)ethoxy]phenyl}-7-phenoxy-1H-imidazo[4,5-b]pyridine
6-chloro-2-{4-[2-(4-morpholinyl)ethoxy]phenyl}-7-[2-(1-pyrrolidinyl)ethoxy]-1H-imidazo[4,5-b]pyridine
6-chloro-2-[4-(2-morpholin-4-ylethoxy)phenyl]-N-(2-morpholin-4-ylethyl)-3H-imidazo[4,5-b]pyridin-7-amine
6-chloro-2-[4-(2-morpholin-4-ylethoxy)phenyl]-7-pyrrolidin-1-yl-3H-imidazo[4,5-b]pyridine
6-chloro-2-[4-(2-morpholin-4-ylethoxy)phenyl]-N-(1-phenylethyl)-3H-imidazo[4,5-b]pyridin-7-amine
6-chloro-7-(4-methylphenyl)-2-[4-(2-morpholin-4-ylethoxy)phenyl]-3H-imidazo[4,5-b]pyridine
6-chloro-7-(3-methoxyphenyl)-2-[4-(2-morpholin-4-ylethoxy)phenyl]-3H-imidazo[4,5-b]pyridine
N-(3-{6-chloro-2-[4-(2-morpholin-4-ylethoxy)phenyl]-3H-imidazo[4,5-b]pyridin-7-yl}phenyl)acetamide
6-chloro-2-[4-(2-morpholin-4-ylethoxy)phenyl]-7-thien-3-yl-3H-imidazo[4,5-b]pyridine
2-[4-(2-morpholin-4-ylethoxy)phenyl]-3H-imidazo[4,5-b]pyridine-6,7-dicarbonitrile
7-chloro-2-[4-(2-morpholin-4-ylethoxy)phenyl]-3H-imidazo[4,5-b]pyridine-6-carbonitrile
7-anilino-2-(4-{2-[(2-methoxyethyl)(methyl)amino]ethoxy}phenyl)-3H-imidazo[4,5-b]pyridine-6-carbonitrile
6,7-dichloro-2-{4-[2-(4-morpholinyl)ethoxy]-3-nitrophenyl}-1H-imidazo[4,5-b]pyridine
5-(6,7-dichloro-1H-imidazo[4,5-b]pyridin-2-yl)-2-[2-(4-morpholinyl)ethoxy]aniline
2-amino-5-(6-chloro-7-methyl-3H-imidazo[4,5-b]pyridin-2-yl)phenol
5-(6-chloro-7-methyl-3H-imidazo[4,5-b]pyridin-2-yl)-2-{[(2R)-pyrrolidin-2-ylmethyl]amino}phenol
[5-(6-chloro-7-methyl-3H-imidazo[4,5-b]pyridin-2-yl)-2-(2-morpholin-4-ylethoxy)phenyl][(2R)-pyrrolidin-2-ylmethyl]amine
4-(6-chloro-7-methyl-3H-imidazo[4,5-b]pyridin-2-yl)-N'-(2-morpholin-4-ylethyl)benzene-1,2-diamine

[5-(6-chloro-7-methyl-3H-imidazo[4,5-b]pyridin-2-yl)-2-(4-methylpiperazin-1-yl)phenyl]amine 6,7-dichloro-2-[4-(4-morpholinyl)phenyl]-1H-imidazo[4,5-b]pyridine

[5-(6,7-dichloro-3H-imidazo[4,5-b]pyridin-2-yl)-2-morpholin-4-ylphenyl]amine 2-(4-aminophenyl)-6-chloro-N-phenyl-3H-imidazo[4,5-b]pyridin-7-amine N-[4-(6,7-dichloro-3H-imidazo[4,5-b]pyridin-2-yl)phenyl]-N-(2-morpholin-4-ylethyl)amine 6-bromo-7-methyl-2-[4-(2-piperidin-1-ylethoxy)phenyl]-3H-imidazo[4,5-b]pyridine 6-bromo-7-methyl-2-(4-nitrophenyl)-1H-imidazo[4,5-b]pyridine 4-(6-bromo-7-methyl-1H-imidazo[4,5-b]pyridin-2-yl)aniline N-[4-(6-bromo-7-methyl-1H-imidazo[4,5-b]pyridin-2-yl)phenyl]-3-cyanobenzenesulfonamide N-[4-(6-bromo-7-methyl-1H-imidazo[4,5-b]pyridin-2-yl)phenyl]-4-cyanobenzenesulfonamide N-[4-(6-bromo-7-methyl-1H-imidazo[4,5-b]pyridin-2-yl)phenyl]quinoline-8-sulfonamide N-[4-(6-bromo-7-methyl-1H-imidazo[4,5-b]pyridin-2-yl)phenyl]-4-methoxybenzenesulfonamide N-[4-(6-bromo-7-methyl-1H-imidazo[4,5-b]pyridin-2-yl)phenyl]-4-(2-cyanoethoxy)benzenesulfonamide N-[4-(6-bromo-7-methyl-1H-imidazo[4,5-b]pyridin-2-yl)phenyl]-1-methyl-1H-imidazole-4-sulfonamide N-[4-(6,7-dichloro-1H-imidazo[4,5-b]pyridin-2-yl)phenyl]-4-methoxybenzenesulfonamide 6-chloro-2-{4-[(2-morpholin-4-ylethyl)amino]phenyl}-N-phenyl-3H-imidazo[4,5-b]pyridin-7-amine 6-chloro-7-methoxy-2-[4-(2-morpholin-4-ylethoxy)phenyl]-3H-imidazo[4,5-b]pyridine 6-chloro-2-{4-[di(3-cyanobenzyl)amino]phenyl}-7-methoxy-1-yl-3H-imidazo[4,5-b]pyridine 3-({[4-(6-chloro-7-methoxy-1H-imidazo[4,5-b]pyridin-2-yl)phenyl]amino}methyl)benzonitrile)

N-[4-(6-chloro-7-methoxy-1H-imidazo[4,5-b]pyridin-2-yl)phenyl]-4-cyanobenzenesulfonamide 6-chloro-7-methoxy-2-[4-(2-piperidin-1-ylethoxy)phenyl]-3H-imidazo[4,5-b]pyridine and pharmaceutically acceptable salts thereof.

According to the invention there is also provided a compound of formula (Ia), (Ib), (Ic) or (Id) or a pharmaceutically acceptable salt thereof, for use as a medicament.

The present invention includes compounds of formulae (I) and (Ia) and (Ib) and (Ic) and (Id) in the form of salts, in particular acid addition salts. Suitable salts include those formed with both organic and inorganic acids. Such acid addition salts will normally be pharmaceutically acceptable although salts of non-pharmaceutically acceptable acids may be of utility in the preparation and purification of the compound in question. Thus, preferred salts include those formed from hydrochloric, hydrobromic, sulphuric, phosphoric, citric, tartaric, lactic, pyruvic, acetic, succinic, fumaric, maleic, methanesulphonic and benzenesulphonic acids.

In a further aspect the invention provides a process for the preparation of a compound of formula (Ia), (Ib), (Ic) or (Id) which comprises:

a) reaction of a compound of the general formula (II):

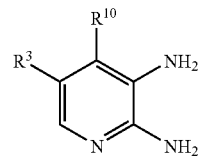

(II)

in which $R^3$ and $R^{10}$ are as defined in formula (Ia), (Ib), (Ic) or (Id), with a compound of formula (III):

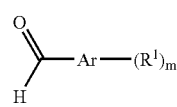

(III)

in which m, $R^1$ and Ar are as defined in formula (Ia), (Ib), (Ic) or (Id), in the presence of an oxidizing agent; or b) reaction of a compound of the general formula (II):

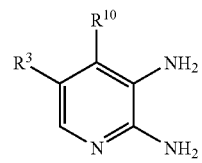

(II)

in which $R^3$ and $R^{10}$ are as defined in formula (Ia), (Ib), (Ic) or (Id), with a compound of formula (IV):

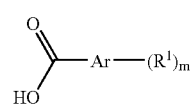

(IV)

in which m, $R^1$ and Ar are as defined in formula (Ia), (Ib), (Ic) or (Id), in the presence of $POCl_3$; or c) reaction of a compound of formula (V):

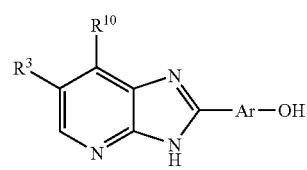

(V)

in which $R^3$, $R^{10}$ and Ar are as defined in formula (Ib), (Ic) or (Id); with a compound of formula (VI):

$R^2$-LG    (VI)

in which $R^2$ is as defined in formula (Ib), (Ic) or (Id) and LG represents a leaving group; or d) reaction of a compound of the general formula (VII):

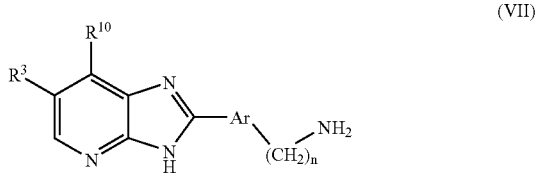

in which n, $R^3$, $R^{10}$ and Ar are as defined in formula (Ia) or (Id); with a compound of formula (VIII):

Ar²—CHO (VIII)

in which $Ar^2$ is as defined in formula (Ia) or (Id), or e) reaction of a compound of the general formula (IX):

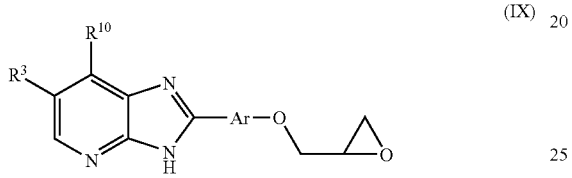

in which $R^3$, $R^{10}$ and Ar are as defined in formula (Ib) or (Id); with a compound of formula (X):

HNR⁶R⁷ (X)

in which $R^6$ and $R^7$ are as defined in formula (Ib) or (Id); and where desired or necessary converting the resultant compound of formula (Ia), (Ib), (Ic) or (Id) or another salt thereof, into a pharmaceutically acceptable salt thereof; or converting one compound of formula (Ia), (Ib), (Ic) or (Id) into another compound of formula (Ia), (Ib), (Ic) or (Id); and where desired converting the resultant compound of formula (Ia), (Ib), (Ic) or (Id) into an optical isomer thereof.

In process (a), the reaction is carried out in the presence of a suitable oxidising agent, for example, iron(III) chloride, and air is continuously bubbled through the reaction solution. Suitable solvents include N,N-dimethylformamide. The reaction is generally carried out at an elevated temperature up to the boiling point of the solvent and for a sufficient length of time for the reaction to go to completion. When the reaction is conducted in N,N-dimethylformamide at about 120° C., typical reaction times are from 2 to 20 hours.

In process (b), the reaction is carried out using an excess of $POCl_3$, the $POCl_3$ thereby acting as both reagent and solvent. If necessary, a suitable co-solvent may also be used. The reaction is generally carried out at an elevated temperature up to the boiling point of the solvent and for a sufficient length of time for the reaction to go to completion. When the reaction is conducted in $POCl_3$ at about 100° C., typical reaction times are 5 hours or more.

In process (c), the reaction is generally carried out in the presence of a suitable base, for example, sodium hydride, and in a suitable organic solvent, for example, N,N-dimethylformamide.

In process (d), the reaction is carried out in the presence of a suitable reducing agent, for example, sodium triacetoxyborohydride or catalytic hydrogenation.

In process (e), the reaction is carried out in a suitable organic solvent, for example, N,N-dimethylformamide, at a suitable temperature between room temperature and the boiling point of the solvent.

It will be appreciated that in the above processes, certain functional groups may need to be protected using standard protecting groups. The protection and deprotection of functional groups is, for example, described in 'Protective Groups in Organic Chemistry', edited by J. W. F. McOmie, Plenum Press (1973), and 'Protective Groups in Organic Synthesis', 3rd edition, T. W. Greene & P. G. M. Wuts, Wiley-Interscience (1999).

Compounds of the general formula (IX) may be prepared by reacting a compound of the general formula (V) with a compound of the general (VI) in which $R^2$ is 2,3-epoxypropyl.

Compounds of formula (Id) in which $R^{10}$ is bonded to the imidazopyridine ring via O or N may be prepared by nucleophilic substitution of the corresponding compounds of formula (Id) in which $R^{10}$ represents chloro. The displacement reaction may be conducted under either basic, or acidic or neutral conditions, and at elevated temperature.

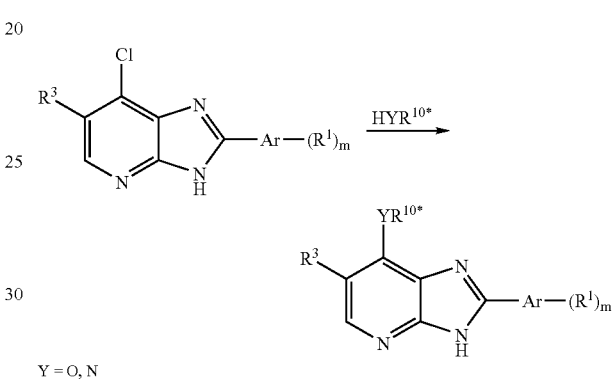

Y = O, N

Compounds of formula (Id) in which $R^{10}$ represents an optionally substituted aromatic ring may be prepared by nucleophilic substitution of the corresponding compound of formula (Id) in which $R^{10}$ represents chloro by a palladium-catalysed coupling reaction with a suitably functionalized aromatic compound. For example, using Heck coupling of the bromo aromatic compound according to known literature coupling protocols (J. Heterocyclic Chem., 1977, 14, 813-821).

2,3-Diamino-pyridines of formula (II) may be prepared from the corresponding 2-aminopyridine by nitration followed by reduction using methods that are well known in the literature.

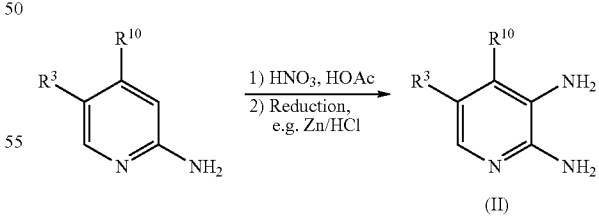

Salts of compounds of formula (I) may be formed by reacting the free base or a salt, enantiomer, tautomer or protected derivative thereof, with one or more equivalents of the appropriate acid. The reaction may be carried out in a solvent or medium in which the salt is insoluble, or in a solvent in which the salt is soluble followed by subsequent removal of is the solvent in vacuo or by freeze drying. Suitable solvents include, for example, water, dioxan, ethanol, 2-propanol, tetrahydrofuran or diethyl ether, or mixtures thereof. The reaction may be a metathetical process or it may be carried out on an ion exchange resin.

The compounds of the invention and intermediates may be isolated from their reaction mixtures, and if necessary further purified, by using standard techniques.

The compounds of formula (Ia), (Ib), (Ic) and (Id) may exist in enantiomeric or diastereoisomeric forms or mixtures thereof, all of which are included within the scope of the invention. The various optical isomers may be isolated by separation of a racemic mixture of the compounds using conventional techniques, for example, fractional crystallisation or HPLC. Alternatively, the individual enantiomers may be made by reaction of the appropriate optically active starting materials under reaction conditions that will not cause racemisation.

Intermediate compounds may also exist in enantiomeric forms and may be used as purified enantiomers, diastereomers, racemates or mixtures thereof.

The compounds of formula (Ia), (Ib), (Ic) and (Id) and their pharmaceutically acceptable salts, enantiomers, racemates and tautomers, are useful because they possess pharmacological activity in animals. The compounds of formula (Ia), (Ib), (Ic) and (Id) have activity as pharmaceuticals, in particular as modulators of kinase activity, especially Itk kinase activity, and as such are predicted to be useful in therapy. They may be used in the treatment or prophylaxis of allergic, autoimmune, inflammatory, proliferative and hyperproliferative diseases and immune-mediated diseases including rejection of transplanted organs or tissues and Acquired Immunodeficiency Syndrome (AIDS).

Examples of these medical conditions are disclosed above.

The compounds of formula (Ia), (Ib), (Ic) and (Id) may be used on their own, or in the form of appropriate pharmaceutical formulations comprising the compound of the invention in combination with a pharmaceutically acceptable diluent, adjuvant or carrier. Particularly preferred are compositions not containing material capable of causing an adverse reaction, for example, an allergic reaction. Conventional procedures for the selection and preparation of suitable pharmaceutical formulations are described in, for example, "Pharmaceuticals—The Science of Dosage Form Designs", M. E. Aulton, Churchill Livingstone, 1988.

In another aspect the invention provides a pharmaceutical formulation comprising a therapeutically effective amount of a compound of formula (Ia), (Ib), (Ic) or (Id), or a pharmaceutically acceptable salt thereof, in admixture with a pharmaceutically acceptable adjuvant, diluent or carrier.

The following Examples are intended to illustrate, but in no way limit the scope of the invention.

General methods All reactions were performed in dried glassware in an argon atmosphere at room temperature, unless otherwise noted. Microwave assisted reactions were carried out in a CEM microwave reactor, Model Discovery, using a performance of 300 watts and 10 ml vessels with septa, if not stated otherwise. All reagents and solvents were dried over molecular sieves (3 Å) before use. Merck Silica gel 60 (0.040-0.063 mm) was used for preparative silica gel chromatography. A Kromasil KR-100-5-C18 column (250×20 mm, Akzo Nobel) and mixtures of acetonitrile/water (containing 0.1% trifluoroacetic acid) at a flow rate of 10 ml/min were used for preparative HPLC. Reactions were monitored at 254 nm by analytical HPLC, using a Kromasil C-18 column (150×4.6 mm) and a gradient (containing 0.1% trifluoroacetic acid) of 5 to 100% of acetonitrile in water at a flow rate of 1 ml/min. Evaporations of solvents were performed under reduced pressure using a rotary evaporator at a maximum temperature of 60° C. Products were dried under reduced pressure at 40° C.

$^1$H-NMR spectra were recorded on a Varian Inova 400 MHz or Varian Mercury 300 MHz instrument. The central solvent peak of chloroform-d ($\delta_H$ 7.27 ppm), dimethylsulfoxide-d$_6$ ($\delta_H$ 2.50 ppm) or methanol-d$_4$ ($\delta_H$ 3.35 ppm) were used as internal references. Low resolution mass spectra obtained on a Hewlett Packard 1100 LC-MS system equipped with a APCI ionisation chamber.

Preparation 1 5-Bromo-2,3-diaminopyridine

The title compound was prepared essentially as described by Petrow et al., *J. Chem. Soc.* (1948) 1389, 1391.

A mixture of 2-amino-5-bromo-3-nitropyridine (62.2 g, 285 mmol), iron powder (171 g, 3.06 mol), concentrated hydrochloric acid (2.85 ml), water (60 ml) and ethanol (230 ml) was refluxed for 2 h, filtered whilst warm, the solids washed twice with ethanol (2×150 ml) and the combined ethanol solutions were evaporated to dryness. The crude solid was recrystallized from water, using decolourising charcoal, filtered whilst warm, the solids washed twice with warm ethanol (2×100 ml), the ethanol evaporated off and the precipitate was filtered off, washed with water (3×75 ml) and dried to afford the title compound (27 g, 50%).

$^1$H NMR (DMSO-d$_6$): δ 7.26 (1H, d); 6.78 (1H, d); 5.57 (2H, s); 4.97 (2H, s). APCI-MS m/z: 188.1/190.1 [MH$^+$].

EXAMPLE 1

4-(6-Bromo-3H-imidazo[4,5-b]pyridin-2-yl)phenol

A mixture of 5-bromo-2,3-diaminopyridine (11.3 g, 60 mmol), 4-hydroxybenzaldehyde (7.3 g, 60 mmol) and iron (III) chloride hexahydrate (0.48 g, 1.8 mmol) in DMF (200 ml) was heated to 120° C. with air bubbling continuously through the solution until the reaction was complete (typical reaction time 4 to 16 h).

The reaction mixture was poured into ice-water, filtered and the solids washed with water, ethanol, methanol and then dried. The solids were recrystallized twice from DMF (250 ml then 150 ml), filtered, washed with methanol, diethyl ether and dried to afford the title compound (11.3 g, 65%).

$^1$H NMR (DMSO-d$_6$): δ 13.36 (1H, brs); 10.12 (1H, brs); 8.33 (1H, s); 8.15 (1H, s); 8.05 (2H, d); 6.91 (2H, d). APCI-MS m/z: 290.1/292 [MH$^+$].

Following the general method of Example 1, the compounds of Examples 2 to 38 were prepared:

EXAMPLE 2

N-{3-[4-(6-Bromo-3H-imidazo[4,5-b]pyridin-2-yl)phenoxy]propyl}-N,N-dimethylamine The title compound was prepared from 5-bromo-2,3-diaminopyridine (376 mg, 2 mmol) and 4-[3-(dimethylamino)propoxy]benzaldehyde (420 mg, 2 mmol).

$^1$H NMR (DMSO-d$_6$): δ 13.39 (1H, brs); 8.35 (1H, d); 8.19 (1H, brs); 8.15 (2H, d); 7.11 (2H, d); 4.08 (2H, t); 2.36 (2H, t); 2.14 (6H, s); 1.87 (2H, qv). APCI-MS m/z: 375.2/377.1 [MH$^+$].

EXAMPLE 3

6-Bromo-2-4-[(5-chloro-1,2,3-thiadiazol-4-yl)methoxy]phenyl}-3H-imidazo[4,5-b]pyridine The title compound was prepared from 5-bromo-2,3-diaminopyridine and 4-[(5-chloro-1,2,3-thiadiazol-4-yl)methoxy]benzaldehyde.

¹H NMR (DMSO-d₆): δ 13.50 (1H, brs); 8.37 (1H, d); 8.21 (1H, brs); 8.20 (2H, d); 7.30 (2H, d); 5.59 (2H, s). APCI-MS m/z: 422/424 [MH⁺].

EXAMPLE 4

6-Bromo-2-{4-[(2-chloro-1,3-thiazol-5-yl)methoxy]phenyl}-3H-imidazo[4,5-b]pyridine The title compound was prepared from 5-bromo-2,3-diaminopyridine and 4-[(2-chloro-1,3-thiazol-5-yl)methoxy]benzaldehyde.

¹H NMR (DMSO-d₆): δ 13.47 (1H, brs); 8.36 (1H, d); 8.20 (1H, brs); 8.17 (2H, d); 7.84 (1H, s); 7.22 (2H, d); 5.54 (2H, s). APCI-MS m/z: 421/423 [MH⁺].

EXAMPLE 5

6-Bromo-2-[4-(2-{4-[3-chloro-5-(trifluoromethyl)pyridin-2-yl]piperazin-1-ylethoxy)phenyl]-3H-imidazo[4,5-b]pyridine The title compound was prepared from 5-bromo-2,3-diaminopyridine and 4-(2-[4-[3-chloro-5-(trifluoromethyl)-2-pyridinyl]piperazino]ethoxy)]benzaldehyde.

¹H NMR (DMSO-d₆): δ 13.45 (1H, brs); 8.54 (1H, d); 8.35 (1H, d); 8.19 (1H, brs); 8.17 (1H, brs); 8.15 (2H, d); 7.15 (2H, d); 4.22 (2H, t); 3.46 (4H, brt); 2.80 (2H, t); 2.66 (4H, brt). APCI-MS m/z: 581.1/583.1 [MH⁺].

EXAMPLE 6

6-Bromo-2-[4-(2-piperidin-1-ylethoxy)phenyl]-3H-imidazo[4,5-b]pyridine

The title compound was prepared from 5-bromo-2,3-diaminopyridine and 4-[2-(1-piperidinyl)ethoxy]benzaldehyde.

¹H NMR (DMSO-d₆): δ 13.41 (1H, brs); 8.35 (1H, d); 8.19 (1H, brs); 8.15 (2H, d); 7.12 (2H, d); 4.16 (2H, t); 2.67 (2H, t); 2.43 (4H, brt); 1.49 (4H, m); 1.38 (2H, m). APCI-MS m/z: 401.1/403.1 [MH⁺].

EXAMPLE 7

[5-(6-Bromo-3H-imidazo[4,5-b]pyridin-2-yl)-2-furyl]methanol

The title compound was prepared from 5-bromo-2,3-diaminopyridine and 5-hydroxymethyl-2-furaldehyde.

¹H NMR (DMSO-d₆): δ 13.58 (1H, brs); 8.38 (1H, d); 8.17 (1H, brs); 7.28 (1H, d); 6.57 (1H, d); 5.43 (1H, t); 4.52 (2H, d). APCI-MS m/z: 294/296 [MH⁺].

EXAMPLE 8

6-Bromo-2-(7-methyl-1H-indol-3-yl)-3H-imidazo[4,5-b]pyridine

The title compound was prepared from 5-bromo-2,3-diaminopyridine and 7-methylindole-3-carboxaldehyde.

¹H NMR (DMSO-d₆): δ 13.11 (1H, brs); 11.81 (1H, s); 8.31 (1H, s); 8.29-8.24 (2H, m); 8.13 (1H, brs); 7.11 (1H, t); 7.02 (1H, brd); 2.51 (3H, s). APCI-MS m/z: 327/329 [MH⁺].

EXAMPLE 9

6-Bromo-2-(1-phenyl-1H-1,2,3-triazol-4-yl)-3H-imidazo[4,5-b]pyridine

The title compound was prepared from 5-bromo-2,3-diaminopyridine and 1-phenyl-1H-1,2,3-triazole-4-carboxaldehyde.

¹H NMR (DMSO-d₆): δ 13.66 (1H, brs); 9.60 (1H, s); 8.42 (1H, d); 8.20 (1H, brs); 8.02 (2H, d); 7.68-7.51 (3H, m). APCI-MS m/z: 341/343 [MH⁺].

EXAMPLE 10

6-Bromo-2-(1H-pyrrol-2-yl)-3H-imidazo[4,5-b]pyridine

The title compound was prepared from 5-bromo-2,3-diaminopyridine and pyrrole-2-carboxaldehyde.

¹H NMR (DMSO-d₆): δ 13.11 (1H, brs); 12.00 (1H, s); 8.27 (1H, d); 8.06 (1H, s); 6.99 (2H, m); 6.21 (1H, m). APCI-MS m/z: 263/265 [MH⁺].

EXAMPLE 11

6-Bromo-2-(1H-pyrazol-3-yl)-3H-imidazo[4,5-b]pyridine

The title compound was prepared from 5-bromo-2,3-diaminopyridine and pyrazole-3-carbaldehyde.

¹H NMR (DMSO-d₆): δ 13.49 (2H, brs); 8.37 (1H, s); 8.15 (1H, brs); 7.92 (1H, s); 6.94 (1H, d). APCI-MS m/z: 264/266 [MH⁺].

EXAMPLE 12

6-Bromo-2-(4-bromo-1H-pyrazol-3-yl)-3H-imidazo[4,5-b]pyridine

The title compound was prepared from 5-bromo-2,3-diaminopyridine and 4-bromo-1H-pyrazole-5-carbaldehyde.

¹H NMR (DMSO-d₆): δ 13.76 (2H, brs); 8.42 (1H, s); 8.22 (2H, brs). APCI-MS m/z: 341.9/343.9/345.9 [MH⁺].

EXAMPLE 13

6-Bromo-2-(2-methyl-1H-imidazol-5-yl)-3H-imidazo[4,5-b]pyridine

The title compound was prepared from 5-bromo-2,3-diaminopyridine 2-methyl-1H-imidazole-4-carbaldehyde.

¹H NMR (DMSO-d₆/D₂O): δ 8.29 (1H, s); 8.06 (1H, s); 7.78 (1H, s); 2.34 (3H, s). APCI-MS m/z: 278/280 [MH⁺].

EXAMPLE 14

4-(6-Bromo-3H-imidazo[4,5-b]pyridin-2-yl)-2-methoxyphenol

The title compound was prepared from 5-bromo-2,3-diaminopyridine and 4-hydroxy-3-methoxybenzaldehyde.

¹H NMR (DMSO-d₆): δ 13.35 (1H, brs); 9.71 (1H, brs); 8.33 (1H, d); 8.16 (1H, brs); 7.77 (1H, d); 7.67 (1H, dd); 6.91 (1H, d); 3.87 (3H, s). APCI-MS m/z: 320/322 [MH⁺].

EXAMPLE 15

4-(6-Bromo-3H-imidazo[4,5-b]pyridin-2-yl)-2-chlorophenol

The title compound was prepared from 5-bromo-2,3-diaminopyridine and 3-chloro-4-hydroxybenzaldehyde.

$^1$H NMR (DMSO-d$_6$): δ 13.54 (1H, brs); 10.92 (1H, brs); 8.36 (1H, s); 8.22 (1H, brs); 8.20 (1H, d); 8.01 (1H, dd); 7.12 (1H, d). APCI-MS m/z: 323.9/325.9 [MH$^+$].

EXAMPLE 16

4-(6-Bromo-3H-imidazo[4,5-b]pyridin-2-yl)-3-methoxyphenol

The title compound was prepared from 5-bromo-2,3-diaminopyridine and 4-hydroxy-2-methoxybenzaldehyde.

$^1$H NMR (DMSO-d$_6$): δ 12.58 (NH-tautomer, s); 12.06 (NH-tautomer, s); 10.22 (1H, s); 8.39-7.96 (3H, m); 6.57 (2H, m); 3.96 (3H, brd). APCI-MS m/z: 320/322 [MH$^+$].

EXAMPLE 17

4-(6-Bromo-3H-imidazo[4,5-b]pyridin-2-yl)-3-chlorophenol

The title compound was prepared from 5-bromo-2,3-diaminopyridine and 2-chloro-4-hydroxybenzaldehyde.

$^1$H NMR (DMSO-d$_6$): δ 13.15 (1H, brs); 10.53 (1H, brs); 8.41 (1H, d); 8.23 (1H, brs); 7.73 (1H, d); 6.99 (1H, d); 6.90 (1H, dd). APCI-MS m/z: 323.9/325.9 [MH$^+$].

EXAMPLE 18

N-[4-(6-bromo-3H-imidazo[4,5-b]pyridin-2-yl)-3-methoxyphenyl]-N,N-dimethylamine

The title compound was prepared from 5-bromo-2,3-diaminopyridine and 4-dimethylamino-2-methoxybenzaldehyde.

$^1$H NMR (DMSO-d$_6$): δ 12.04 (1H, brs); 8.29 (1H, s); 8.12 (1H, d); 8.01 (1H, brs); 6.47 (1H, d); 6.35 (1H, s); 4.00 (3H, s); 3.03 (6H, s). APCI-MS m/z: 347/349 [MH$^+$].

EXAMPLE 19

2-[4-(6-Bromo-3H-imidazo[4,5-b]pyridin-2-yl)phenoxy]ethanol

The title compound was prepared from 5-bromo-2,3-diaminopyridine and 4-(2-hydroxyethoxy)benzaldehyde.

$^1$H NMR (DMSO-d$_6$): δ 13.46 (1H, brs); 8.36 (1H, d); 8.19 (1H, brs); 8.15 (2H, d); 7.13 (2H, d); 4.90 (1H, t); 4.08 (2H, t); 3.74 (2H, m). APCI-MS m/z: 334/336 [MH$^+$].

EXAMPLE 20

6-Bromo-2-(3-fluorophenyl)-3H-imidazo[4,5-b]pyridine trifluoroacetate

The title compound was prepared from 5-bromo-2,3-diaminopyridine (0.060 g, 0.3 mmol) and 3-fluorobenzaldehyde (0.037 g, 0.30 mmol). The product was purified by RP-HPLC (10-60% acetonitrile).

$^1$H NMR (CD$_3$OD): δ 8.42 (1H, brs); 8.29 (1H, brs); 8.02 (2H, brd); 7.61 (1H, brd); 7.39 (1H, brd). APCI-MS m/z: 292.0/294.0 [MH$^+$].

EXAMPLE 21

6-Bromo-2-(2-methylphenyl)-3H-imidazo[4,5-b]pyridine trifluoroacetate

The title compound was prepared from 5-bromo-2,3-diaminopyridine (0.060 g, 0.32 mmol) and 2-methylbenzaldehyde (0.036 g, 0.30 mmol).

$^1$H NMR (CD$_3$OD): δ 8.44 (1H, brs); 8.17 (1H, brs); 7.65 (1H, brd); 7.43-7.34 (3H, m); 2.54 (3H, s). APCI-MS m/z: 288.0/290 [MH$^+$].

EXAMPLE 22

6-Bromo-2-(2-methoxyphenyl)-3H-imidazo[4,5-b]pyridine trifluoroacetate

The title compound was prepared from 5-bromo-2,3-diaminopyridine (0.060 g, 0.32 mmol) and 2-methoxybenzaldehyde (0.041 g, 0.30 mmol).

$^1$H NMR (CD$_3$OD): δ 8.52 (1H, brs); 8.22 (1H, brs); 8.16 (1H, brd); 7.62 (1H, t); 7.27 (1H, brd); 7.17 (1H, t); 4.09 (3H, s). APCI-MS m/z: 304.0/306.0 [MH$^+$].

EXAMPLE 23

6-Bromo-2-(4-isopropoxyphenyl)-3H-imidazo[4,5-b]pyridine trifluoroacetate

The title compound was prepared from 5-bromo-2,3-diaminopyridine (0.060 g, 0.32 mmol) and 4-isopropoxybenzaldehyde (0.049 g, 0.30 mmol).

$^1$H NMR (DMSO-d$_6$): δ 8.36 (1H, brs); 8.20 (1H, brs); 8.15 (2H, brd); 7.10 (2H, brd); 4.75 (1H, m); 1.31 (6H, d). APCI-MS m/z: 332.0/334.0 [MH$^+$].

EXAMPLE 24

4-(6-Bromo-3H-imidazo[4,5-b]pyridin-2-yl)benzonitrile trifluoroacetate

The title compound was prepared from 5-bromo-2,3-diaminopyridine (0.060 g, 0.32 mmol) and 4-cyanobenzaldehyde (0.039 g, 0.30 mmol).

$^1$H NMR (DMSO-d$_6$): δ 8.52-8.39 (3H, m); 8.25 (1H, brs); 8.07 (2H, brd). APCI-MS m/z: 299.2/301.0 [MH$^+$].

EXAMPLE 25

2-(6-Bromo-3H-imidazo[4,5-b]pyridin-2-yl)phenol trifluoroacetate

The title compound was prepared from 5-bromo-2,3-diaminopyridine (0.060 g, 0.32 mmol) and salicylaldehyde (0.037 g, 0.30 mmol).

$^1$H NMR (CD$_3$OD): δ 8.49 (1H, brs); 8.21 (1H, brs); 8.14 (1H, brd); 7.45 (1H, t); 7.06 (2H, m). APCI-MS m/z: 290.0/292.0 [MH$^+$].

EXAMPLE 26

6-Bromo-2-(4-isopropylphenyl)-3H-imidazo[4,5-b]pyridine trifluoroacetate

The title compound was prepared from 5-bromo-2,3-diaminopyridine (0.060 g, 0.32 mmol) and 4-isopropylbenzaldehyde (0.044 g, 0.30 mmol).

$^1$H NMR (DMSO-$d_6$): δ 8.40 (1H, brd); 8.25 (1H, brs); 8.15 (2H, brd); 7.46 (2H, brd); 2.98 (1H, m); 1.25 (6H, d). APCI-MS m/z: 316.0/318.0 [MH$^+$].

EXAMPLE 27

6-Bromo-2-(4-methoxyphenyl)-3H-imidazo[4,5-b]pyridine trifluoroacetate

The title compound was prepared from 5-bromo-2,3-diaminopyridine (0.060 g, 0.32 mmol) and 4-methoxybenzaldehyde (0.041 g, 0.30 mmol).

$^1$H NMR (DMSO-$d_6$): δ 8.38 (1H, brs); 8.21 (1H, brs); 8.18 (2H, brd); 7.14 (2H, brd); 3.85 (3H, s). APCI-MS m/z: 304.0/306.0 [MH$^+$].

EXAMPLE 28

6-Bromo-2-(37-methoxyphenyl)-3H-imidazo[4,5-b]pyridine trifluoroacetate

The title compound was prepared from 5-bromo-2,3-diaminopyridine (0.060 g, 0.32 mmol) and 3-methoxybenzaldehyde (0.041 g, 0.30 mmol).

$^1$H NMR (DMSO-$d_6$): δ 8.43 (1H, d); 8.29 (1H, brs); 7.83 (1H, brs); 7.79 (1H, brd); 7.49 (1H, t); 7.13 (1H, brd); 3.87 (3H, s). APCI-MS m/z: 304.0/306.0 [MH$^+$].

EXAMPLE 29

2-[4-(Benzyloxy)-3-methoxyphenyl]-6-bromo-3H-imidazo[4,5-b]pyridine trifluoroacetate The title compound was prepared from 5-bromo-2,3-diaminopyridine (0.060 g, 0.32 mmol) and 4-benzyloxy-3-methoxybenzaldehyde (0.072 g, 0.30 mmol).

$^1$H NMR (CD$_3$OD): δ 8.46 (1H, brd); 8.16 (1H, d); 7.80 (1H, d); 7.71 (1H, dd); 7.48 (2H, brd); 7.42-7.32 (3H, m); 7.21 (2H, d); 5.23 (2H, s); 3.99 (3H, s). APCI-MS m/z: 410.0/412.0 [MH$^+$].

EXAMPLE 30

6-Bromo-2-thien-3-yl-3H-imidazo[4,5-b]pyridine trifluoroacetate

The title compound was prepared from 5-bromo-2,3-diaminopyridine (0.060 g, 0.32 mmol) and 3-thiophenecarboxaldehyde (0.034 g, 0.30 mmol).

$^1$H NMR (CD$_3$OD): δ 8.47 (1H, d); 8.33 (1H, m); 8.18 (1H, d); 7.81 (1H, dd); 7.69 (1H, dd). APCI-MS m/z: 280.2/282.2 [MH$^+$].

EXAMPLE 31

6-Bromo-2-(4-tert-butylphenyl)-1H-imidazo[4,5-b]pyridine trifluoroacetate

The title compound was prepared from 5-bromo-2,3-diaminopyridine and 4-tert-butylbenzaldehyde. APCI-MS m/z: 343.3/345.3 [MH$^+$].

EXAMPLE 32

N-[4-(6-Bromo-3H-imidazo[4,5-b]pyridin-2-yl)phenyl]-N,N-dimethylamine bis(trifluoroacetate)

The title compound was prepared from 5-bromo-2,3-diaminopyridine (0.060 g, 0.32 mmol) and 4-dimethylaminobenzaldehyde (0.045 g, 0.30 mmol).

$^1$H NMR (CD$_3$OD): δ 8.38 (1H, brs); 8.06 (1H, d); 7.97 (2H, brd); 6.88 (2H, brd); 3.09 (6H, s). APCI-MS m/z: 330.3/332.3 [MH$^+$].

EXAMPLE 33

6-Bromo-2-(4-pyrrolidin-1-ylphenyl)-3H-imidazo[4,5-b]pyridine bis(trifluoroacetate)

The title compound was prepared from 5-bromo-2,3-diaminopyridine and 4-(1-pyrrolidino)benzaldehyde.

$^1$H NMR (CD$_3$OD): δ 8.44 (1H, d); 8.11 (1H, d); 7.97 (2H, dd); 6.76 (2H, dd); 3.43 (4H, m); 2.09 (4H, m). APCI-MS m/z: 343.3/345.3 [MH$^+$].

EXAMPLE 34

6-Bromo-2-[4-(methylsulfonyl)phenyl]-3H-imidazo[4,5-b]pyridine trifluoroacetate

The title compound was prepared from 5-bromo-2,3-diaminopyridine (0.060 g, 0.32 mmol) and 4-methylsulphonylbenzaldehyde (0.055 g, 0.30 mmol).

$^1$H NMR (CD$_3$OD): δ 8.59 (1H, dd); 8.20 (1H, dd); 8.02 (4H, s); 3.35 (3H, s). APCI-MS m/z: 352.0/354.0 [MH$^+$].

EXAMPLE 35

N,N-Dimethyl-N-[4-(6-methyl-3H-imidazo[4,5-b]pyridin-2-yl)phenyl]amine bis(trifluoroacetate)

The title compound was prepared from 2,3-diamino-5-methylpyridine (0.037 g, 0.30 mmol) and 4-dimethylaminobenzaldehyde (0.045 g, 0.30 mmol).

$^1$H NMR (CD$_3$OD): δ 8.31 (1H, brs); 8.01 (2H, brd); 7.97 (1H, brs); 6.93 (2H, brd); 3.13 (6H, s); 2.55 (3H, s). APCI-MS m/z: 253.1/254.2 [MH$^+$].

EXAMPLE 36

2-(4-Isopropoxyphenyl)-6-methyl-3H-imidazo[4,5-b]pyridine trifluoroacetate

The title compound was prepared from 2,3-diamino-5-methylpyridine (0.088 g, 0.72 mmol) and 4-isopropoxybenzaldehyde (0.117 g, 0.72 mmol).

$^1$H NMR (CD$_3$OD): δ 8.34 (1H, brs); 8.15 (1H, brs); 8.11 (2H, dd); 7.12 (2H, dd); 4.77 (1H, m); 2.57 (3H, s); 1.38 (6H, d). APCI-MS m/z: 268.0/269.2 [MH$^+$].

EXAMPLE 37

6-Bromo-2-(4-nitrophenyl)-3H-imidazo[4,5-b]pyridine

The title compound was prepared from 5-bromo-2,3-diaminopyridine (0.94 g, 5 mmol) and 4-nitrobenzaldehyde (0.76 g, 5 mmol).

EXAMPLE 38

N-[4-(6-Bromo-3H-imidazo[4,5-b]pyridin-2-yl phenyl]acetamide trifluoro acetate

The title compound was prepared from 5-bromo-2,3-diaminopyridine (0.056 g, 0.30 mmol) and 4-acetamidobenzaldehyde (0.049 g, 0.30 mmol).

$^1$H NMR (DMSO-d$_6$): δ 13.64 (1H, s, NH tautomer); 13.22 (1H, s, NH tautomer); 10.23 (1H, s); 8.32 (1H, brd); 8.15 (2H, brd); 7.76 (2H, brd); 2.10 (3H, s). APCI-MS m/z: 331.1/333.1 [MH$^+$].

EXAMPLE 39

6-Bromo-2-[4-(morpholin-4-ylmethyl)phenyl]-3H-imidazo[4,5-b]pyridine bis(trifluoroacetate)

a) 6-Bromo-2-(4-methylphenyl)-3H-imidazo[4,5-b]pyridine

The title compound was prepared from 5-bromo-2,3-diaminopyridine and 4-methylbenzaldehyde using the method described in Example 1.

$^1$H NMR (DMSO-d$_6$): δ 13.66 (NH-tautomer, s); 13.27 (NH-tautomer, s); 8.37 (1H, brs); 8.28 (1H, brs); 8.10 (2H, d); 7.37 (2H, d); 2.38 (3H, s). APCI-MS m/z: 288/290 [MH$^+$].

b) 6-Bromo-2-[4-(bromomethyl)phenyl]-3H-imidazo[4,5-b]pyridine

The title compound was prepared by refluxing 6-bromo-2-(4-methylphenyl)-3H-imidazo[4,5-b]pyridine with a large excess of bromine in acetic acid overnight. APCI-MS m/z: 366/368/370 [MH$^+$].

c) 6-Bromo-2-[4-(morpholin-4-ylmethyl)phenyl]-3H-imidazo[4,5-b]pyridine bis(trifluoroacetate)

The title compound was prepared by heating 6-bromo-2-[4-(bromomethyl)phenyl]-3H-imidazo[4,5-b]pyridine with an excess of morpholine in NMP at 60° C. for 30 minutes and was purified by RP-HPLC (10-50% acetonitrile).

$^1$H NMR (DMSO-d$_6$): δ 10.37 (1H, brs); 8.90 (1H, brs); 8.44 (1H, d); 8.31 (2H, d); 7.70 (2H, d); 4.42 (2H, s); 4.02-3.60 (4H, dm); 3.34-3.07 (4H, m). APCI-MS m/z: 373.2/375.2 [MH$^+$.

EXAMPLE 40

6-Bromo-2-(6-morpholin-4-ylpyridin-3-yl)-3H-imidazo[4,5-b]pyridine bis(trifluoroacetate)

The title compound was prepared from 6-bromo-2-(6-chloropyridin-3-yl)-3H-imidazo[4,5-b]pyridine and morpholine using the method described in Example 204.

$^1$H NMR (CD$_3$OD): δ 8.88 (1H, d); 8.46 (1H, d); 8.28-8.25 (1H, dd); 8.16 (1H, d); 7.05 (1H, d); 3.82 (4H, t); 3.72 (4H, t). APCI-MS m/z: 360.1/362.0 [MH$^+$].

EXAMPLE 41

2-[4-(6-Bromo-3H-imidazo[4,5-b]pyridin-2-yl)phenoxy]acetamide

To a mixture of 4-(6-bromo-3H-imidazo[4,5-b]pyridin-2-yl)phenol (58 mg, 0.2 mmol) and sodium hydride (55-65%, 18 mg, 0.4 mmol) in DMF (6 ml), 2-chloroacetamide (19 mg, 0.2 mmol) was added and the mixture was heated to 60° C. for 1 h. Column chromatography on silica using ethyl acetate/methanol as eluent afforded the title compound.

$^1$H NMR (DMSO-d$_6$): δ 13.61 (1H, brs); 8.36 (1H, brs); 8.21 (1H, brs); 8.16 (2H, d); 7.58 (1H, brs); 7.42 (1H, brs); 7.13 (2H, d); 4.53 (2H, s). APCI-MS m/z: 347/349 [MH$^+$].

EXAMPLE 42

Ethyl [4-(6-bromo-3H-imidazo[4,5-b]pyridin-2-yl)phenoxy]acetate

The title compound was prepared from 4-(6-bromo-3H-imidazo[4,5-b]pyridin-2-yl)phenol and ethyl chloroacetate using the method described in Example 41.

$^1$H NMR (DMSO-d$_6$): δ 13.48 (1H, brs); 8.36 (1H, d); 8.21 (1H, brs); 8.15 (2H, d); 7.12 (2H, d); 4.89 (2H, s); 4.18 (2H, q); 1.21 (3H, t). APCI-MS m/z: 376/378 [MH$^+$].

EXAMPLE 43

N-(2-[4-(6-Bromo-3H-imidazo[4,5-b]pyridin-2-yl)phenoxy]ethyl}-N-methylamine

The title compound was prepared from 4-(6-bromo-3H-imidazo[4,5-b]pyridin-2-yl)phenol and tert-butyl 2-bromoethyl(methyl)carbamate using the method described in Example 41, followed by deprotection using trifluoroacetic acid.

$^1$H NMR (DMSO-d$_6$): δ 8.35 (1H, s); 8.19 (1H, s); 8.15 (2H, d); 7.12 (2H, d); 4.11 (2H, t); 3.31 (2H(NH), brs); 2.87 (2H, t); 2.35 (3H, s). APCI-MS m/z: 347/349 [MH$^+$].

EXAMPLE 44

6-Bromo-2-[4-(3-chloropropoxy)phenyl]-3H-imidazo[4,5-b]pyridine

The title compound was prepared from 4-(6-bromo-3H-imidazo[4,5-b]pyridin-2-yl)phenol and 1-bromo-3-chloropropane using the method described in Example 41.

$^1$H NMR (DMSO-d$_6$): δ 13.58 (1H, brs); 8.35 (1H, brs); 8.22 (1H, brs); 8.15 (2H, d); 7.14 (2H, d); 4.18 (2H, t); 3.80 (2H, t); 2.19 (2H, qv). APCI-MS m/z: 365.9/367.9 [MH$^+$].

EXAMPLE 45

3-[4-(6-Bromo-3H-imidazo[4,5-b]pyridin-2-yl)phenoxy]propan-1-amine a) 2-{3-[4-(6-Bromo-3H-imidazo[4,5-b]pyridin-2-yl)phenoxy]propyl}-1H-isoindole-1.3 (2H)-dione The title compound was prepared from 4-(6-bromo-3H-imidazo[4,5-b]pyridin-2-yl)phenol and 2-(3-bromopropyl)-1H-isoindole-1,3 (2H)-dione using the method described in Example 41.

$^1$H NMR (DMSO-d$_6$): δ 13.40 (1H, brs); 8.34 (1H, d); 8.17 (1H, d); 8.10 (2H, d); 7.88-7.80 (4H, m); 6.96 (2H, d); 4.11 (2H, t); 3.77 (2H, t); 2.08 (2H, qv). APCI-MS m/z: 477/479 [MH$^+$].

The preceding page's $^1$H NMR (DMSO-d$_6$): δ 8.49 (1H, d); 8.44 (4H, dd); 8.37 (1H, d). APCI-MS m/z: 319.0/321.0 [MH$^+$].

b) 3-[4-(6-Bromo-3H-imidazo[4,5-b]pyridin-2-yl)phenoxy]propan-1-amine

The title compound was prepared by stirring 2-{3-[4-(6-bromo-3H-imidazo[4,5-b]pyridin-2-yl)phenoxy]propyl}-1H-isoindole-1,3(2H)-dione with a large excess of methylamine in ethanol for two days and was purified by column chromatography on silica.

$^1$H NMR (DMSO-d$_6$): δ 8.30 (1H, d); 8.15 (2H, d); 8.13 (1H, d); 7.09 (2H, d); 5.76 (2H, brs); 4.12 (2H, (NH2), t); 3.42 (1H, (NH), brs); 2.73 (2H, t); 1.83 (2H, qv). APCI-MS m/z: 347/349 [MH$^+$].

EXAMPLE 46

6-Bromo-2-[4-(3-morpholin-4-ylpropoxy)phenyl]-3H-imidazo[4,5-b]pyridine

A solution of 6-bromo-2-[4-(3-chloropropoxy)phenyl]-3H-imidazo[4,5-b]pyridine (50 mg, 0.14 mmol), lithium iodide (20 mg, 0.15 mmol) and morpholine (0.1 ml, 1.15 mmol) in DMF (5 ml) was heated at 100° C. for 6 h. Column chromatography on silica using methylene chloride/methanol/ammonia as eluent afforded the title compound in almost quantitative yield.

$^1$H NMR (DMSO-d$_6$): δ 13.10 (1H, brs); 8.34 (1H, d); 8.17 (1H, d); 8.14 (2H, d); 7.11 (2H, d); 4.10 (2H, t); 3.56 (4H, t); 2.42 (2H, t); 2.36 (4H, brm); 1.89 (2H, qv). APCI-MS m/z: 417/419 [MH$^+$].

EXAMPLE 47

6-Bromo-2-[4-(3-piperidin-1-ylpropoxy)phenyl]-3H-imidazo[4,5-b]pyridine

The title compound was prepared from 6-bromo-2-[4-(3-chloropropoxy)phenyl]-3H-imidazo[4,5-b]pyridine and piperidine using the method described in Example 46.

$^1$H NMR (DMSO-d$_6$): δ 13.45 (1H, brs); 8.35 (1H, d); 8.18 (1H, brs); 8.14 (2H, d); 7.11 (2H, d); 4.08 (2H, t); 2.38 (2H, t); 2.32 (4H, brm); 1.87 (2H, qv); 1.48 (4H, qv); 1.37 (2H, m). APCI-MS m/z: 415.1/417.1 [MH$^+$].

EXAMPLE 48

6-Bromo-2-[4-(3-pyrrolidin-1-ylpropoxy)phenyl]-3H-imidazo[4,5-b]pyridine

The title compound was prepared from 6-bromo-2-[4-(3-chloropropoxy)phenyl]-3H-imidazo[4,5-b]pyridine and pyrrolidine using the method described in Example 46.

$^1$H NMR (DMSO-d$_6$): δ 13.22 (1H, brs); 8.35 (1H, d); 8.19 (1H, brs); 8.15 (2H, d); 7.11 (2H, d); 4.11 (2H, t); 2.61 (2H, t); 2.53 (4H, m); 1.93 (2H, qv); 1.70 (4H, m). APCI-MS m/z: 401.1/403.1 [MH$^+$].

EXAMPLE 49

6-Bromo-2-[4-(2-chloroethoxy)phenyl]-3H-imidazo[4,5-b]pyridine

2-[4-(6-Bromo-3H-imidazo[4,5-b]pyridin-2-yl)phenoxy]ethanol (2.0 g, 6 mmol) was dissolved and refluxed in thionyl chloride (30 ml) for 3 h. The excess thionyl chloride was evaporated off and the residue was co-evaporated twice with toluene affording the title product in quantitative yield.

$^1$H NMR (DMSO-d$_6$): δ 13.60 (NH-tautomer, s); 13.20 (NH-tautomer, s); 8.34 (1H, d); 8.25 (1H, brs); 8.16 (2H, d); 7.15 (2H, d); 4.35 (2H, t); 3.97 (2H, t). APCI-MS m/z: 351.9/353.9 [MH$^+$].

EXAMPLE 50

6-Bromo-2-[4-(2-morpholin-4-ylethoxy)phenyl]-3H-imidazo[4,5-b]pyridine

A solution of 6-bromo-2-[4-(2-chloroethoxy)phenyl]-3H-imidazo[4,5-b]pyridine (50 mg, 0.14 mmol), morpholine (0.037 ml, 0.42 mmol) in NMP (5 ml) and N-ethyldiisopropylamine (0.24 ml, 1.4 mmol) was heated at 120° C. for 6 h. Column chromatography on silica using methylene chloride/methanol/ammonia as eluent afforded the title compound.

$^1$H NMR (DMSO-d$_6$): δ 13.58 (NH-tautomer, brs); 13.18 (NH-tautomer, brs); 8.33 (1H, m); 8.25 (1H, m); 8.15 (2H, m); 7.13 (2H, m); 4.18 (2H, t); 3.57 (4H, m); 2.72 (2H, m); 2.49 (4H, m). APCI-MS m/z: 403/405 (MH$^+$).

Using the general method of Example 50, the compounds of Examples 51 to 119 were prepared:

EXAMPLE 51

N-{2-[4-(6-Bromo-3H-imidazo[4,5-b]pyridin-2-yl)phenoxy]ethyl}-N-(tetrahydrofuran-2-ylmethyl)amine The title compound was prepared from 6-bromo-2-[4-(2-chloroethoxy)phenyl]-3H-imidazo[4,5-b]pyridine and tetrahydrofurfurylamine.

$^1$H NMR (DMSO-d$_6$): δ 13.30 (1H, brs); 8.36 (1H, s); 8.22 (1H, brs); 8.15 (2H, d); 7.13 (2H, d); 4.13 (2H, t); 3.88 (1H, m); 3.73 (1H, m); 3.60 (1H, m); 2.95 (2H, t); 2.65 (2H, m); 1.89 (1H, m); 1.79 (2H, m); 1.51 (1H, m). APCI-MS m/z: 417.1/419.1 [MH$^+$].

EXAMPLE 52

6-Bromo-2-[4-(2-pyrrolidin-1-ylethoxy)phenyl]-3H-imidazo[4,5-b]pyridine bis(trifluoroacetate)

The title compound was prepared from 6-bromo-2-[4-(2-chloroethoxy)phenyl]-3H-imidazo[4,5-b]pyridine and pyrrolidine.

APCI-MS m/z: 387.4/389.4 [MH$^+$].

EXAMPLE 53

2-[{2-[4-(6-Bromo-3H-imidazo[4,5-b]pyridin-2-yl)phenoxy]ethyl}(methyl)amino]ethanol bis(trifluoroacetate)

The title compound was prepared from 6-bromo-2-[4-(2-chloroethoxy)phenyl]-3H-imidazo[4,5-b]pyridine and 2-(methylamino)ethanol.

APCI-MS m/z: 391.4/393.4 [MH$^+$].

EXAMPLE 54

3-[{2-[4-(6-Bromo-3H-imidazo[4,5-b]pyridin-2-yl)phenoxy]ethyl}(methyl)amino]propanenitrile bis(trifluoroacetate)

The title compound was prepared from 6-bromo-2-[4-(2-chloroethoxy)phenyl]-3H-imidazo[4,5-b]pyridine and 3-(methylamino)propanenitrile.

APCI-MS m/z: 400.3/402.4 [MH$^+$].

EXAMPLE 55

6-Bromo-2-[4-(2-morpholin-4-ylethoxy)phenyl]-3H-imidazo[4,5-b]pyridine bis(trifluoroacetate)

The title compound was prepared from 6-bromo-2-[4-(2-chloroethoxy)phenyl]-3H-imidazo[4,5-b]pyridine and morpholine.
APCI-MS m/z: 403.4/405.4 [MH$^+$].

EXAMPLE 56

1-{2-[4-(6-Bromo-3H-imidazo[4,5-b]pyridin-2-yl)phenoxy]ethyl}pyrrolidin-3-ol bis(trifluoroacetate)

The title compound was prepared from 6-bromo-2-[4-(2-chloroethoxy)phenyl]-3H-imidazo[4,5-b]pyridine and pyrrolidin-3-ol.
APCI-MS m/z: 403.4/405.4 [MH$^+$].

EXAMPLE 57

6-Bromo-2-{4-[2-(4-methylpiperazin-1-yl)ethoxy]phenyl}-3H-imidazo[4,5-b]pyridine bis(trifluoroacetate)

The title compound was prepared from 6-bromo-2-[4-(2-chloroethoxy)phenyl]-3H-imidazo[4,5-b]pyridine and 1-methylpiperazine.
APCI-MS m/z: 416.4/418.4 [MH$^+$].

EXAMPLE 58

1-{2-[4-(6-Bromo-3H-imidazo[4,5-b]pyridin-2-yl)phenoxy]ethyl}-N,N-dimethylpyrrolidin-3-amine bis(trifluoroacetate)

The title compound was prepared from 6-bromo-2-[4-(2-chloroethoxy)phenyl]-3H-imidazo[4,5-b]pyridine and N,N-dimethylpyrrolidin-3-amine.
APCI-MS m/z: 430.4/432.4 [MH$^+$].

EXAMPLE 59

N-{2-[4-(6-Bromo-3H-imidazo[4,5-b]pyridin-2-yl)phenoxy]ethyl}-N,1-dimethylpyrrolidin-3-amine bis(trifluoroacetate)

The title compound was prepared from 6-bromo-2-[4-(2-chloroethoxy)phenyl]-3H-imidazo[4,5-b]pyridine and N,1-dimethylpyrrolidin-3-amine.
APCI-MS m/z: 430.4/432.4 [MH$^+$].

EXAMPLE 60

N$^2$-{2-[4-(6-Bromo-3H-imidazo[4,5-b]pyridin-2-yl)phenoxy]ethyl}-N$^1$,N$^1$,N$^2$-trimethylglycinamide bis(trifluoroacetate)

The title compound was prepared from 6-bromo-2-[4-(2-chloroethoxy)phenyl]-3H-imidazo[4,5-b]pyridine and N$^1$,N$^1$,N$^2$-trimethylglycinamide.
APCI-MS m/z: 432.4/434.4 [MH$^+$].

EXAMPLE 61

N-{2-[4-(6-Bromo-3H-imidazo[4,5-b]pyridin-2-yl)phenoxy]ethyl}-N-ethyl-N',N'-dimethylethane-1,2-diamine bis(trifluoroacetate)

The title compound was prepared from 6-bromo-2-[4-(2-chloroethoxy)phenyl]-3H-imidazo[4,5-b]pyridine and N'-ethyl-N,N-dimethylethane-1,2-diamine.
APCI-MS m/z: 432.4/434.4 [MH$^+$].

EXAMPLE 62

N-Benzyl-N-{2-[4-(6-bromo-3H-imidazo[4,5-b]pyridin-2-yl)phenoxy]ethyl}-N-methylamine bis(trifluoroacetate)

The title compound was prepared from 6-bromo-2-[4-(2-chloroethoxy)phenyl]-3H-imidazo[4,5-b]pyridine and N-benzyl-N-methylamine.
APCI-MS m/z: 437.4/439.4 [MH$^+$].

EXAMPLE 63

2-{4-[2-(4-Acetylpiperazin-1-yl)ethoxy]phenyl}-6-bromo-3H-imidazo[4,5-b]pyridine bis(trifluoroacetate)

The title compound was prepared from 6-bromo-2-[4-(2-chloroethoxy)phenyl]-3H-imidazo[4,5-b]pyridine and 1-acetylpiperazine.
APCI-MS m/z: 444.4/446.4 (MH$^+$].

EXAMPLE 64

N-{2-[4-(6-Bromo-3H-imidazo[4,5-b]pyridin-2-yl)phenoxy]ethyl}-N,N-bis(2-methoxyethyl)amine bis(trifluoroacetate)

The title compound was prepared from 6-bromo-2-[4-(2-chloroethoxy)phenyl]-3H-imidazo[4,5-b]pyridine and N,N-bis(2-methoxyethyl)amine.
APCI-MS m/z: 449.5/451.5 [MH$^+$].

EXAMPLE 65

N-{2-[4-(6-Bromo-3H-imidazo[4,5-b]pyridin-2-yl)phenoxy]ethyl}-N-methyl-N-(2-phenylethyl)amine bis(trifluoroacetate)

The title compound was prepared from 6-bromo-2-[4-(2-chloroethoxy)phenyl]-3H-imidazo[4,5-b]pyridine and N-methyl-N-(2-phenylethyl)amine.
APCI-MS m/z: 451.5/453.41 [MH$^+$].

EXAMPLE 66

6-Bromo-2-{4-[2-(4-phenylpiperazin-1-yl)ethoxy]phenyl}-3H-imidazo[4,5-b]pyridine bis(trifluoroacetate)

The title compound was prepared from 6-bromo-2-[4-(2-chloroethoxy)phenyl]-3H-imidazo[4,5-b]pyridine and 1-phenylpiperazine.
APCI-MS m/z: 478.5/480.5 [MH$^+$].

EXAMPLE 67

6-Bromo-2-{4-[2-(4-pyridin-2-ylpiperazin-1-yl)ethoxy]phenyl}-3H-imidazo[4,5-b]pyridine bis(trifluoroacetate)

The title compound was prepared from 6-bromo-2-(4-(2-chloroethoxy)phenyl]-3H-imidazo[4,5-b]pyridine and 1-pyridin-2-ylpiperazine.
APCI-MS m/z: 479.4/481.4 [MH$^+$].

EXAMPLE 68

N-{2-[4-(6-Bromo-3H-imidazo[4,5-b]pyridin-2-yl)phenoxy]ethyl}-N-[3-(1H-imidazol-1-yl)propyl]amine bis(trifluoroacetate)

The title compound was prepared from 6-bromo-2-[4-(2-chloroethoxy)phenyl]-3H-imidazo[4,5-b]pyridine and 3-(1H-imidazol-1-yl)propan-1-amine.
APCI-MS m/z: 441.4/443.4 [MH$^+$].

EXAMPLE 69

N-{2-[4-(6-Bromo-3H-imidazo[4,5-b]pyridin-2-yl)phenoxy]ethyl}-N-(4-methoxybenzyl)amine bis(trifluoroacetate)

The title compound was prepared from 6-bromo-2-[4-(2-chloroethoxy)phenyl]-3H-imidazo[4,5-b]pyridine and 4-methoxybenzylamine.
APCI-MS m/z: 453.4/455.5 [MH$^+$].

EXAMPLE 70

N-{2-[4-(6-Bromo-3H-imidazo[4,5-b]pyridin-2-yl)phenoxy]ethyl}-N-(3-methoxybenzyl)amine bis(trifluoroacetate)

The title compound was prepared from 6-bromo-2-[4-(2-chloroethoxy)phenyl]-3H-imidazo[4,5-b]pyridine and 3-methoxybenzylamine.
APCI-MS m/z: 453.4/455.5 [MH$^+$].

EXAMPLE 71

N-{2-[4-(6-Bromo-3H-imidazo[4,5-b]pyridin-2-yl)phenoxy]ethyl}-N-(4-chlorobenzyl)amine bis(trifluoroacetate)

The title compound was prepared from 6-bromo-2-[4-(2-chloroethoxy)phenyl]-3H-imidazo[4,5-b]pyridine and 4-chlorobenzylamine.
APCI-MS m/z: 457.4/459.4 [MH$^+$].

EXAMPLE 72

N-{2-[4-(6-Bromo-3H-imidazo[4,5-b]pyridin-2-yl)phenoxy]ethyl}-N-(3-chlorobenzyl)amine bis(trifluoroacetate)

The title compound was prepared from 6-bromo-2-[4-(2-chloroethoxy)phenyl]-3H-imidazo[4,5-b]pyridine and 3-chlorobenzylamine.
APCI-MS m/z: 457.3/459.4 [MH$^+$].

EXAMPLE 73

Ethyl 4-({2-[4-(6-bromo-3H-imidazo[4,5-b]pyridin-2-yl)phenoxy]ethyl}amino)piperidine-1-carboxylate bis(trifluoroacetate)

The title compound was prepared from 6-bromo-2-[4-(2-chloroethoxy)phenyl]-3H-imidazo[4,5-b]pyridine and ethyl 4-aminopiperidine-1-carboxylate.
APCI-MS m/z: 488.5/490.5 [MH$^+$].

EXAMPLE 74

6-Bromo-2-(4-{2-[4-(2-methoxyethyl)piperazin-1-yl]ethoxy}phenyl)-3H-imidazo[4,5-b]pyridine bis(trifluoroacetate)

The title compound was prepared from 6-bromo-2-[4-(2-chloroethoxy)phenyl]-3H-imidazo[4,5-b]pyridine and 1-(2-methoxyethyl)piperazine.
APCI-MS m/z: 460.5/462.5 [MH$^+$].

EXAMPLE 75

1-({2-[4-(6-Bromo-3H-imidazo[4,5-b]pyridin-2-yl)phenoxy]ethylamino)propan-2-ol bis(trifluoroacetate)

The title compound was prepared from 6-bromo-2-[4-(2-chloroethoxy)phenyl]-3H-imidazo[4,5-b]pyridine and 1-amino-2-propanol.
APCI-MS m/z: 391.4/393.4 [MH$^+$].

EXAMPLE 76

N-{2-[4-(6-Bromo-3H-imidazo[4,5-b]pyridin-2-yl)phenoxy]ethyl}-N-(2-methoxyethyl)amine bis(trifluoroacetate)

The title compound was prepared from 6-bromo-2-[4-(2-chloroethoxy)phenyl]-3H-imidazo[4,5-b]pyridine and 2-methoxyethylamine.
APCI-MS m/z: 391.4/393.3 [MH$^+$].

EXAMPLE 77

2-({2-[4-(6-Bromo-3H-imidazo[4,5-b]pyridin-2-yl)phenoxy]ethyl}amino)propan-1-ol bis(trifluoroacetate)

The title compound was prepared from 6-bromo-2-[4-(2-chloroethoxy)phenyl]-3H-imidazo[4,5-b]pyridine and DL-2-aminopropan-1-ol.
APCI-MS m/z: 391.4/393.3 [MH$^+$].

EXAMPLE 78

N-{2-[4-(6-Bromo-3H-imidazo[4,5-b]pyridin-2-yl)phenoxy]ethyl}-N-(2-furylmethyl)amine bis(trifluoroacetate)

The title compound was prepared from 6-bromo-2-[4-(2-chloroethoxy)phenyl]-3H-imidazo[4,5-b]pyridine and furfurylamine.
APCI-MS m/z: 413.4/415.4 [MH$^+$].

EXAMPLE 79

N-{2-[4-(6-Bromo-3H-imidazo[4,5-b]pyridin-2-yl)phenoxy]ethyl}-N-(tetrahydrofuran-2-ylmethyl)amine bis(trifluoroacetate)

The title compound was prepared from 6-bromo-2-[4-(2-chloroethoxy)phenyl]-3H-imidazo[4,5-b]pyridine and tetrahydrofurfurylamine.
APCI-MS m/z: 417.4/419.4 [MH$^+$].

EXAMPLE 80

N-Benzyl-N-{2-[4-(6-bromo-3H-imidazo[4,5-b]pyridin-2-yl)phenoxy]ethyl}amine bis(trifluoroacetate)

The title compound was prepared from 6-bromo-2-[4-(2-chloroethoxy)phenyl]-3H-imidazo[4,5-b]pyridine and benzylamine.
APCI-MS m/z: 423.4/425.4 [MH$^+$].

EXAMPLE 81

N-{2-[4-(6-Bromo-3H-imidazo[4,5-b]pyridin-2-yl)phenoxy]ethyl}-N-(pyridin-3-ylmethyl)amine bis(trifluoroacetate)

The title compound was prepared from 6-bromo-2-[4-(2-chloroethoxy)phenyl]-3H-imidazo[4,5-b]pyridine and 1-pyridin-3-ylmethanamine.
APCI-MS m/z: 424.4/426.4 [MH$^+$].

EXAMPLE 82

N-{2-[4-(6-Bromo-3H-imidazo[4,5-b]pyridin-2-yl)phenoxy]ethyl}-N-(pyridin-4-ylmethyl)amine bis(trifluoroacetate)

The title compound was prepared from 6-bromo-2-[4-(2-chloroethoxy)phenyl]-3H-imidazo[4,5-b]pyridine and 1-pyridin-4-ylmethanamine.
APCI-MS m/z: 424.4/426.4 [MH$^+$].

EXAMPLE 83

N-{2-[4-(6-Bromo-3H-imidazo[4,5-b]pyridin-2-yl)phenoxy]ethyl}-N-(thien-2-ylmethyl)amine bis(trifluoroacetate)

The title compound was prepared from 6-bromo-2-[4-(2-chloroethoxy)phenyl]-3H-imidazo[4,5-b]pyridine and 1-thien-2-ylmethanamine.
APCI-MS m/z: 429.3/431.3 [MH$^+$].

EXAMPLE 84

N-{2-[4-(6-Bromo-3H-imidazo[4,5-b]pyridin-2-yl)phenoxy]ethyl}-N-(1-phenylethyl)amine bis(trifluoroacetate)

The title compound was prepared from 6-bromo-2-[4-(2-chloroethoxy)phenyl]-3H-imidazo[4,5-b]pyridine and D,L-1-phenylethylamine.
APCI-MS m/z: 437.4/439.4 [MH$^+$].

EXAMPLE 85

N-{2-[4-(6-Bromo-3H-imidazo[4,5-b]pyridin-2-yl)phenoxy]ethyl}-1-ethylpiperidin-3-amine bis(trifluoroacetate)

The title compound was prepared from 6-bromo-2-[4-(2-chloroethoxy)phenyl]-3H-imidazo[4,5-b]pyridine and 1-ethylpiperidin-3-amine.
APCI-MS m/z: 444.5/446.5 [MH$^+$].

EXAMPLE 86

N-{2-[4-(6-Bromo-3H-imidazo[4,5-b]pyridin-2-yl)phenoxy]ethyl}-N-(2-morpholin-4-ylethyl)amine bis(trifluoroacetate)

The title compound was prepared from 6-bromo-2-[4-(2-chloroethoxy)phenyl]-3H-imidazo[4,5-b]pyridine and 2-morpholin-4-ylethanamine.
APCI-MS m/z: 446.4/448.4 [MH$^+$].

EXAMPLE 87

N-{2-[4-(6-Bromo-3H-imidazo[4,5-b]pyridin-2-yl)phenoxy]ethyl}-N-(2-methoxybenzyl)amine bis(trifluoroacetate)

The title compound was prepared from 6-bromo-2-[4-(2-chloroethoxy)phenyl]-3H-imidazo[4,5-b]pyridine and 2-methoxybenzylamine.
APCI-MS m/z: 453.4/455.4 [MH$^+$].

EXAMPLE 88

1-[3-({2-[4-(6-Bromo-3H-imidazo[4,5-b]pyridin-2-yl)phenoxy]ethyl amino)propyl]pyrrolidin-2-one bis(trifluoroacetate)

The title compound was prepared from 6-bromo-2-[4-(2-chloroethoxy)phenyl]-3H-imidazo[4,5-b]pyridine and 1-(3-aminopropyl)pyrrolidin-2-one.
APCI-MS m/z: 458.5/460.4 [MH$^+$].

EXAMPLE 89

N-{2-[4-(6-Bromo-3H-imidazo[4,5-b]pyridin-2-yl)phenoxy]ethyl}-N-[2-(4-chlorophenyl)ethyl]amine bis(trifluoroacetate)

The title compound was prepared from 6-bromo-2-[4-(2-chloroethoxy)phenyl]-3H-imidazo[4,5-b]pyridine and 2-(4-chlorophenyl)ethanamine.
APCI-MS m/z: 471.4/473.4 [MH$^+$].

EXAMPLE 90

4-[{2-[4-(6-Bromo-3H-imidazo[4,5-b]pyridin-2-yl)phenoxy]ethyl}(methyl)amino]cyclohexanecarbonitrile bis(trifluoroacetate)

The title compound was prepared from 6-bromo-2-[4-(2-chloroethoxy)phenyl]-3H-imidazo[4,5-b]pyridine and 4-(methylamino)cyclohexanecarbonitrile.
APCI-MS m/z: 454.4/456.4 [MH$^+$].

EXAMPLE 91

1-{2-[4-(6-Bromo-3H-imidazo[4,5-b]pyridin-2-yl)phenoxy]ethyl}piperidin-3-ol bis(trifluoroacetate)

The title compound was prepared from 6-bromo-2-[4-(2-chloroethoxy)phenyl]-3H-imidazo[4,5-b]pyridine and piperidin-3-ol.
APCI-MS m/z: 417.4/419.4 [MH$^+$].

EXAMPLE 92

6-Bromo-2-4-[2-(2-pyridin-3-ylpiperidin-1-yl)ethoxy]phenyl}-3H-imidazo[4,5-b]pyridine bis(trifluoroacetate)

The title compound was prepared from 6-bromo-2-[4-(2-chloroethoxy)phenyl]-3H-imidazo[4,5-b]pyridine and 3-piperidin-2-ylpyridine.
APCI-MS m/z: 478.4/480.5 [MH$^+$].

EXAMPLE 93

N-{2-[4-(6-Bromo-3H-imidazo[4,5-b]pyridin-2-yl)phenoxy]ethyl}-N-cyclopentylamine bis(trifluoroacetate)

The title compound was prepared from 6-bromo-2-[4-(2-chloroethoxy)phenyl]-3H-imidazo[4,5-b]pyridine and cyclopentylamine.
APCI-MS m/z: 401.4/403.4 [MH$^+$].

EXAMPLE 94

1-{2-[4-(6-Bromo-3H-imidazo[4,5-b]pyridin-2-yl)phenoxy]ethyl}-4-phenylpiperidin-4-ol bis(trifluoroacetate)

The title compound was prepared from 6-bromo-2-[4-(2-chloroethoxy)phenyl]-3H-imidazo[4,5-b]pyridine and 4-phenylpiperidin-4-ol.
APCI-MS m/z: 493.5/495.5 [MH$^+$].

EXAMPLE 95

N-{2-[4-(6-Bromo-3H-imidazo[4,5-b]pyridin-2-yl)phenoxy]ethyl}-N-[2-(1H-imidazol-4-yl)ethyl]amine bis(trifluoroacetate)

The title compound was prepared from 6-bromo-2-[4-(2-chloroethoxy)phenyl]-3H-imidazo[4,5-b]pyridine and 2-(1H-imidazol-4-yl)ethanamine dihydrochloride.
APCI-MS m/z: 427.4/429.4 [MH$^+$].

EXAMPLE 96

1-{2-[4-(6-Bromo-3H-imidazo[4,5-b]pyridin-2-yl)phenoxy]ethyl}piperidine-3-carboxamide bis(trifluoroacetate)

The title compound was prepared from 6-bromo-2-[4-(2-chloroethoxy)phenyl]-3H-imidazo[4,5-b]pyridine and piperidine-3-carboxamide.
APCI-MS m/z: 444.4/446.4 [MH$^+$].

EXAMPLE 97

6-Bromo-2-{4-[2-(4-pyrazin-2-ylpiperazin-1-yl)ethoxy]phenyl}-3H-imidazo[4,5-b]pyridine bis(trifluoroacetate)

The title compound was prepared from 6-bromo-2-[4-(2-chloroethoxy)phenyl]-3H-imidazo[4,5-b]pyridine and 2-piperazin-1-ylpyrazine.
APCI-MS m/z: 480.5/482.4 [MH$^+$].

EXAMPLE 98

(1S,2S)-2-({2-[4-(6-Bromo-3H-imidazo[4,5-b]pyridin-2-yl)phenoxy]ethyl amino)cyclohexanol bis(trifluoroacetate)

The title compound was prepared from 6-bromo-2-[4-(2-chloroethoxy)phenyl]-3H-imidazo[4,5-b]pyridine and (1S,2S)-2-aminocyclohexanol hydrochloride.
APCI-MS m/z: 431.4/433.4 [MH$^+$].

EXAMPLE 99

6-Bromo-2-(4-2-[4-(3-methoxyphenyl)piperazin-1-yl]ethoxy phenyl)-3H-imidazo[4,5-b]pyridine bis(trifluoroacetate)

The title compound was prepared from 6-bromo-2-[4-(2-chloroethoxy)phenyl]-3H-imidazo[4,5-b]pyridine and 1-(3-methoxyphenyl)piperazine.
APCI-MS m/z: 508.5/510.5 [MH$^+$].

EXAMPLE 100

(1-2-[4-(6-Bromo-3H-imidazo[4,5-b]pyridin-2-yl)phenoxy]ethyl}piperidin-4-yl)methanol bis(trifluoroacetate)

The title compound was prepared from 6-bromo-2-[4-(2-chloroethoxy)phenyl]-3H-imidazo[4,5-b]pyridine and piperidin-4-ylmethanol.
APCI-MS m/z: 431.4/433.4 [MH$^+$].

EXAMPLE 101

4-({2-[4-(6-Bromo-3H-imidazo[4,5-b]pyridin-2-yl)phenoxy]ethyl}amino)cyclohexanol bis(trifluoroacetate)

The title compound was prepared from 6-bromo-2-[4-(2-chloroethoxy)phenyl]-3H-imidazo[4,5-b]pyridine and 4-aminocyclohexanol hydrochloride.
APCI-MS m/z: 431.4/433.4 [MH$^+$].

EXAMPLE 102

(1-{2-[4-(6-Bromo-3H-imidazo[4,5-b]pyridin-2-yl)phenoxy]ethyl}piperidin-2-yl)methanol bis(trifluoroacetate)

The title compound was prepared from 6-bromo-2-[4-(2-chloroethoxy)phenyl]-3H-imidazo[4,5-b]pyridine and piperidin-2-ylmethanol.
APCI-MS m/z: 431.4/433.4 [MH$^+$].

EXAMPLE 103

1'-{2-[4-(6-Bromo-3H-imidazo[4,5-b]pyridin-2-yl)phenoxy]ethyl 1-1,4'-bipiperidine bis(trifluoroacetate)

The title compound was prepared from 6-bromo-2-[4-(2-chloroethoxy)phenyl]-3H-imidazo[4,5-b]pyridine and 1,4'-bipiperidine.
APCI-MS m/z: 484.5/486.5 [MH$^+$].

EXAMPLE 104

N-{2-[4-(6-Bromo-3H-imidazo[4,5-b]pyridin-2-yl)phenoxy]ethyl}-1,3-thiazol-2-amine bis(trifluoroacetate)

The title compound was prepared from 6-bromo-2-[4-(2-chloroethoxy)phenyl]-3H-imidazo[4,5-b]pyridine and 2-aminothiazole.
APCI-MS m/z: 416.3/418.3 [MH$^+$].

EXAMPLE 105

1-{2-[4-(6-Bromo-3H-imidazo[4,5-b]pyridin-2-yl)phenoxy]ethyl}piperidine-4-carboxamide bis(trifluoroacetate)

The title compound was prepared from 6-bromo-2-[4-(2-chloroethoxy)phenyl]-3H-imidazo[4,5-b]pyridine and piperidine-4-carboxamide.
APCI-MS m/z: 444.4/446.4 [MH$^+$].

EXAMPLE 106

N-{2-[4-(6-Bromo-3H-imidazo[4,5-b]pyridin-2-yl)phenoxy]ethyl}-1H-1,2,4-triazol-3-amine bis(trifluoroacetate)

The title compound was prepared from 6-bromo-2-[4-(2-chloroethoxy)phenyl]-3H-imidazo[4,5-b]pyridine and 1H-1,2,4-triazol-3-amine.
APCI-MS m/z: 400.3/402.3 [MH$^+$].

EXAMPLE 107

2-(4-{2-[4-(6-Bromo-3H-imidazo[4,5-b]pyridin-2-yl)phenoxy]ethyl}piperazin-1-yl)benzonitrile bis(trifluoroacetate)

The title compound was prepared from 6-bromo-2-[4-(2-chloroethoxy)phenyl]-3H-imidazo[4,5-b]pyridine and 2-piperazin-1-ylbenzonitrile.
APCI-MS m/z: 503.5/505.5 [MH$^+$].

EXAMPLE 108

6-(4-{2-[4-(6-Bromo-3H-imidazo[4,5-b]pyridin-2-yl)phenoxy]ethyl}piperazin-1-yl)nicotinonitrile bis(trifluoroacetate)

The title compound was prepared from 6-bromo-2-[4-(2-chloroethoxy)phenyl]-3H-imidazo[4,5-b]pyridine and 6-piperazin-1-ylnicotinonitrile.
APCI-MS m/z: 504.5/506.5 [MH$^+$].

EXAMPLE 109

1-{2-[4-(6-Bromo-3H-imidazo[4,5-b]pyridin-2-yl)phenoxy]ethyl}prolinamide bis(trifluoroacetate)

The title compound was prepared from 6-bromo-2-[4-(2-chloroethoxy)phenyl]-3H-imidazo[4,5-b]pyridine and D-prolinamide.
APCI-MS m/z: 430.4/432.4 [MH$^+$].

EXAMPLE 110

6-Bromo-2-(4-2-[4-(2-methoxyphenyl)piperidin-1-yl]ethoxy}phenyl)-3H-imidazo[4,5-b]pyridine bis(trifluoroacetate)

The title compound was prepared from 6-bromo-2-[4-(2-chloroethoxy)phenyl]-3H-imidazo[4,5-b]pyridine and 4-(2-methoxyphenyl)piperidine.
APCI-MS m/z: 507.5/509.5 [MH$^+$].

EXAMPLE 111

2-(4-{2-[4-(6-Bromo-3H-imidazo[4,5-b]pyridin-2-yl)phenoxy]ethyl}piperazin-1-yl)ethanol bis(trifluoroacetate)

The title compound was prepared from 6-bromo-2-[4-(2-chloroethoxy)phenyl]-3H-imidazo[4,5-b]pyridine and 2-piperazin-1-ylethanol.
APCI-MS m/z: 446.4/448.4 [MH$^+$].

EXAMPLE 112

1-{2-[4-(6-Bromo-3H-imidazo[4,5-b]pyridin-2-yl)phenoxy]ethyl}piperidin-4-ol bis(trifluoroacetate)

The title compound was prepared from 6-bromo-2-[4-(2-chloroethoxy)phenyl]-3H-imidazo[4,5-b]pyridine and piperidin-4-ol.
APCI-MS m/z: 417.4/419.4 [MH$^+$].

EXAMPLE 113

6-Bromo-2-(4-{2-[4-(2-methoxyphenyl)piperazin-1-yl]ethoxy}phenyl)-3H-imidazo[4,5-b]pyridine bis(trifluoroacetate)

The title compound was prepared from 6-bromo-2-[4-(2-chloroethoxy)phenyl]-3H-imidazo[4,5-b]pyridine and 1-(2-methoxyphenyl)piperazine.
APCI-MS m/z: 508.5/510.5 [MH$^+$].

EXAMPLE 114

(2S)-2-({2-[4-(6-Bromo-3H-imidazo[4,5-b]pyridin-2-yl)phenoxy]ethyl}amino)-3-methylbutan-1-ol bis(trifluoroacetate)

The title compound was prepared from 6-bromo-2-[4-(2-chloroethoxy)phenyl]-3H-imidazo[4,5-b]pyridine and (2S)-2-amino-3-methylbutan-1-ol.
APCI-MS m/z: 419.4/421.4 [MH$^+$].

EXAMPLE 115

N-{2-[4-(6-Bromo-3H-imidazo[4,5-b]pyridin-2-yl)phenoxy]ethyl}-4,5-dihydro-1,3-thiazol-2-amine bis(trifluoroacetate)

The title compound was prepared from 6-bromo-2-[4-(2-chloroethoxy)phenyl]-3H-imidazo[4,5-b]pyridine and 4,5-dihydro-1,3-thiazol-2-amine.
APCI-MS m/z: 418.3/420.3 [MH$^+$].

EXAMPLE 116

N-{2-[4-(6-Bromo-3H-imidazo[4,5-b]pyridin-2-yl)phenoxy]ethyl}-N-[2-(1H-indol-3-yl)ethyl]amine bis(trifluoroacetate)

The title compound was prepared from 6-bromo-2-[4-(2-chloroethoxy)phenyl]-3H-imidazo[4,5-b]pyridine and 2-(1H-indol-3-yl)ethanamine.
APCI-MS m/z: 476.4/478.4[MH$^+$].

EXAMPLE 117

(2S)-2-({2-[4-(6-Bromo-3H-imidazo[4,5-b]pyridin-2-yl)phenoxy]ethyl}amino)-2-phenylethanol bis(trifluoroacetate)

The title compound was prepared from 6-bromo-2-[4-(2-chloroethoxy)phenyl]-3H-imidazo[4,5-b]pyridine and (2R)-2-amino-2-phenylethanol.
APCI-MS m/z: 453.4/455.4 [MH$^+$].

EXAMPLE 118

N-{2-[4-(6-Bromo-3H-imidazo[4,5-b]pyridin-2-yl)phenoxy]ethyl}-1H-tetrazol-5-amine bis(trifluoroacetate)

The title compound was prepared from 6-bromo-2-[4-(2-chloroethoxy)phenyl]-3H-imidazo[4,5-b]pyridine and 1H-tetrazol-5-amine.
APCI-MS m/z: 401.3/403.4 [MH$^+$].

EXAMPLE 119

(1S,2R)-2-({2-[4-(6-Bromo-3H-imidazo[4,5-b]pyridin-2-yl)phenoxy]ethyl}amino)cyclohexanol bis(trifluoroacetate)

The title compound was prepared from 6-bromo-2-[4-(2-chloroethoxy)phenyl]-3H-imidazo[4,5-b]pyridine and (1R,2S)-2-aminocyclohexanol hydrochloride.
APCI-MS m/z: 431.4/433.4 [MH$^+$].

EXAMPLE 120

6-Methoxy-2-(4-methoxyphenyl)-3H-imidazo[4,5-b]pyridine trifluoroacetate

Sodium methoxide, obtained from methanol (4 ml) and sodium (1.23 g, 53 mmol) was added to a solution of 6-bromo-2-(4-methoxyphenyl)-3H-imidazo[4,5-b]pyridine (0.304 g, 1 mmol) and cuprous bromide (0.286 g, 2 mmol) in DMF (6.4 ml). The reaction mixture was heated under reflux overnight. After cooling, water (100 ml) was added and the precipitate was filtered off. The solid substance was dissolved in DMF (5 ml) and purified by RP-HPLC (10-60% acetonitrile) to give the title compound.
$^1$H NMR (DMSO-d$_6$): δ 8.15 (3H, d); 7.62 (1H, s); 7.16 (2H, d); 3.90 (3H, s); 3.86 (3H, s). APCI-MS m/z: 256.2 [MH$^+$].

EXAMPLE 121

6-Bromo-2-[4-(oxiran-2-ylmethoxy)phenyl]-3H-imidazo[4,5-b]pyridine 4-(6-Bromo-3H-imidazo[4,5-b]pyridin-2-yl)phenol (2 g, 6.89 mmol) was dissolved in DMF (200 ml) and sodium hydride (0.9 g, 20.67 mmol, 55% in oil) was added. The mixture was stirred at 50° C. for 1 h, and epibromohydrin (0.94 ml, 11.37 mmol) was added dropwise followed by stirring for one h at room temperature. Purification by flash chromatography on silica using ethyl acetate/heptane as eluent afforded the title compound (0.55 g, 23%).
APCI-MS m/z: 346/348 [MH$^+$].
$^1$H NMR (DMSO-d$_6$): δ 8.37 (1H, d); 8.20 (1H, brs); 8.17 (2H, d); 7.16 (2H, d); 4.47-4.43 (1H, dd); 3.96-3.92 (1H, dd); 2.87 (1H, t); 2.75-2.73 (1H, dd).

EXAMPLE 122

1-[4-(6-Bromo-3H-imidazo[4,5-b]pyridin-2-yl)phenoxy]-3-pyrrolidin-1-ylpropan-2-ol To a solution of 6-bromo-2-[4-(oxiran-2-ylmethoxy)phenyl]-3H-imidazo[4,5-b]pyridine (119 mg, 0.35 mmol) in DMF (8 ml), pyrrolidine (144 μl, 1.73 mmol) was added. The mixture was heated at 85° C. for 10 h. 5% Aqueous ammonium chloride was added and the mixture was extracted with ethyl acetate. The organic phase was filtered and concentrated. Purification by flash chromatography on silica using methylene chloride/methanol/ammonia as eluent afforded the title compound (35 mg, 24%).
$^1$H NMR (CD$_3$OD): δ 8.37 (1H, s); 8.10-8.07 (3H, m); 7.14 (2H, d); 4.19-4.10 (2H, m); 4.06-4.02 (1H, m); 2.86-2.82 (1H, m); 2.74-2.69 (5H, m); 1.88-1.82 (4H, m). APCI-MS m/z: 417/419 [MH$^+$].

Using the general method of Example 122, the compounds of Examples 123 to 173 were prepared:

EXAMPLE 123

1-[4-(6-Bromo-3H-imidazo[4,5-b]pyridin-2-yl)phenoxy]-3-morpholin-4-ylpropan-2-ol The title compound was prepared from 6-bromo-2-[4-(oxiran-2-ylmethoxy)phenyl]-3H-imidazo[4,5-b]pyridine and morpholine.
$^1$H NMR (CD$_3$OD): δ 8.37 (1H, d); 8.09-8.06 (3H, m); 7.14 (2H, d); 4.18-4.11 (2H, m); 4.07-4.02 (1H, m); 3.71 (4H, t); 2.59-2.55 (6H, m). APCI-MS m/z: 433/435 [MH$^+$].

EXAMPLE 124

1-{3-[4-(6-Bromo-3H-imidazo[4,5-b]pyridin-2-yl)phenoxy]-2-hydroxypropyl}pyrrolidin-3-ol The title compound was prepared from 6-bromo-2-[4-(oxiran-2-ylmethoxy)phenyl]-3H-imidazo[4,5-b]pyridine and pyrrolidin-3-ol.
$^1$H NMR (CD$_3$OD): δ 8.38 (1H, d); 8.10-8.07 (3H, m); 7.15 (2H, d); 4.48-4.42 (1H, m); 4.27-4.18 (1H, m); 4.15-4.05 (2H, m); 3.27-2.93 (6H, m); 2.27-2.15 (1H, m); 1.92-1.85 (1H, m). APCI-MS m/z: 433/435 [MH+].

EXAMPLE 125

1-[4-(6-Bromo-3H-imidazo[4,5-b]pyridin-2-yl)phenoxy]-3-piperidin-1-ylpropan-2-ol The title compound was prepared from 6-bromo-2-[4-(oxiran-2-ylmethoxy)phenyl]-3H-imidazo[4,5-b]pyridine and piperidine.
$^1$H NMR (CD$_3$OD): δ 8.39 (1H, d); 8.10-8.08 (3H, m); 7.15 (2H, d); 4.234.19 (1H, m); 4.13-4.10 (1H, m); 4.06-4.02 (1H, m); 2.74-2.65 (6H, m); 1.69-1.65 (4H, m); 1.55-1.51 (2H, m). APCI-MS m/z: 431/433 [MH+].

EXAMPLE 126

1-[4-(6-Bromo-3H-imidazo[4,5-b]pyridin-2-yl)phenoxy]-3-(diethylamino)propan-2-ol The title compound was prepared from 6-bromo-2-[4-(oxiran-2-ylmethoxy)phenyl]-3H-imidazo[4,5-b]pyridine and diethylamine.
$^1$H NMR (CD$_3$OD): δ 8.38 (1H, d); 8.10-8.07 (3H, m); 7.15 (2H, d); 4.15-4.05 (3H, m); 2.85-2.70 (6H, m); 1.13 (6H, t). APCI-MS m/z: 419/421 [MH+].

EXAMPLE 127

1-{3-[4-(6-Bromo-3H-imidazo[4,5-b]pyridin-2-yl)phenoxy]-2-hydroxypropyl}piperidin-4-ol bis(trifluoroacetate)

The title compound was prepared from 6-bromo-2-[4-(oxiran-2-ylmethoxy)phenyl]-3H-imidazo[4,5-b]pyridine and piperidin-4-ol.
$^1$H NMR (CD$_3$OD): δ 8.50 (1H, d); 8.21 (1H, d); 8.13 (2H, d); 7.22 (2H, d); 4.50-4.42 (1H, m); 4.17-4.11 (3H, m); 3.91-3.83 (1H, m); 3.75-3.69 (1H, m); 3.54-3.08 (5H, m); 2,20-1.75 (4H, m). APCI-MS m/z: 447/449 [MH+].

EXAMPLE 128

1-(4-Acetylpiperazin-1-yl)-3-[4-(6-bromo-3H-imidazo[4,5-b]pyridin-2-yl)phenoxy]propan-2-ol bis(trifluoroacetate)

The title compound was prepared from 6-bromo-2-[4-(oxiran-2-ylmethoxy)phenyl]-3H-imidazo[4,5-b]pyridine (10 mg, 0.03 mmol) and 1-acetylpiperazine (37 mg, 0.29 mmol). Purification by preparative HPLC gave the required compound (8 mg, 39. %).
$^1$H NMR (CD$_3$OD): δ 8.50 (1H, d); 8.21 (1H, d); 8.13 (2H, d); 7.21 (2H, d); 4.53-4.47 (1H, m); 4.19-4.13 (2H, m); 4,01-3.89 (2H, m); 3.64-3.33 (6H, m); 2.17 (3H, s). APCI-MS m/z: 474/476 [MH+].

EXAMPLE 129

1-[4-(6-Bromo-3H-imidazo[4,5-b]pyridin-2-yl)phenoxy]-3-[3-(dimethylamino)pyrrolidin-1-yl]propan-2-ol bis(trifluoroacetate)

The title compound was prepared from 6-bromo-2-[4-(oxiran-2-ylmethoxy)phenyl]-3H-imidazo[4,5-b]pyridine (10 mg, 0.03 mmol) and 3-dimethylaminepyrrolidine (13 mg, 0.12 mmol).
$^1$H NMR (CD$_3$OD): δ 8.49 (1H, d); 8.20 (1H, d); 8.13 (2H, d); 7.21 (2H, d); 4.44-4.38 (1H, m); 4.23-4.13 (3H, m); 4.04-3.97 (1H, m); 3.93-3.89 (1H, m); 3.79 (1H, brs); 3.62-3.53 (3H, m); 2.99 (6H, s); 2.70-2.61 (1H, m); 2.47-2.38 (1H, m). APCI-MS m/z: 460/462 [MH+].

EXAMPLE 130

4-[({2-Hydroxy-3-[4-(6-methyl-3H-imidazo[4,5-b]pyridin-2-yl)phenoxy]propyl}amino)methyl]phenol bis(trifluoroacetate)

The title compound was prepared from 6-bromo-2-[4-(oxiran-2-ylmethoxy)phenyl]-3H-imidazo[4,5-b]pyridine (15 mg, 0.04 mmol) and 4-methoxybenzylamine (28 μl, 0.22 mmol).
APCI-MS m/z: 483/485 [MH+].

EXAMPLE 131

1-[4-(6-Bromo-3H-imidazo[4,5-b]pyridin-2-yl)phenoxy]-3-[(2-hydroxyethyl)(methyl)amino]propan-2-ol bis(trifluoroacetate)

The title compound was prepared from 6-bromo-2-[4-(oxiran-2-ylmethoxy)phenyl]-3H-imidazo[4,5-b]pyridine and 2-(methylamino)ethanol.
APCI-MS m/z: 421/423 [MH+].

EXAMPLE 132

3-[{3-[4-(6-Bromo-3H-imidazo[4,5-b]pyridin-2-yl)phenoxy]-2-hydroxypropyl}(methyl)amino]propanenitrile bis(trifluoroacetate)

The title compound was prepared from 6-bromo-2-[4-(oxiran-2-ylmethoxy)phenyl]-3H-imidazo[4,5-b]pyridine and 3-(methylamino)propanenitrile.
APCI-MS m/z: 430/432 [MH+].

EXAMPLE 133

4-{3-[4-(6-Bromo-3H-imidazo[4,5-b]pyridin-2-yl)phenoxy]-2-hydroxypropyl}piperazin-1-ol bis(trifluoroacetate)

The title compound was prepared from 6-bromo-2-[4-(oxiran-2-ylmethoxy)phenyl]-3H-imidazo[4,5-b]pyridine and 1-methylpiperazine.
APCI-MS m/z: 446/448 [MH+].

EXAMPLE 134

$N^2$-{3-[4-(6-Bromo-3H-imidazo[4,5-b]pyridin-2-yl)phenoxy]-2-hydroxypropyl}-$N^1$,$N^1$,$N^2$-trimethylglycinamide bis(trifluoroacetate)

The title compound was prepared from 6-bromo-2-[4-(oxiran-2-ylmethoxy)phenyl]-3H-imidazo[4,5-b]pyridine and $N^1$,$N^1$,$N^2$-trimethylglycinamide.
APCI-MS m/z: 462/464 [MH+].

EXAMPLE 135

1-[Benzyl(methyl)amino]-3-[4-(6-bromo-3H-imidazo[4,5-b]pyridin-2-yl)phenoxy]propan-2-ol bis(trifluoroacetate)

The title compound was prepared from 6-bromo-2-[4-(oxiran-2-ylmethoxy)phenyl]-3H-imidazo[4,5-b]pyridine and N-benzyl-N-methylamine.
APCI-MS m/z: 467/469 [MH$^+$].

EXAMPLE 136

1-[4-(6-Bromo-3H-imidazo[4,5-b]pyridin-2-yl)phenoxy]-3-[methyl(2-phenylethyl)amino]propan-2-ol bis(trifluoroacetate)

The title compound was prepared from 6-bromo-2-[4-(oxiran-2-ylmethoxy)phenyl]-3H-imidazo[4,5-b]pyridine and N-methyl-N-(2-phenylethyl)amine.
APCI-MS m/z: 481/483 [MH$^+$].

EXAMPLE 137

1-[4-(6-Bromo-3H-imidazo[4,5-b]pyridin-2-yl)phenoxy]-3-(4-phenylpiperazin-1-yl)propan-2-ol bis(trifluoroacetate)

The title compound was prepared from 6-bromo-2-[4-(oxiran-2-ylmethoxy)phenyl]-3H-imidazo[4,5-b]pyridine and 1-phenylpiperazine.
APCI-MS m/z: 508/510 [MH$^+$].

EXAMPLE 138

1-[4-(6-Bromo-3H-imidazo[4,5-b]pyridin-2-yl)phenoxy]-3-(4-pyridin-2-ylpipiperazin-1-yl)propan-2-ol bis(trifluoroacetate)

The title compound was prepared from 6-bromo-2-[4-(oxiran-2-ylmethoxy)phenyl]-3H-imidazo[4,5-b]pyridine and 1-pyridin-2-ylpiperazine.
APCI-MS m/z: 509/511 [MH$^+$].

EXAMPLE 139

1-[2-(3-[4-(6-Bromo-3H-imidazo[4,5-b]pyridin-2-yl)phenoxy]-2-hydroxypropyl amino)ethyl]imidazolidin-2-one bis(trifluoroacetate)

The title compound was prepared from 6-bromo-2-[4-(oxiran-2-ylmethoxy)phenyl]-3H-imidazo[4,5-b]pyridine and 1-(2-aminoethyl)imidazolidin-2-one.
APCI-MS m/z: 475/477 [MH$^+$].

EXAMPLE 140

1-[4-(6-Bromo-3H-imidazo[4,5-b]pyridin-2-yl)phenoxy]-3-[(3-methoxybenzyl)amino]propan-2-ol bis(trifluoroacetate)

The title compound was prepared from 6-bromo-2-[4-(oxiran-2-ylmethoxy)phenyl]-3H-imidazo[4,5-b]pyridine and 3-methoxybenzylamine.
APCI-MS m/z: 483/485 [MH$^+$].

EXAMPLE 141

1-[4-(6-Bromo-3H-imidazo[4,5-b]pyridin-2-yl)phenoxy]-3-[(2-chlorobenzyl)amino]propan-2-ol bis(trifluoroacetate)

The title compound was prepared from 6-bromo-2-[4-(oxiran-2-ylmethoxy)phenyl]-3H-imidazo[4,5-b]pyridine and 2-chlorobenzylamine.
APCI-MS m/z: 487/489 [MH$^+$].

EXAMPLE 142

1-[4-(6-Bromo-3H-imidazo[4,5-b]pyridin-2-yl)phenoxy]-3-[(4-chlorobenzyl)amino]propan-2-ol bis(trifluoroacetate)

The title compound was prepared from 6-bromo-2-[4-(oxiran-2-ylmethoxy)phenyl]-3H-imidazo[4,5-b]pyridine and 4-chlorobenzylamine.
APCI-MS m/z: 487/489 [MH$^+$].

EXAMPLE 143

1-[4-(6-Bromo-3H-imidazo[4,5-b]pyridin-2-yl)phenoxy]-3-[(3-chlorobenzyl)amino]propan-2-ol bis(trifluoroacetate)

The title compound was prepared from 6-bromo-2-[4-(oxiran-2-ylmethoxy)phenyl]-3H-imidazo[4,5-b]pyridine and 3-chlorobenzylamine.
APCI-MS m/z: 487/489 [MH$^+$].

EXAMPLE 144

Ethyl 4-({3-[4-(6-bromo-3H-imidazo[4,5-b]pyridin-2-yl)phenoxy]-2-hydroxypropyl}amino)piperidine-1-carboxylate bis(trifluoroacetate)

The title compound was prepared from 6-bromo-2-[4-(oxiran-2-ylmethoxy)phenyl]-3H-imidazo[4,5-b]pyridine and ethyl 4-aminopiperidine-1-carboxylate.
APCI-MS m/z: 518/520 [MH$^+$].

EXAMPLE 145

1-[4-(6-Bromo-3H-imidazo[4,5-b]pyridin-2-yl)phenoxy]-3-[4-(2-methoxyethyl)piperazin-1-yl]propan-2-ol bis(trifluoroacetate)

The title compound was prepared from 6-bromo-2-[4-(oxiran-2-ylmethoxy)phenyl]-3H-imidazo[4,5-b]pyridine and 1-(2-methoxyethyl)piperazine.
APCI-MS m/z: 490/492 [MH$^+$].

EXAMPLE 146

1-[4-(6-Bromo-3H-imidazo[4,5-b]pyridin-2-yl)phenoxy]-3-(cyclopropylamino)propan-2-ol bis(trifluoroacetate)

The title compound was prepared from 6-bromo-2-[4-(oxiran-2-ylmethoxy)phenyl]-3H-imidazo[4,5-b]pyridine and cyclopropylamine.
APCI-MS m/z: 403/405 [MH$^+$].

EXAMPLE 147

3-({3-[4-(6-Bromo-3H-imidazo[4,5-b]pyridin-2-yl)phenoxy]-2-hydroxypropyl amino)propan-2-ol bis(trifluoroacetate)

The title compound was prepared from 6-bromo-2-[4-(oxiran-2-ylmethoxy)phenyl]-3H-imidazo[4,5-b]pyridine and 1-amino-2-propanol.
APCI-MS m/z: 421/423 [MH$^+$].

EXAMPLE 148

1-[4-(6-Bromo-3H-imidazo[4,5-b]pyridin-2-yl)phenoxy]-3-[(2-methoxyethyl)amino]propan-2-ol bis(trifluoroacetate)

The title compound was prepared from 6-bromo-2-[4-(oxiran-2-ylmethoxy)phenyl]-3H-imidazo[4,5-b]pyridine and 2-methoxyethylamine.
APCI-MS m/z: 421/423 [MH$^+$].

EXAMPLE 149

2-({3-[4-(6-Bromo-3H-imidazo[4,5-b]pyridin-2-yl)phenoxy]-2-hydroxypropyl}amino)propan-1-ol bis(trifluoroacetate)

The title compound was prepared from 6-bromo-2-[4-(oxiran-2-ylmethoxy)phenyl]-3H-imidazo[4,5-b]pyridine and DL-2-aminopropan-1-ol.
APCI-MS m/z: 421/423 [MH$^+$].

EXAMPLE 150

1-(Benzylamino)-3-[4-(6-bromo-3H-imidazo[4,5-b]pyridin-2-yl)phenoxy]propan-2-ol bis(trifluoroacetate)

The title compound was prepared from 6-bromo-2-[4-(oxiran-2-ylmethoxy)phenyl]-3H-imidazo[4,5-b]pyridine and benzylamine.
APCI-MS m/z: 453/455 [MH$^+$].

EXAMPLE 151

1-[4-(6-Bromo-3H-imidazo[4,5-b]pyridin-2-yl)phenoxy]-3-[(pyridin-3-yl methyl)amino]propan-2-ol bis(trifluoroacetate)

The title compound was prepared from 6-bromo-2-[4-(oxiran-2-ylmethoxy)phenyl]-3H-imidazo[4,5-b]pyridine and 1-pyridin-3-ylmethanamine.
APCI-MS m/z: 454/456 [MH$^+$].

EXAMPLE 152

1-[4-(6-Bromo-3H-imidazo[4,5-b]pyridin-2-yl)phenoxy]-3-[(pyridin-4-ylmethyl)amino]propan-2-ol bis(trifluoroacetate)

The title compound was prepared from 6-bromo-2-[4-(oxiran-2-ylmethoxy)phenyl]-3H-imidazo[4,5-b]pyridine and 1-pyridin-4-ylmethanamine.
APCI-MS m/z: 454/456 [MH$^+$].

EXAMPLE 153

1-[4-(6-Bromo-3H-imidazo[4,5-b]pyridin-2-yl)phenoxy]-3-[(1-ethylpiperidin-3-yl)amino]propan-2-ol bis(trifluoroacetate)

The title compound was prepared from 6-bromo-2-[4-(oxiran-2-ylmethoxy)phenyl]-3H-imidazo[4,5-b]pyridine and l-ethylpiperidin-3-amine.
APCI-MS m/z: 474/476 [MH$^+$].

EXAMPLE 154

1-[4-(6-Bromo-3H-imidazo[4,5-b]pyridin-2-yl)phenoxy]-3-[(2-morpholin-4-ylethyl)amino]propan-2-ol bis(trifluoroacetate)

The title compound was prepared from 6-bromo-2-[4-(oxiran-2-ylmethoxy)phenyl]-3H-imidazo[4,5-b]pyridine and 2-morpholin-4-ylethanamine.
APCI-MS m/z: 476/478 [MH$^+$].

EXAMPLE 155

1-[3-({3-[4-(6-Bromo-3H-imidazo[4,5-b]pyridin-2-yl])phenoxy]-2-hydroxypropyl amino)propyl]pyrrolidin-2-one bis(trifluoroacetate)

The title compound was prepared from 6-bromo-2-[4-(oxiran-2-ylmethoxy)phenyl]-3H-imidazo[4,5-b]pyridine and 1-(3-aminopropyl)pyrrolidin-2-one.
APCI-MS m/z: 488/490 [MH$^+$].

EXAMPLE 156

1-{3-[4-(6-Bromo-3H-imidazo[4,5-b]pyridin-2-yl)phenoxy]-2-hydroxypropyl}piperidin-3-ol bis(trifluoroacetate)

The title compound was prepared from 6-bromo-2-[4-(oxiran-2-ylmethoxy)phenyl]-3H-imidazo[4,5-b]pyridine and piperidin-3-ol.
APCI-MS m/z: 447/449 [MH$^+$].

EXAMPLE 157

1-{3-[4-(6-Bromo-3H-imidazo[4,5-b]pyridin-2-yl)phenoxy]-2-hydroxypropyl}prolinamide bis(trifluoroacetate)

The title compound was prepared from 6-bromo-2-[4-(oxiran-2-ylmethoxy)phenyl]-3H-imidazo[4,5-b]pyridine and D-prolinamide.
APCI-MS m/z: 460/462 [MH$^+$].

EXAMPLE 158

1-[4-(6-Bromo-3H-imidazo[4,5-b]pyridin-2-yl)phenoxy]-3-[4-(hydroxymethyl)piperidin-1-yl]propan-2-ol bis(trifluoroacetate)

The title compound was prepared from 6-bromo-2-[4-(oxiran-2-ylmethoxy)phenyl]-3H-imidazo[4,5-b]pyridine and piperidin-4-ylmethanol.
APCI-MS m/z: 461/463 [MH$^+$].

EXAMPLE 159

1-[4-(6-Bromo-3H-imidazo[4,5-b]pyridin-2-yl)phenoxy]-3-[2-(hydroxymethyl)piperidin-1-yl]propan-2-ol bis(trifluoroacetate)

The title compound was prepared from 6-bromo-2-[4-(oxiran-2-ylmethoxy)phenyl]-3H-imidazo[4,5-b]pyridine and piperidin-2-ylmethanol.
APCI-MS m/z: 461/463 [MH$^+$].

EXAMPLE 160

1-{3-[4-(6-Bromo-3H-imidazo[4,5-b]pyridin-2-yl)phenoxy]-2-hydroxypropyl}piperidine-4-carboxamide bis(trifluoroacetate)

The title compound was prepared from 6-bromo-2-[4-(oxiran-2-ylmethoxy)phenyl]-3H-imidazo[4,5-b]pyridine and piperidine-4-carboxamide.
APCI-MS m/z: 474/476 [MH$^+$].

EXAMPLE 161

1-{3-[4-(6-Bromo-3H-imidazo[4,5-b]pyridin-2-yl)phenoxy]-2-hydroxypropyl}piperidine-3-carboxamide bis(trifluoroacetate)

The title compound was prepared from 6-bromo-2-[4-(oxiran-2-ylmethoxy)phenyl]-3H-imidazo[4,5-b]pyridine and piperidine-3-carboxamide.
APCI-MS m/z: 474/476 [MH$^+$].

EXAMPLE 162

1-[4-(6-Bromo-3H-imidazo[4,5-b]pyridin-2-yl)phenoxy]-3-[4-(2-hydroxyethyl)piperazin-1-yl]propan-2-ol bis(trifluoroacetate)

The title compound was prepared from 6-bromo-2-[4-(oxiran-2-ylmethoxy)phenyl]-3H-imidazo[4,5-b]pyridine and 2-piperazin-1-ylethanol.
APCI-MS m/z: 476/478 [MH$^+$].

EXAMPLE 163

2-(4-3-[4-(6-Bromo-3H-imidazo[4,5-b]pyridin-2-yl)phenoxy]-2-hydroxypropyl)piperazin-1-yl)benzonitrile bis(trifluoroacetate)

The title compound was prepared from 6-bromo-2-[4-(oxiran-2-ylmethoxy)phenyl]-3H-imidazo[4,5-b]pyridine and 2-piperazin-1-ylbenzonitrile.
APCI-MS m/z: 533/535 [MH$^+$].

EXAMPLE 164

6-(4-{3-[4-(6-Bromo-3H-imidazo[4,5-b]pyridin-2-yl)phenoxy]-2-hydroxypropyl}piperazin-1-yl)nicotinonitrile bis(trifluoroacetate)

The title compound was prepared from 6-bromo-2-[4-(oxiran-2-ylmethoxy)phenyl]-3H-imidazo[4,5-b]pyridine and 6-piperazin-1-ylnicotinonitrile.
APCI-MS m/z: 534/536 [MH$^+$].

EXAMPLE 165

1-[4-(6-Bromo-3H-imidazo[4,5-b]pyridin-2-yl)phenoxy]-3-chloropropan-2-ol trifluoroacetate The title compound was prepared from 6-bromo-2-[4-(oxiran-2-ylmethoxy)phenyl]-3H-imidazo[4,5-b]pyridine.
APCI-MS m/z: 382/384 [MH$^+$].

EXAMPLE 166

1-[4-(6-Bromo-3H-imidazo[4,5-b]pyridin-2-yl)phenoxy]-3-(1,3-thiazol-2-ylamino)propan-2-ol bis(trifluoroacetate)

The title compound was prepared from 6-bromo-2-[4-(oxiran-2-ylmethoxy)phenyl]-3H-imidazo[4,5-b]pyridine and 2-aminothiazole.
APCI-MS m/z: 452/454 [MH$^+$].

EXAMPLE 167

1-[4-(6-Bromo-3H-imidazo[4,5-b]pyridin-2-yl)phenoxy]-3-(4-pyrazin-2-ylpiperazin-1-yl)propan-2-ol bis(trifluoroacetate)

The title compound was prepared from 6-bromo-2-[4-(oxiran-2-ylmethoxy)phenyl]-3H-imidazo[4,5-b]pyridine and 2-piperazin-1-ylpyrazine.
APCI-MS m/z: 510/512 [MH$^+$].

EXAMPLE 168

1-[4-(6-Bromo-3H-imidazo[4,5-b]pyridin-2-yl)phenoxy]-3-[(2-methoxybenzyl)amino]propan-2-ol bis(trifluoroacetate)

The title compound was prepared from 6-bromo-2-[4-(oxiran-2-ylmethoxy)phenyl]-3H-imidazo[4,5-b]pyridine and 2-methoxybenzylamine.
APCI-MS m/z: 483/485 [MH$^+$].

EXAMPLE 169

4-[{3-[4-(6-Bromo-3H-imidazo[4,5-b]pyridin-2-yl)phenoxy]-2-hydroxypropyl}(methyl)amino]cyclohexanecarbonitrile bis(trifluoroacetate)

The title compound was prepared from 6-bromo-2-[4-(oxiran-2-ylmethoxy)phenyl]-3H-imidazo[4,5-b]pyridine and 4-(methylamino)cyclohexanecarbonitrile.
APCI-MS m/z: 484/486 [MH$^+$].

EXAMPLE 170

1-[4-(6-Bromo-3H-imidazo[4,5-b]pyridin-2-yl)phenoxy]-3-(2-pyridin-3-ylpiperidin-1-yl)propan-2-ol bis(trifluoroacetate)

The title compound was prepared from 6-bromo-2-[4-(oxiran-2-ylmethoxy)phenyl]-3H-imidazo[4,5-b]pyridine and 3-piperidin-2-ylpyridine.
APCI-MS m/z: 508/510 [MH$^+$].

EXAMPLE 171

1-{3-[4-(6-Bromo-3H-imidazo[4,5-b]pyridin-2-yl)phenoxy]-2-hydroxypropyl}-4-phenylpiperidin-4-ol bis(trifluoroacetate)

The title compound was prepared from 6-bromo-2-[4-(oxiran-2-ylmethoxy)phenyl]-3H-imidazo[4,5-b]pyridine and 4-phenylpiperidin-4-ol.
APCI-MS m/z: 523/525 [MH$^+$].

EXAMPLE 172

2-({3-[4-(6-Bromo-3H-imidazo[4,5-b]pyridin-2-yl)phenoxy]-2-hydroxypropyl}amino)-3-methylbutan-1-ol bis(trifluoroacetate)

The title compound was prepared from 6-bromo-2-[4-(oxiran-2-ylmethoxy)phenyl]-3H-imidazo[4,5-b]pyridine and (2S)-2-amino-3-methylbutan-1-ol.
APCI-MS m/z: 449/451 [MH$^+$].

EXAMPLE 173

1-[4-(6-Bromo-3H-imidazo[4,5-b]pyridin-2-yl)phenoxy]-3-[4-(3-methoxyphenyl)piperazin-1-yl]propan-2-ol bis(trifluoroacetate)

The title compound was prepared from 6-bromo-2-[4-(oxiran-2-ylmethoxy)phenyl]-3H-imidazo[4,5-b]pyridine and 1-(3-methoxyphenyl)piperazine.
APCI-MS m/z: 538/540 [MH$^+$].

EXAMPLE 174

4-(6-Bromo-3H-imidazo[4,5-b]pyridin-2-yl)aniline

To a stirred solution of 6-bromo-2-(4-nitrophenyl)-3H-imidazo[4,5-b]pyridine (1.6 g, 5 mmol) in methanol (45 ml) ammonium sulfide (8.5 ml, 25 mmol, 20% solution in water) was added slowly. The mixture was stirred at room temperature for 30 minutes and then heated and refluxed for 5 h. The reaction mixture was concentrated and cooled to 0° C. The precipitate was filtered off, washed with cold methanol and dried to give the title compound.
$^1$H NMR (CD$_3$OD): δ 7.51 (1H, brs); 7.20 (1H, brs); 7.06 (2H, dd); 5.98 (2H, dd). APCI-MS m/z: 289.0/291.0 [MH$^+$].

EXAMPLE 175

4-({[4-(6-Bromo-3H-imidazo[4,5-b]pyridin-2-yl)phenyl]amino}methyl)benzonitrile bis(trifluoroacetate)

4-(6-Bromo-3H-imidazo[4,5-b]pyridin-2-yl)aniline (50 mg, 0.17 mmol), 4-cyanobenzaldehyde (23 mg, 0.17 mmol) and acetic acid (501 μl) were mixed in NMP (500 μl). Trimethylsilylchloride (44 μl, 0.35 mmol) and NaBH(OAc)$_3$ (73 mg, 0.35 mmol) were added and the mixture was stirred for 2 h until analytical LC-MS indicated that the reaction was complete. 1M sodium hydroxide (1 ml) was added and a precipitate was formed upon the subsequent addition of water. The precipitate was collected, washed with ice-cold ethanol and purified by preparative HPLC to yield the title product (28 mg, 26%).

$^1$H NMR (DMSO-d$_6$): δ 8.33 (1H, d); 8.13 (1H, d); 7.93 (2H, d); 7.81 (2H, d); 7.55 (2H, d); 6.71 (2H, d); 4.50 (2H, s). APCI-MS m/z: 404/406 [MH$^+$].

Using the general method of Example 175, the compounds of Examples 176 to 203 were prepared:

EXAMPLE 176

N-Benzyl-N-[4-(6-bromo-3H-imidazo[4,5-b]pyridin-2-yl)phenyl]amine

The title compound was prepared from 4-(6-bromo-3H-imidazo[4,5-b]pyridin-2-yl)aniline (0.289 g, 1 mmol) and benzaldehyde (0.106 g, 1 mmol).
$^1$H NMR (CD$_3$OD): δ 8.27 (1H, s, NH tautomer); 8.07 (1H, s, NH tautomer); 7.92 (2H, dd); 7.39-7.31 (4H, m); 7.25 (1H, brt); 6.96 (1H, t); 6.71 (2H, d); 4.37 (2H, d). APCI-MS m/z: 379.0/381.1 [MH$^+$].

EXAMPLE 177

N-[4-(6-Bromo-3H-imidazo[4,5-b]pyridin-2-yl)phenyl]-N-(1H-imidazol-2-yl methyl)amine bis(trifluoroacetate)

The title compound was prepared from 4-(6-bromo-3H-imidazo[4,5-b]pyridin-2-yl)aniline (0.145 g, 0.5 mmol) and 2-imidazole carboxaldehyde (0.048 g, 0.5 mmol).
$^1$H NMR (DMSO-d$_6$): δ 9,75 (1H, brs); 8.38 (1H, d); 8.21 (1H, brs); 8.17 (2H, brd); 7.66 (2H, s); 7.37 (2H, brd); 4.87 (2H, brs). APCI-MS m/z: 369.1/371.1 [MH$^+$].

EXAMPLE 178

N-[4-(6-Bromo-3H-imidazo[4,5-b]pyridin-2-yl)phenyl]-N-(1H-imidazol-5-yl methyl)amine bis(trifluoroacetate)

The title compound was prepared from 4-(6-bromo-3H-imidazo[4,5-b]pyridin-2-yl)aniline (0.145 g 0.5 mmol) and 4-formylimidazol (0.048 g, 0.5 mmol).
$^1$H NMR (CD$_3$OD): δ 8.87 (1H, brs); 8.47 (1H, brs); 8.15 (1H, brs); 7.96 (2H, d); 7.52 (1H, brs); 6.88 (2H, d); 4.58 (2H, s). APCI-MS m/z: 369.0/371.0 [MH$^+$].

EXAMPLE 179

3-({[4-(6-Bromo-3H-imidazo[4,5-b]pyridin-2-yl)phenyl]amino methyl)benzonitrile bis(trifluoroacetate)

The title compound was prepared from 4-(6-bromo-3H-imidazo[4,5-b]pyridin-2-yl)aniline and 3-cyanobenzaldehyde.
$^1$H NMR (CD$_3$OD): δ 8.43 (1H, d); 8.10 (1H, d); 7.90 (2H, brd); 7.73-7.70 (2H, brm); 7.63 (1H, brd); 7.53-(1H, t); 4.53 (2H, s). APCI-MS m/z: 404.2/406.2 [MH$^+$].

EXAMPLE 180

N-[4-(6-Bromo-3H-imidazo[4,5-b]pyridin-2-yl)phenyl]-N-(4-methoxybenzyl)amine bis(trifluoroacetate)

The title compound was prepared from 4-(6-bromo-3H-imidazo[4,5-b]pyridin-2-yl)aniline and 4-methoxybenzaldehyde.

¹H NMR (CD₃OD): δ 8.46 (1H, d); 8.12 (1H, d); 7.88 (2H, d); 7.29 (2H, d); 6.89 (2H, d); 6.80 (2H, d); 4.38 (2H, s); 3.78 (3H, s). APCI-MS m/z: 409/411 [MH$^+$].

EXAMPLE 181

N-[4-(6-Bromo-3H-imidazo[4,5-b]pyridin-2-yl)phenyl]-N-(2-methoxybenzyl)amine bis(trifluoroacetate)

The title compound was prepared from 4-(6-bromo-3H-imidazo[4,5-b]pyridin-2-yl)aniline and 2-methoxybenzaldehyde.

¹H NMR (CD₃OD): δ 8.48 (1H, d); 8.14 (1H, d); 7.88 (2H, d); 7.28-7.23 (2H, m); 7.00 (1H, d); 6.89 (1H, t); 6.80 (2H, d); 4.44 (2H, s); 3.90 (3H, s). APCI-MS m/z: 409/411 [MH$^+$].

EXAMPLE 182

N-[4-(6-Bromo-3H-imidazo[4,5-b]pyridin-2-yl)phenyl]-N-(3-methoxybenzyl)amine bis(trifluoroacetate)

The title compound was prepared from 4-(6-bromo-3H-imidazo[4,5-b]pyridin-2-yl)aniline and 3-methoxybenzaldehyde.

¹H NMR (CD₃OD): δ 8.44 (1H, d); 8.11 (1H, d); 7.88 (2H, d); 7.24 (1H, t); 6.97-6.94 (2H, m); 6.83-6.77 (3H, m); 4.43 (2H, s); 3.77 (3H, s). APCI-MS m/z: 409/411 [MH$^+$].

EXAMPLE 183

N-[4-(6-Bromo-3H-imidazo[4,5-b]pyridin-2-yl)phenyl]-N-(2-chlorobenzyl)amine bis(trifluoroacetate)

The title compound was prepared from 4-(6-bromo-3H-imidazo[4,5-b]pyridin-2-yl)aniline and 2-chlorobenzaldehyde.

¹H NMR (CD₃OD): δ 8.46 (1H, d); 8.13 (1H, d); 7.90 (2H, d); 7.45-7.40 (2H, m); 7.29-7.25 (2H, m); 6.78 (2H, d); 4.57 (2H, s). APCI-MS m/z: 413/415 [MH$^+$].

EXAMPLE 184

N-[4-(6-Bromo-3H-imidazo[4,5-b]pyridin-2-yl)phenyl]-N-(4-chlorobenzyl)amine bis(trifluoroacetate)

The title compound was prepared from 4-(6-bromo-3H-imidazo[4,5-b]pyridin-2-yl)aniline and 4-chlorobenzaldehyde.

¹H NMR (CD₃OD): δ 8.48 (1H, d); 8.14 (1H, d); 7.89 (2H, d); 7.39-7.32 (4H, m); 6.79 (2H, d); 4.45 (2H, s). APCI-MS m/z: 413/415 [MH$^+$].

EXAMPLE 185

N-[4-(6-Bromo-3H-imidazo[4,5-b]pyridin-2-yl)phenyl]-N-(1H-pyrazol-3-ylmethyl)amine bis(trifluoroacetate)

The title compound was prepared from 4-(6-bromo-3H-imidazo[4,5-b]pyridin-2-yl)aniline and 1H-pyrazole-3-carbaldehyde.

¹H NMR (CD₃OD): δ 8.57 (1H, d); 8.22 (1H, d); 7.91 (2H, d); 7.60 (2H, d); 6.89 (2H, d); 6.31 (2H, s); 4.49 (2H, s). APCI-MS m/z: 369/371 [MH$^+$].

EXAMPLE 186

N-[4-(6-Bromo-3H-imidazo[4,5-b]pyridin-2-yl)phenyl]-N-(3-chlorobenzyl)amine bis(trifluoroacetate)

The title compound was prepared from 4-(6-bromo-3H-imidazo[4,5-b]pyridin-2-yl)aniline and 3-chlorobenzaldehyde.

APCI-MS m/z: 413/415 [MH$^+$].

EXAMPLE 187

[5-({[4-(6-Bromo-3H-imidazo[4,5-b]pyridin-2-yl)phenyl]amino}methyl)-2-furyl]methanol bis(trifluoroacetate)

The title compound was prepared from 4-(6-bromo-3H-imidazo[4,5-b]pyridin-2-yl)aniline and 5-(hydroxymethyl)-2-furaldehyde.

APCI-MS m/z: 399/401 [MH$^+$].

EXAMPLE 188

N-[4-(6-Bromo-3H-imidazo[4,5-b]pyridin-2-yl)phenyl]-N-(thien-2-ylmethyl)amine bis(trifluoroacetate)

The title compound was prepared from 4-(6-bromo-3H-imidazo[4,5-b]pyridin-2-yl)aniline and thiophene-2-carbaldehyde.

APCI-MS m/z: 385/387 [MH$^+$].

EXAMPLE 189

N-[4-(6-Bromo-3H-imidazo[4,5-b]pyridin-2-yl)phenyl]-N-(2-furylmethyl)amine bis(trifluoroacetate)

The title compound was prepared from 4-(6-bromo-3H-imidazo[4,5-b]pyridin-2-yl)aniline and 2-furaldehyde.

APCI-MS m/z: 369/371 [MH$^+$]:

EXAMPLE 190

N-[4-(6-Bromo-3H-imidazo[4,5-b]pyridin-2-yl)phenyl]-N-(thien-3-ylmethyl)amine bis(trifluoroacetate)

The title compound was prepared from 4-(6-bromo-3H-imidazo[4,5-b]pyridin-2-yl)aniline and thiophene-3-carbaldehyde.

APCI-MS m/z: 385/387 [MH$^+$].

EXAMPLE 191

N-[4-(6-Bromo-3H-imidazo[4,5-b]pyridin-2-yl)phenyl]-N-[(4-methyl-1H-imidazol-5-yl)methyl]amine bis(trifluoroacetate)

The title compound was prepared from 4-(6-bromo-3H-imidazo[4,5-b]pyridin-2-yl)aniline and 4-methyl-1H-imidazole-5-carbaldehyde.

APCI-MS m/z: 383/385 [MH$^+$].

EXAMPLE 192

N-[4-(6-Bromo-3H-imidazo[4,5-b]pyridin-2-yl)phenyl]-N-(3-furylmethyl)amine bis(trifluoroacetate)

The title compound was prepared from 4-(6-bromo-3H-imidazo[4,5-b]pyridin-2-yl)aniline and 3-furaldehyde.

APCI-MS m/z: 369/371 [MH$^+$].

EXAMPLE 193

N-[4-(6-Bromo-3H-imidazo[4,5-b]pyridin-2-yl)phenyl]-N-(1,3-thiazol-2-ylmethyl)amine bis(trifluoroacetate)

The title compound was prepared from 4-(6-bromo-3H-imidazo[4,5-b]pyridin-2-yl)aniline and 1,3-thiazole-2-carbaldehyde.
APCI-MS m/z: 386/388 [MH$^+$].

EXAMPLE 194

N-[4-(6-Bromo-3H-imidazo[4,5-b]pyridin-2-yl)phenyl]-N-[(4-bromothien-2-yl)methyl]amine bis(trifluoroacetate)

The title compound was prepared from 4-(6-bromo-3H-imidazo[4,5-b]pyridin-2-yl)aniline and 4-bromothiophene-2-carbaldehyde.
APCI-MS m/z: 463/465/467 [MH$^+$].

EXAMPLE 195

N-[4-(6-Bromo-3H-imidazo[4,5-b]pyridin-2-yl)phenyl]-N-(1H-imidazol-4-ylmethyl)amine bis(trifluoroacetate)

The title compound was prepared from 4-(6-bromo-3H-imidazo[4,5-b]pyridin-2-yl)aniline and 1H-imidazole-5-carbaldehyde.
APCI-MS m/z: 369/371 [MH$^+$].

EXAMPLE 196

N-[4-(6-Bromo-3H-imidazo[4,5-b]pyridin-2-yl)phenyl]-N-[(2-methyl-1H-imidazol-5-yl)methyl]amine bis(trifluoroacetate)

The title compound was prepared from 4-(6-bromo-3H-imidazo[4,5-b]pyridin-2-yl)aniline and 2-methyl-1H-imidazole-5-carbaldehyde.
APCI-MS m/z: 383/385 [MH$^+$].

EXAMPLE 197

N-[4-(6-Bromo-3H-imidazo[4,5-b]pyridin-2-yl)phenyl]-N-[(3,5-dimethylisoxazol-4-yl)methyl]amine bis(trifluoroacetate)

The title compound was prepared from 4-(6-bromo-3H-imidazo[4,5-b]pyridin-2-yl)aniline and 2-methyl-1H-imidazole-5-carbaldehyde.
APCI-MS m/z: 398.2/400.1 [MH$^+$].

EXAMPLE 198

[5-({[4-(6-Bromo-3H-imidazo[4,5-b]pyridin-2-yl)phenyl]amino}methyl)-2-furyl]methyl acetate bis(trifluoroacetate)

The title compound was prepared from 4-(6-bromo-3H-imidazo[4,5-b]pyridin-2-yl)aniline and 2-methyl-1H-imidazole-5-carbaldehyde.
APCI-MS m/z: 441/443 [MH$^+$].

EXAMPLE 199

N-(4-(6-Bromo-3H-imidazo[4,5-b]pyridin-2-yl)phenyl]-N-[(5-pyridin-2-ylthien-2-yl)methyl]amine bis(trifluoroacetate)

The title compound was prepared from 4-(6-bromo-3H-imidazo[4,5-b]pyridin-2-yl)aniline and 2-methyl-1H-imidazole-5-carbaldehyde.
APCI-MS m/z: 462/464 [MH$^+$].

EXAMPLE 200

N-[4-(6-Bromo-3H-imidazo[4,5-b]pyridin-2-yl)phenyl]-N-[(1-methyl-1H-benzimidazol-2-yl)methyl]amine bis(trifluoroacetate)

The title compound was prepared from 4-(6-bromo-3H-imidazo[4,5-b]pyridin-2-yl)aniline and 2-methyl-1H-imidazole-5-carbaldehyde.
APCI-MS m/z: 433.2/435.2 [MH$^+$].

EXAMPLE 201

N-[4-(6-Bromo-3H-imidazo[4,5-b]pyridin-2-yl)phenyl]-N-[(2-ethyl-1H-imidazol-5-yl)methyl]amine bis(trifluoroacetate)

The title compound was prepared from 4-(6-bromo-3H-imidazo[4,5-b]pyridin-2-yl)aniline and 2-methyl-1H-imidazole-5-carbaldehyde.
APCI-MS m/z: 397/399 [MH$^+$].

EXAMPLE 202

N-[4-(6-Bromo-3H-imidazo[4,5-b]pyridin-2-yl)phenyl]-N-[(1methyl-1H-imidazol-5-yl)methyl]amine bis(trifluoroacetate)

The title compound was prepared from 4-(6-bromo-3H-imidazo[4,5-b]pyridin-2-yl)aniline and 2-methyl-1H-imidazole-5-carbaldehyde.
APCI-MS m/z: 383.1/385.1 [MH$^+$].

EXAMPLE 203

Methyl 4-({[4-(6-bromo-3H-imidazo[4,5-b]pyridin-2-yl)phenyl]amino}methyl)-1-methyl-1H-pyrrole-2-carboxylate bis(trifluoroacetate)

The title compound was prepared from 4-(6-bromo-3H-imidazo[4,5-b]pyridin-2-yl)aniline and 2-methyl-1H-imidazole-5-carbaldehyde.
APCI-MS m/z: 440/442 [MH$^+$].

EXAMPLE 204

N-Benzyl-5-(6-bromo-3H-imidazo[4,5-b]pyridin-2-yl)pyridin-2-amine bis(trifluoroacetate)

a) 5-(6-Bromo-3H-imidazo[45-b]pyridin-2-yl)pyridin-2-ol

Polyphosphoric acid (3 g) was heated to 140° C. and 2,3-diamino-5-bromopyridine (417 mg, 2.22-mmol) and 6-chloronicotinic acid (525 mg, 3.33 mmol) were added. The reaction mixture was stirred overnight at 140° C. After cooling, ice was added and the pH adjusted to 7 with a saturated solution of sodium hydrogen carbonate. A precipitate was formed which was filtered off and washed with ethyl acetate to afford the title compound (341 mg, 53%).

$^1$H NMR (DMSO-d$_6$): δ 8.30 (1H, d); 8.29 (1H, d); 8.20-8.17 (1H, dd); 8.14 (1H, d); 6.50 (1H, d). APCI-MS m/z: 290.9/292.9 [MH$^+$].

b) 6-Bromo-2-(6-chloropyridin-3-yl)-3H-imidazo[4,5-b]pyridine 5-(6-Bromo-3H-imidazo[4,5-b]pyridin-2-yl)pyridin-2-ol (300 mg, 1.03 mmol) was added to phosphorous oxychloride (6 ml) and the mixture was stirred at 110° C. for 4 h. The excess phosphorous oxychloride was evaporated off and the remaining oil was purified by flash chromatography using ethyl acetate/heptane as eluent. The title compound was isolated as a yellow solid (139 mg, 44%).

$^1$H NMR (DMSO-d$_6$): δ 13.91 (1H, brs); 9.21 (1H, d); 8.60-8.57 (1H, dd); 8.48 (1H, d); 8.37 (1H, brs); 7.78 (1H, d). APCI-MS m/z: 308.9/310.9 [MH$^+$].

c) N-Benzyl-5-(6-bromo-3H-imidazo[4,5-b]piperidin-2-yl)pyridin-2-amine bis(trifluoroacetate)

6-Bromo-2-(6-chloropyridin-3-yl)-3H-imidazo[4,5-b]pyridine (20 mg, 0.07 mmol) was stirred in benzylamine overnight at 120° C. Purification by HPLC afforded the title compound (20 mg, 51%).

$^1$H NMR (CD$_3$OD): δ 8.72 (1H, d); 8.44 (1H, d); 8.30-8.28 (1H, dd); 8.15 (1H, d); 7.42-7.35 (3H, m): 7.32-7.28 (1H, m); 6.94 (1H, d); 4.65 (2H, s). APCI-MS m/z: 380.2/382.2 [MH$^+$].

EXAMPLE 205

5-(6-Bromo-3H-imidazo[4,5-b]pyridin-2-yl)-N-(3-methoxybenzyl)pyridin-2-amine bis(trifluoroacetate)

The title compound was prepared from 6-bromo-2-(6-chloropyridin-3-yl)-3H-imidazo[4,5-b]pyridine and 3-methoxybenzylamine using the method described in Example 204.

$^1$H NMR (CD$_3$OD): δ 8.74 (1H, d); 8.41 (1H, d); 8.24-8.22 (1H, dd); 8.12 (1H, d); 7.27 (1H, t); 6.96 (2H, d); 6.85 (2H, d); 4.61 (2H, s); 3.78 (3H, s). APCI-MS m/z: 410.2/412.2 [MH$^+$].

EXAMPLE 206

6,7-Dichloro-2-[4-(2-morpholin-4-ylethoxy)phenyl]-3H-imidazo[4,5-b]pyridine 2,3-Diamino-4,5-dichloropyridine (Example 206a) (0.50 g, 2.5 mmol) and 4-(2-morpholin-4-ylethoxy)benzoic acid (Example 206c) (0.80 g, 2.5 mmol) were dissolved in POCl$_3$ (10 ml) and heated to 100° C. for 10 h. The excess of POCl$_3$ was evaporated off and the residue was dissolved in EtOAc and aqueous NaHCO$_3$. The aqueous phase was basified with 10M NaOH and extracted three times with EtOAc. The combined organic phases were washed with brine, dried (Na$_2$SO$_4$) and evaporated in vacuo to afford the title product as a slightly yellow powder (0.74 g, 75%).

APCI-MS m/z: 393.1, 395.1 [MH$^+$].

$^1$H-NMR (400 MHz, DMSO-d$_6$): δ 8.41 (s, 1H), 8.18 (d, J 8.8 Hz, 2H), 7.14 (d, J 9.0 Hz, 2H), 4.18 (t, J 5.7 Hz, 2H), 3.57 (t, J 4.6 Hz, 4H), 2.71 (t, J 5.7 Hz, 2H), 2.49-2.47 (m, 4H).

a) 2,3-Diamino-4,5-dichloropyridine

2-Amino-4,5-dichloro-3-nitropyridine (Example 206b) (1.04 g, 5.0 mmol), zinc powder (2.4 g, 37 mmol) and anhydrous calcium chloride (3 g, 27 mmol) were mixed in 95% ethanol (30 ml) and heated to reflux for 1 h. When cool, the reaction mixture was filtered through celite and evaporated in vacuo. The residue was dissolved in methanol/dichloromethane 1:1 and chromatographed through a short column of silica (10 g) eluting with methanol/dichloromethane 3:7. The fraction containing the product was concentrated in vacuo and the residue dissolved in methanol/acetonitrile 1:9 and again concentrated in vacuo together with silica. The product thus adsorbed on silica gel was again subjected to chromatography on silica gel (EtOAc) to afford the pure product as a off-white powder (0.60 g, 67%).

APCI-MS m/z: 178.1, 180.2 [MH$^+$].

$^1$H-NMR (400 MHz, DMSO-d$_6$): δ 7.36 (s, 1H), 5.95 (s, 2H), 5.27 (s, 2H).

b) 2-Amino-4,5-dichloro-3-nitropyridine

N-(4,5-Dichloropyridin-2-yl)-2,2-dimethylpropanamide[1] (72.0 g, 0.29 mol) was dissolved during 1 h in conc. sulfuric acid (400 ml) and cooled to 10° C. To this solution, nitric acid (d=1.52, 12 ml, 0.29 mol) diluted with conc. sulfuric acid (15 ml) was added dropwise (10 min) while keeping the temperature below 14° C. When the addition was complete, the cooling bath was exchanged for an oil bath and the reaction mixture was heated to 35° C. until all starting material had been consumed (2.5 h) as judged by LC/MS. The reaction mixture was then poured into a vigorously stirred mixture of ice and water (4.5 kg in total) causing a yellow precipitate to form. This solid was collected by filtration and washed with water until the washing liquid tested neutral (10×300 ml). The crude product was dried in vacuo to afford 53.2 g (75% purity, HPLC). Recrystallization from ethanol/water gave large dark brown needles (32.2 g, 53%) of the pure product.

ES-MS m/z: 208.0, 210.1 [MH$^+$].

$^1$H-NMR (400 MHz, DMSO-d$_6$): δ 8.37 (s, 1H), 7.39 (s, 2H).

[1]Synth. Commun., 1997, 27, 861.

c) 4-(2-Morpholin-4-ylethoxy)benzoic acid

Methyl 4-hydroxybenzoate (40 g, 260 mmol) was dissolved in DMF (300 ml), K$_2$CO$_3$ (90 g, 650 mmol) was added and the mixture was heated to 100° C.

4-(2-chloroethyl)morpholine hydrochloride (53 g, 280 mmol) was added slowly (35 min) to the slurry. After 2 h at 100° C., the solid was removed by filtration and the solution was evaporated in vacuo. The residue was dissolved in EtOAc and washed with aqueous NaHCO$_3$, brine and dried (Na$_2$SO$_4$) to give the pure product as a white powder (70 g, 100%).

APCI-MS m/z: 266.1 [MH$^+$].

$^1$H-NMR (400 MHz, DMSO-d$_6$): δ 7.93 (d, J 8.9 Hz, 2H), 7.07 (d, J 8.8 Hz, 2H), 4.19 (t, J 5.7 Hz, 2H), 3.84 (s, 3H), 3.60 (t, J 4.6 Hz, 4H), 2.74 (t, J 5.7 Hz, 2H), 2.52-2.47 (m, 4H).

d) Methyl 4-(2-morpholin-4-ylethoxy)benzoate

Methyl 4-hydroxybenzoate (40 g, 260 mmol) was dissolved in DMF (300 ml), K$_2$CO$_3$ (90 g, 650 mmol) was added and heated to 100° C. 4-(2-Chloroethyl)morpholine hydrochloride (53 g, 280 mmol) was added slowly (35 min) to the slurry. After 2 h at 100° C., the solid was removed by filtration and the solution was evaporated in vacuo. The residue was dissolved in EtOAc and washed with aqueous $NaHCO_3$, brine and dried ($Na_2SO_4$) to give the pure product as a white powder in quantitative yield.

APCI-MS m/z: 266.1 [MH$^+$].

$^1$H-NMR (400 MHz, DMSO-$d_6$): δ 7.93 (d, J 8.9 Hz, 2H), 7.07 (d, J 8.8 Hz, 2H), 4.19 (t, J 5.7 Hz, 2H), 3.84 (s, 3H), 3.60 (t, J 4.6 Hz, 4H), 2.74 (t, J 5.7 Hz, 2H), 2.52-2.47 (m, 4H).

EXAMPLE 207

6-Chloro-N-(2-methoxyphenyl)-2-[4-{2-(4-morpholinyl)ethoxy]phenyl}-1H-imidazo[4,5-b]pyridin-7-amine 6,7-Dichloro-2-[4-(2-morpholin-4-ylethoxy)phenyl]-3H-imidazo[4,5-b]pyridine (Example 206) (30 mg) was dissolved in o-anisidine (0.75 ml) and heated in a microwave oven (180° C., 20 min). The resulting mixture was diluted with acetonitrile (1 ml) and acetic acid (0.5 ml) and subjected to semi-preparative HPLC-C$_{18}$. The fractions containing product (it co-elutes with o-anisidine) were pooled and evaporated in vacuo. The residue was dissolved in EtOAc (20 ml) and washed with 1% aqueous $NaHCO_3$ (10 ml). The organic phase was treated with activated carbon and $MgSO_4$, filtered and evaporated in vacuo. The oily residue was triturated with n-heptane (1 ml) and a few drops of EtOAc, which caused the product to crystallize. It was collected by filtration and washed with EtOAc to give the pure product as a white powder (10 mg, 27%). A second crop (2.9 mg) crystallized from the combined mother liquor and washing liquids.

APCI-MS m/z: 480.4, 482.5 [MH$^+$].

$^1$H-NMR (400 MHz, DMSO-$d_6$): δ 8.09 (s, 1H), 7.91 (d, J 8.4 Hz, 2H), 7.56 (s, 1H), 7.30 (s, 1H), 7.09 (t, J 7.5 Hz, 1H), 7.04 (d, J 8.8 Hz, 2H), 6.89 (t, J 7.9 Hz, 1H), 4.13 (t, J 5.8 Hz, 2H), 3.78 (s, 3H), 3.56 (t, J 4.6 Hz, 4H), 2.69 (t, J 5.7 Hz, 2H), 2.46 (t, J 4.4 Hz, 4H), 13.30 (s, 1H).

EXAMPLE 208

2-[(6-Chloro-2-{4-[2-(4-morpholinyl)ethoxy]phenyl}-1H-imidazo[4,5-b]pyridin-7-yl)amino]phenol 6,7-Dichloro-2-[4-(2-morpholin-4-ylethoxy)phenyl]-3H-imidazo[4,5-b]pyridine (Example 206) (2:9 mg, 7.4 μmol) was dissolved in 48% aqueous HBr (1 ml) and heated at 110° C. for 3 h. whereupon the mixture was neutralized with saturated aqueous $NaHCO_3$ and extracted with EtOAc (5 ml). The organic phase was washed with brine, dried ($MgSO_4$) and evaporated to give a white powder (2.0 mg, 58%).

APCI-MS m/z: 466.5, 468.5 [MH$^+$].

EXAMPLE 209

6-Chloro-N-[1-(methylsulfonyl)-3-pyrrolidinyl]-2-{4-[2-(4-morpholinyl)ethoxy]phenyl}-1H-imidazo[4,5-b]pyridin-7-amine By a procedure similar to that of Example 207 but using 6,7-dichloro-2-[4-(2-morpholin-4-ylethoxy)phenyl]-3H-imidazo[4,5-b]pyridine (Example 206) and 1-(methylsulfonyl)pyrrolidin-3-amine, the title compound was obtained in 19% yield.

APCI-MS m/z: 521.0, 523.1 [MH$^+$].

$^1$H-NMR (300 MHz, DMSO-$d_6$): δ 13.18 (s, 1H), 8.07 (d, J 8.9 Hz, 2H), 7.95 (s, 1H), 7.09 (d, J 8.9 Hz, 2H), 6.18 (d, J 7.7 Hz, 1H), 5.61 (quintet, J 6.8 Hz, 1H), 4.16 (t, J 5.8 Hz, 2H), 3.74 (dd, J 10.2, 6.5 Hz, 1H), 3.58 (t, J 4.7 Hz, 4H), 3.50 (m, 1H), 3.39 (m, 1H), 3.27 (m, 1H), 2.95 (s, 3H), 2.71 (t, J 5.8 Hz, 2H), 2.51-2.43 (m, 4H), 2.35 (td, J 12.6, 7.1 Hz, 1H), 2.16 (dt, J 19.9, 7.4 Hz, 1H).

EXAMPLE 210

6-Chloro-N-cyclopentyl-2-{4-[2-(4-morpholinyl)ethoxy]phenyl}-1H-imidazo[4,5-b]pyridin-7-amine 6,7-Dichloro-2-[4-(2-morpholin-4-ylethoxy)phenyl]-3H-imidazo[4,5-b]pyridine (Example 206) (30 mg, 7.6 μmol) and cyclopentylamine (1 ml) were heated in a microwave oven (170-° C.: 30 min). The excess amine was removed in vacuo and the residue dissolved in acetonitrile (1 ml) with a drop of TFA. This mixture was subjected to semi-preparative HPLC-C$_{18}$. The appropriate fractions were pooled and evaporated in vacuo. The residue was dissolved in EtOAc (5 ml). This solution was washed with saturated aqueous $NaHCO_3$ (5 ml) and brine (2 ml). The organic phase was dried ($MgSO_4$) and evaporated in vacuo and the residue recrystallized from methanol to afford the pure product (16 mg, 47%).

APCI-MS m/z: 442.5, 444.5 [MH$^+$].

$^1$H-NMR (300 MHz, DMSO-$d_6$): δ 13.07 (s, 1H), 8.06 (d, J 8.8 Hz, 2H), 7.89 (s, 1H), 7.09 (d, J 8.8 Hz, 2H), 5.73 (d, J 8.4 Hz, 1H), 5.39 (m, 1H), 4.15 (t, J 5.7 Hz, 2H), 3.58 (t, J 4.6 Hz, 4H), 2.71 (t, J 5.3 Hz, 2H), 2.47 (m, 4H), 2.09 (m, 2H), 1.67 (m, 6H).

EXAMPLE 211

N-Benzyl-6-chloro-2-4-[2-(4-morpholinyl)ethoxy]phenyl-1H-imidazo[4,5-b]pyridin-7-amine 6,7-Dichloro-2-[4-(2-morpholin-4-ylethoxy)phenyl]-3H-imidazo[4,5-b]pyridine (Example 206) (0.50 g, 1.3 mmol) was dissolved in benzylamine (1.2 ml) and heated to 180° C. for 7 h. The reaction mixture was diluted with EtOAc and 2M HCl, which caused the product to crystallize. The crystals were dissolved in EtOAc and aqueous $NaHCO_3$. The organic phase was dried ($Na_2SO_4$) and evaporated in vacuo to give the product (0.48 g, 80%).

APCI-MS m/z: 464.1, 466.1 [MH$^+$].

$^1$H-NMR (400 MHz, DMSO-$d_6$): δ 8.65 (d, J 8.9 Hz, 2H), 7.88 (s, 1H), 7.41 (d, J 7.3 Hz, 2H), 7.26 (t, J 7.6 Hz, 2H), 7.15 (t, J 7.3 Hz, 1H), 7.05 (d, J 8.9 Hz, 2H), 6.88 (t, J 6.8 Hz, 1H), 5.38 (d. J 6.8 Hz, 2H), 4.14 (t, J 5.7 Hz, 2H), 3.57 (t, J 4.6 Hz, 4H), 2.69 (t, J 5.7 Hz, 2H), 2.51-2.42 (m, 4H).

EXAMPLE 212

6-Chloro-2-{4-[2-(4-morpholinyl)ethoxy]phenyl}-1H-imidazo[4,5-b]pyridin-7-amine

N-Benzyl-6-chloro-2-{4-[2-(4-morpholinyl)ethoxy]phenyl}-1H-imidazo[4,5-b]pyridin-7-ammonium bis(trifluoroacetate) (Example 211) (13 mg, 19.5 μmol) was dissolved in aqueous 48% HBr (0.50 ml) and heated at 130° C. for 5 min. When cool again, white crystals were collected by filtration and dissolved in water (5 ml). $K_2CO_3$ (s) was added until pH 9. whereupon the mixture was extracted with EtOAc (5 ml). The organic phase was washed with brine (5 ml) and dried ($MgSO_4$) and concentrated in vacuo. This afforded the pure product (7.1 mg, 99%) as a white powder.

APCI-MS m/z: 374.3, 376.4 [MH$^+$].

¹H-NMR (300 MHz, DMSO-d₆): δ 13.05 (s, 1H), 8.08 (d, J 8.6 Hz, 2H), 7.91 (s, 1H), 7.10 (d, J 8.6 Hz, 2H), 6.44 (s, 2H), 4.16 (t, J 5.7 Hz, 2H), 3.58 (t, J 4.7 Hz, 4H), 2.71 (t, J 5.7 Hz, 2H), 2.48-2.45 (m, 4H).

EXAMPLE 213

6-Chloro-2-{4-[2-(4-morpholinyl)ethoxy]phenyl}-7-(1H-pyrrol-1-yl)-1H-imidazo[4-5-b]pyridine 6-Chloro-2-{4-[2-(4-morpholinyl)ethoxy]phenyl}-1H-imidazo[4,5-b]pyridin-7-amine (Example 212) (17 mg, 45 µmol) was dissolved in acetic acid (5 ml). 2,5-Dimethoxytetrahydrofuran (0.20 ml) was added and the mixture heated (110° C., 3 h) and then allowed to cool and the solvents and excess reagents were removed in vacuo. The residual brown oil was dissolved in acetonitrile (1 ml) and subjected to semi-preparative HPLC-C₁₈. The appropriate fractions were pooled and evaporated in vacuo. The residue was dissolved in EtOAc (5 ml). This solution was washed with saturated aqueous NaHCO₃ (5 ml) and brine (2 ml). The organic phase was dried (MgSO₄) and evaporated in vacuo to afford the pure product (17 mg, 88%) as a beige powder.

APCI-MS m/z: 424.4, 426.5 [MH⁺].

¹H-NMR (300 MHz, THF-d₈): δ 12.54 (s, 1H), 8.29 (s, 1H), 8.11 (d, J 8.8 Hz, 2H), 7.51 (t, J 2.2 Hz, 2H), 7.06 (d, J 8.8 Hz, 2H), 6.32 (t, J 2.2 Hz, 2H), 4.18 (t, J 5.9 Hz, 2H), 3.61 (t, J 4.7 Hz, 4H), 2.77 (t, J 5.9 Hz, 2H), 2.53 (t, J 4.7 Hz, 4H).

EXAMPLE 214

1-(6-Chloro-2-{4-[2-(4-morpholinyl)ethoxy]phenyl}-1H-imidazo[4,5-b]pyridin-7-yl)-3-pyrrolidinamine 6,7-Dichloro-2-[4-(2-morpholin-4-ylethoxy)phenyl]-3H-imidazo[4,5-b]pyridine (Example 206) (40 mg, 110 µmol) and 3-aminopyrrolidine (0.5 ml) were heated at 195° C. for 15 min and then allowed to cool. The reaction mixture was diluted with EtOAc (5 ml) and extracted with 4M HCl (4 ml). The aqueous phase was neutralized with saturated aqueous NaHCO₃ and extracted with EtOAc (4 ml). The organic phase was evaporated in vacuo and the residue dissolved in acetonitrile (2 ml) and subjected to semi-preparative HPLC-C₁₈. The appropriate fractions were pooled and evaporated in vacuo. The residue was dissolved in EtOAc (5 ml). This solution was washed with saturated aqueous NaHCO₃ (5 ml) and brine (2 ml). The organic phase was dried (MgSO₄) and evaporated in vacuo to afford the pure product (30 mg, 61%).

APCI-MS m/z: 443.4, 445.5 [MH⁺].

¹H-NMR (400 MHz, DMSO-d₆): δ 8.06 (d, J 8.9 Hz, 2H), 7.89 (s, 1H), 7.08 (d, J 8.9 Hz, 2H), 4.29-4.22 (m, 2H), 4.19-4.16 (m, 1H), 4.15 (t, J 5.7 Hz, 2H), 3.89 (dd, J 11.1, 4.8 Hz, 1H), 3.63 (m, 1H), 3.57 (t, J 4.6 Hz, 4H), 2.70 (t, J 5.7 Hz, 2H), 2.49-2.46 (m, 4H), 2.07 (m, 1H), 1.77 (m, 1H).

EXAMPLE 215

1-(6-Chloro-2-4-[2-(4-morpholinyl)ethoxy]phenyl}-1H-imidazo[4,5-b]pyridin-7-yl)-3-pyrrolidinylformamide 1-(6-Chloro-2-{4-[2-(4-morpholinyl)ethoxy]phenyl}-1H-imidazo[4,5-b]pyridin-7-yl)-3-pyrrolidinamine (Example 214) (20 mg, 45 µmol) was added to a mixture of sodium formate (1.0 g), formic acid (10 ml) and acetic anhydride (1.0 ml) and shaken and then left standing 20 min, whereupon it was concentrated in vacuo. To the residue were added water (1 ml), TFA (0.10 ml) and acetonitrile (1.0 ml) and the resulting solution was subjected to semi-preparative HPLC-C₁₈. The appropriate fractions were pooled and evaporated in vacuo to afford the product as the bis(trifluoroacetate) (18 mg, 85%).

APCI-MS m/z: 471.6, 473.5 [MH⁺].

¹H-NMR (400 MHz, DMSO-d₆): δ 13.27 (s, 1H), 10.09 (s, 1H), 8.45 (d, J 6.2 Hz, 1H), 8.12 (d, J 9.0 Hz, 2H), 8.03 (s, 1H), 7.95 (s, 1H), 7.17 (d, J 9.0 Hz, 214), 4.44 (t, J 4.8 Hz, 2H), 4.42-4.21 (m, 3H), 4.16 (dq, J 7.7, 5.3 Hz, 1H), 4.00 (dd, J 10.9, 3.5 Hz, 3H), 3.72 (bs, 2H), 3.62 (t, J 4.3 Hz, 2H), 3.53 (bs, 2H), 3.23 (bs, 2H), 2.15 (td, J 12.9, 7.5 Hz, 1H), 1.92 (td, J 12.1, 5.0 Hz, 1H).

This salt (10 mg) was dissolved in EtOAc (5 ml) and washed with saturated aqueous NaHCO₃ (5 ml) and brine (2 ml). The organic phase was dried (MgSO₄) and evaporated in vacuo to afford the free base (6 mg).

EXAMPLE 216

6-Chloro-N-(2-ethylphenyl)-2-{4-[2-(4-morpholinyl)ethoxy]phenyl}-1H-imidazo[4,5-b]pyridin-7-amine 6,7-Dichloro-2-[4-(2-morpholin-4-ylethoxy)phenyl]-3H-imidazo[4,5-b]pyridine (Example 206) (30 mg, 76 µmol) and o-ethylaniline (0.75 ml) were mixed and heated in a microwave oven at 220° C. for 1 h. The mixture was then diluted with 4M HCl (0.75 ml) and acetonitrile (1 ml) whereupon it was subjected to semi-preparative HPLC-C₁₈. The product co-eluted with o-ethylaniline wherefore the appropriate fractions were pooled and concentrated in vacuo to give a brown oily residue which was subjected to a second preparative HPLC-C₁₈ purification. The appropriate fractions were pooled and evaporated in vacuo to provide the product as a TFA-salt (15 mg). For NMR experiments this salt was first dissolved in CDCl₃ and then diluted with EtOAc (3 ml). This solution was washed with saturated aqueous NaHCO₃ (3 ml) and brine (3 ml). The organic phase was dried (MgSO₄) and evaporated in vacuo to afford the pure product (10 mg, 27%).

APCI-MS m/z: 478.2, 480.2 [MH⁺].

¹H-NMR (300 MHz, CDCl₃): δ 8.07 (s, 1H), 8.03 (s, 1H), 7.78 (d, J 8.6 Hz, 2H), 7.44-7.36 (m, 2H), 7.31-7.26 (m, 2H), 6.90 (d, J 8.6 Hz, 2H), 4.47 (bs, 2H), 4.03-4.00 (m, 4H), 3.70-3.66 (m, 2H), 3.54 (bs, 2H), 3.09 (m, 2H), 2.67 (q, J 7.6 Hz, 2H), 1.20 (t, J 7.5 Hz, 3H).

EXAMPLE 217

6-Chloro-7-(2,3-dihydro-1H-indol-1-yl)-2-{4-[2-(4-morpholinyl)ethoxy]phenyl}-1H-imidazo[4,5-b]pyridine 6,7-Dichloro-2-[4-(2-morpholin-4-ylethoxy)phenyl]-3H-imidazo[4,5-b]pyridine (Example 206) (30 mg 76 µmol) and indoline (0.10 ml, 790 µmol) were mixed in xylene (mixture of isomers, 0.75 ml) and heated in a microwave oven at 180° C. for 20 min. When cool again, water (0.75 ml) and acetic acid (0.75 ml) were added to the mixture, causing separation of two phases. The aqueous phase was separated and subjected to semi-preparative HPLC-C₁₈. The appropriate fractions were pooled and evaporated in vacuo. The yellow oily residue was dissolved in EtOAc (20 ml). This solution was washed with 1% aqueous NaHCO₃ (20 ml) and brine (10 ml). The organic phase was dried (MgSO₄) and evaporated in vacuo to afford the pure product (31 mg, 85%) as a pale yellow powder.

APCI-MS m/z: 476.4, 478.6 [MH$^+$].

$^1$H-NMR (300 MHz, DMSO-d$_6$): δ 11.76 (s, 1H), 8.04 (s, 1H), 7.98 (d, J 8.6 Hz, 2H), 7.29 (d, J 7.1 Hz, 1H), 7.15 (t, J 7.2 Hz, 1H), 7.03 (t, J 7.1 Hz, 1H), 6.94 (d, J 8.6 Hz, 2H), 6.71 (d, J 7.9 Hz, 1H), 4.69 (bs, 2H), 4.45 (bs, 2H), 3.99 (bs, 4H), 3.66 (bs, 2H), 3.53 (t, J 3.7 Hz, 2H), 3.23 (t, J 7.5 Hz, 2H), 3.09 (bs, 2H).

EXAMPLE 218

6-Chloro-7-{4-morpholinyl)-2-{4-[2-(4-morpholinyl)ethoxy]phenyl}-1H-imidazo[4,5-b]pyridine 6,7-Dichloro-2-[4-(2-morpholin-4-ylethoxy)phenyl]-3H-imidazo[4,5-b]pyridine (Example 206) (10 mg, 25 μmol) was dissolved in morpholine (0.5 ml) and heated in a microwave oven at 180° C. for 15 min. The excess morpholine was evaporated in vacuo and the oily residue triturated with EtOAc. The crystals formed were collected by filtration and washed with a 1: I EtOAc/n-heptane mixture. This afforded the product as a white powder (5 mg, 44%).

APCI-MS m/z: 444.5, 446.5 [MH$^+$].

$^1$H-NMR (300 MHz, DMSO-d$_6$): δ 13.34 (s, 1H), 8.11 (d, J 8.8 Hz, 2H), 8.09 (s, 1H), 7.10 (d, J 8.8 Hz, 2H), 4.16 (t, J 5.8 Hz, 2H), 3.80 (m, 4H), 3.67 (t, J 4.7 Hz, 4H), 3.58 (t, J 4.7 Hz, 4H), 2.71 (t, J 5.8 Hz, 2H), 2.51-2.46 (m, 4H).

EXAMPLE 219

6-Chloro-2-[4-(2-morpholin-4-ylethoxy)phenyl]-N-pyridin-3-yl-3H-imidazo[4,5-y]pyridin-7-amine 6,7-Dichloro-2-[4-(2-morpholin-4-ylethoxy)phenyl]-3H-imidazo[4,5-b]pyridine (Example 206) (100 mg, 275 μmol), 3-aminopyridine-N-oxide (100 mg, 900 μmol) and p-toluene-sulfonic acid monohydrate (120 mg, 630 μmol) were mixed in NMP (2 ml) and heated to 190° C. overnight. The reaction mixture was allowed to cool and then subjected to semi-preparative HPLC-C$_{18}$. This afforded the product as a TFA salt, which was then stirred in an aqueous 10% NaHCO$_3$ solution for 15 min. The free base could then be isolated by filtration and washed with water to afford a brown powder (38 mg, 31%).

APCI-MS m/z: 451.3, 453.3 [MH$^+$].

$^1$H-NMR (300 MHz, DMSO-d$_6$): δ 8.68 (s, 1H), 8.44 (s, 1H), 8.20-8.05 (m, 2H), 7.90 (d, J 7.9 Hz, 2H), 7.44 (m, 1H), 7.26 (dd, J 8.1 Hz, J' 4.8 Hz, 1H), 7.05 (d, J 7.9 Hz, 2H), 4.13 (m, 2H), 3.56 (m, 4H), 2.69 (m, 2H), 2.46 (m, 4H).

EXAMPLE 220

[3-(6-Chloro-2-[4-(2-morpholin-4-ylethoxy)phenyl]-3H-imidazo[4,5-b]pyridin-7-yl}amino)phenyl]methanol By a procedure similar to that of Example 219 but using 6,7-dichloro-2-[4-(2-morpholin-4-ylethoxy)phenyl]-3H-imidazo[4,5-b]pyridine (Example 206) and (3-aminophenyl)methanol, the title compound was obtained in 48% yield.

APCI-MS m/z: 480.4, 482.3 [MH$^+$].

$^1$H-NMR (400 MHz, DMSO-d$_6$): δ 13.29 (s, 1H), 8.44 (s, 1H), 8.14 (s, 1H), 7.97 (d, J 8.8 Hz, 2H), 7.18 (t, J 7.8 Hz, 01H), 7.12 (s, 1H), 7.06 (d, J 8.9 Hz, O$_2$H), 6.99-6.93 (m, 02H), 5.10 (t, J 5.7 Hz, 1H), 4.45 (d, J 5.7 Hz, 2H), 4.15 (t, J 5.7 Hz, 2H), 3.58 (t, J 4.6 Hz, 4H), 2.70 (t. J 5.7 Hz, 2H), 2.52-2.45 (m, 4H).

EXAMPLE 221

6-Chloro-N-(2-fluorophenyl)-2-[4-(2-morpholin-4-ylethoxy)phenyl]-3H-imidazo[4,5-b]pyridin-7-amine By a procedure similar to that of Example 219 but using 6,7-dichloro-2-[4-(2-morpholin-4-ylethoxy)phenyl]-3H-imidazo[4,5-b]pyridine (Example 206) and 2-flouroaniline, the title compound was obtained in 56% yield.

APCI-MS m/z: 468.1, 470.1 [MH$^+$].

$^1$H-NMR (400 MHz, DMSO-d$_6$): δ 13.15 (s, 1H), 8.32 (s, 1H), 8.08 (s, 1H), 7.82 (d, J 7.8 Hz, 2H), 7.34 (t, J 7.6 Hz, 1H), 7.22-7.10 (m, 3H), 7.02 (d, J 8.4 Hz, 2H), 4.13 (t, J 5.7 Hz, 2H), 3.57 (t, J 4.6 Hz, 4H), 2.69 (t, J 5.8 Hz, 2H), 2.46 (t, J 4.4 Hz, 4H).

EXAMPLE 222

6-Chloro-2-{4-[2-(4-morpholinyl)ethoxy]phenyl}-N-phenyl-1H-imidazo[4,5-b]pyridin-7-amine By a procedure similar to that of Example 219 but using 6,7-dichloro-2-[4-(2-morpholin-4-ylethoxy)phenyl]-3H-imidazo[4,5-b]pyridine (Example 206) and aniline, the title compound was obtained in 44% yield.

APCI-MS m/z: 450.3, 452.2 [MH$^+$].

$^1$H-NMR (400 MHz, DMSO-d$_6$): δ 8.43 (s, 1H), 8.13 (s, 1H), 7.94 (d, J 8.5 Hz, 2H), 7.23 (t, J 11.8 Hz, 2H), 7.09-7.03 (m, 4H), 6.96 (t, J 7.3 Hz, 1H), 4.13 (t, J 5.8 Hz, 2H), 3.56 (t, J 4.6 Hz, 4H), 2.68 (t, J 5.7 Hz, 2H), 2.45 (t, J 4.4 Hz, 4H).

EXAMPLE 223

6-Chloro-N-(3-ethylphenyl)-2-{4-[2-(4-morpholinyl)ethoxy]phenyl}-1H-imidazo[4,5-b]pyridin-7-amine By a procedure similar to that of Example 219 but using 6,7-dichloro-2-[4-(2-morpholin-4-ylethoxy)phenyl]-3H-imidazo[4,5-b]pyridine (Example 206) and 3-ethylaniline, the title compound was obtained in 49% yield.

APCI-MS m/z: 478.3, 480.3 [MH$^+$].

$^1$H-NMR (400 MHz, DMSO-d$_6$): δ 8.36 (s, 1H), 8.13 (s, 1H), 7.96 (d, J 8.7 Hz, 2H), 7.13 (t, J 7.7 Hz, 1H), 7.04 (d, J 8.8 Hz, 2H), 7.00-6.87 (m, 2H), 6.82 (d, J 7.5 Hz, 1H), 4.13 (t, J 5.7 Hz, 2H), 3.56 (t, J 4.6 Hz, 4H), 2.68 (t, J 5.7 Hz, 2H), 2.52 (q, J 7.7 Hz, 2H), 2.45 (t, J 8.7 Hz, 4H), 1.13 (t, J 7.6 Hz, 3H).

EXAMPLE 224

2-[Benzyl(6-chloro-2-{4-[2-(4-morpholinyl)ethoxy]phenyl)-1H-imidazo[4,5-b]pyridin-7-yl)amino]ethanol 6,7-Dichloro-2-[4-(2-morpholin-4-ylethoxy)phenyl]-3H-imidazo[4,5-b]pyridine (Example 206) (0.10 g, 0.25 mmol) and N-benzylethanolamine (0.3 g) were heated to 180° C. for 15 h. The reaction mixture was diluted with CH$_3$CN and purified by HPLC-C$_{18}$ to deliver the title product as the bis (trifluoroacetate) (44%).

APCI-MS m/z: 508.1, 510.1 [MH$^+$].

$^1$H-NMR (400 MHz, DMSO-d$_6$): δ 8.16 (d, J 9.0 Hz, 2H), 8.09 (s, 1H), 7.35 (d, J 7.3 Hz, 2H), 7.26-7.14 (m, 5H), 5.05 (s, 2H), 4.44 (t, J 4.5 Hz, 2H), 3.98 (bs, 4H), 3.70 (t, J 6.3 Hz, 2H), 3.64-3.57 (m, 4H), 3.23 (bs, 4H).

EXAMPLE 225

2-[(6-Chloro-2-4-[2-(4-morpholinyl)ethoxy]phenyl}-1H-imidazo[4,5-b]pyridin-7-yl)amino]ethanol 2-[Benzyl(6-chloro-2-{4-[2-(4-morpholinyl)ethoxy]phenyl}-1H-imidazo[4,5-b]pyridin-7-yl)amino]ethanol (Example 224) (0.05 g, 0.07 mmol) was dissolved in 48% aqueous HBr (0.5 ml) and heated at 100° C. for 4 min. The reaction mixture was neutralized with NaHCO$_3$ (s) and diluted with CH$_3$CN (2 ml) and purified by HPLC-C$_{18}$, giving the title product as the bis(trifluoroacetate) (22%).

APCI-MS m/z: 418.2, 420.3 [MH$^+$].

$^1$H-NMR (400 MHz, DMSO-d$_6$): δ 8.12 (d, J 8.7 Hz, 2H), 8.03 (s, 1H), 7.16 (d, J 8.9 Hz, 2H), 4.43 (t, J 4.8 Hz, 2H), 4.16 (d, J 5.3 Hz, 2H), 3.97 (bs, 4H), 3.68 (t, J 5.9 Hz, 2H), 3.60 (t, J 4.4 Hz, 2H), 3.23 (bs, 4H).

EXAMPLE 226

N-Benzyl-6-chloro-N-methyl-2-{4-[2-(4-morpholinyl)ethoxy]phenyl}-1H-imidazo[4,5-b]pyridin-7-amine 6,7-Dichloro-2-[4-(2-morpholin-4-ylethoxy)phenyl]-3H-imidazo[4,5-b]pyridine (Example 206) (0.10 g, 0.25 mmol) and N-methylbenzylamine (0.7 ml) were heated to 180° C. for 3 h. The reaction mixture was diluted with diethyl ether (15 ml) and extracted with 2M HCl (40 ml). The aqueous phase was basified with 10M NaOH and extracted with EtOAc. The organic phase was evaporated in vacuo and the oily residue became crystalline. The crystals were washed with tert-butyl methyl ether to afford the pure product (42%).

APCI-MS m/z: 478.3, 480.3 [MH$^+$].

$^1$H-NMR (400 MHz, DMSO-d$_6$): δ 8.11-8.08 (m, 3H), 7.39 (d, J 7.4 Hz, 2H), 7.31 (t, J 7.5 Hz, 2H), 7.22 (t, J 7.1 Hz, 1H), 7.09 (d, J 8.7 Hz, 2H), 4.95 (s, 2H), 4.16 (t, J 5.7 Hz, 2H), 3.57 (t, J 4.5 Hz, 4H), 3.17 (s, 3H), 2.70 (t, J 5.7 Hz, 2H), 2.48-2.45 (m, 4H).

EXAMPLE 227

6-Chloro-N-methyl-2-{4-[2-(4-morpholinyl)ethoxy]phenyl I-1H-imidazo[4,5-b]pyridin-7-amine N-Benzyl-6-chloro-N-methyl-2-{4-[2-(4-morpholinyl)ethoxy]phenyl}-1H-imidazo[4,5-b]pyridin-7-amine (Example 226) (0.04 g, 0.08 mmol) was dissolved in 48% aqueous HBr (0.5 ml) and heated at 110° C. for 4 min. The reaction mixture was neutralized with NaHCO$_3$ (s) and crystals were formed. The crystals were collected by filtration and washed with water. This afforded the title product as a white powder (65%).

APCI-MS m/z: 388.2, 390.3 [MH$^+$].

$^1$H-NMR (400 MHz, DMSO-d$_6$): δ 13.02 (s, 1H), 8.03 (d, J 8.9 Hz, 2H), 7.84 (s, 1H), 7.05 (d, J 8.9 Hz, 2H), 6.35 (q, J 4.9 Hz, 1H), 4.12 (t, J 5.7 Hz, 2H), 3.55 (t, J 4.6 Hz, 4H), 3.51 (d, J 5.1 Hz, 3H), 2.68 (t, J 5.1 Hz, 2H), 2.48-2.45 (m, 4H).

EXAMPLE 228

7-(Benzylthio)-6-chloro-2-{4-[2-(4-morpholinyl)ethoxy]phenyl}-1H-imidazo[4,5-b]pyridine 6,7-Dichloro-2-[4-(2-morpholin-4-ylethoxy)phenyl]-3H-imidazo[4,5-b]pyridine (Example 206) (0.10 g, 0.25 mmol), benzyl mercaptan (0.036 ml, 0.3 mmol) and potassum tert-butanolate (0.071 g, 0.63 mmol) were dissolved in DMF (1 ml) and heated to 80° C. for 48 h. The reaction mixture was diluted with EtOAc and extracted with 2M HCl. The aqueous phase was basified with 10M NaOH and extracted with EtOAc. The organic phase was dried (Na$_2$SO$_4$) and evaporated in vacuo and the residue was dissolved in CH$_3$CN (3 ml) and purified by HPLC-C$_{18}$, giving the title product as a bis (trifluoroacetate) (37%).

APCI-MS m/z: 481.1, 483.0 [MH$^+$].

$^1$H-NMR (400 MHz, DMSO-d$_6$): δ 8.25 (d, J 8.9 Hz, 2H), 8.19 (s, 1H), 7.37 (d, J 7.2 Hz, 2H), 7.28-7.17 (m, 5H), 5.18 (s, 2H), 4.45 (t, J 4.6 Hz, 2H), 3.97 (bs, 4H), 3.61 (s, 2H), 3.29 (bs, 4H).

EXAMPLE 229

6-Chloro-N-[4-(methylsulfonyl)phenyl]-2-{4-[2-(4-morpholinyl)ethoxy]phenyl}-1H-imidazo[4,5-b]pyridin-7-amine 6,7-Dichloro-2-[4-(2-morpholin-4-ylethoxy)phenyl]-3H-imidazo[4,5-b]pyridine (Example 206) (0.02 g, 0.05 mmol) and 4-(methylsulfonyl)aniline (0.1 g) were dissolved in o-dichlorobenzene (0.7 ml) and 4 drops of concentrated HCl were added and the reaction mixture was heated in a microwave oven at 180° C. for 10 min. The reaction mixture was diluted with tert-butyl methyl ether (5 ml) and extracted with 2M HCl (10 ml). The aqueous phase was basified with 10M NaOH and extracted with EtOAc. The organic phase was evaporated in vacuo and the residue was dissolved in CH$_3$CN (2 ml) and purified by HPLC-C is, giving the title product (7 mg, 26%).

APCI-MS m/z: 528.3, 530.2 [MH$^+$].

$^1$H-NMR (400 MHz, DMSO-d$_6$): δ 9.18 (s, 1H), 8.26 (s, 1H), 8.02 (d, J 8.6 Hz, 2H), 7.71 (d, J 8.8 Hz, 2H), 7.12-7.06 (m, 4H), 4.14 (t, J 5.7 Hz, 2H), 3.56 (t, J 4.6 Hz, 4H), 3.13 (s, 3H), 2.69 (t, J 5.7 Hz, 2H), 2.46 (t, J 4.6 Hz, 4H).

EXAMPLE 230

6-Chloro-2-4-[2-(4-morpholinyl)ethoxy]phenyl}-N-[4-(4-morpholinyl)phenyl]-1H-imidazo[4,5-b]pyridin-7-amine 6,7-Dichloro-2-[4-(2-morpholin-4-ylethoxy)phenyl]-3H-imidazo[4,5-b]pyridine (Example 206) (0.020 g, 0.051 mmol) and (4-morpholin-4-ylphenyl)amine (0.1 g) were heated to 180° C. for 2 h. The reaction mixture was diluted with tert-butyl methyl ether (5 ml) and extracted with 2M HCl (20 ml). The aqueous phase was basified with 10M NaOH and extracted with EtOAc. The organic phase was evaporated in vacuo and the residue was dissolved in CH$_3$CN (2 ml) and purified by HPLC-C$_{18}$, giving the title product (6 mg, 22%).

APCI-MS m/z: 535.3, 537.3 [MH$^+$].

$^1$H-NMR (400 MHz, DMSO-d$_6$): δ 8.15 (s, 1H), 8.04 (s, 1H), 7.91 (d, J 8.8 Hz, 2H), 7.09-6.99 (m, 4H), 6.86 (d, J 9.0 Hz, 2H), 4.13 (t, J 5.7 Hz, 2H), 3.74 (t, J 4.7 Hz, 4H), 3.56 (t, J 4.6 Hz, 4H), 3.06 (t, J 4.7 Hz, 4H), 2.68 (t, J 5.7 Hz, 2H), 2.46 (t, J 4.5 Hz, 4H).

EXAMPLE 231

N'-(6-Chloro-2-{4-[2-(4-morpholinyl)ethoxy]phenyl}-1H-imidazo[4,5-b]pyridin-7-yl)-N,N-diethyl-1,4-benzenediamine 6,7-Dichloro-2-[4-(2-morpholin-4-ylethoxy)phenyl]-3H-imidazo[4,5-b]pyridine (Example 206) (0.020 g, 0.051 mmol) and N,N-diethyl-1,4-phenylenediamine (0.1 g) were heated to 180° C. for 2 h. The reaction mixture was diluted with tert-butyl methyl ether (5 ml) and extracted with 2M HCl (20 ml). The aqueous phase was basified with 10M NaOH and extracted with EtOAc. The organic phase was evaporated in vacuo and the residue was dissolved in CH₃CN (2 ml) and purified by HPLC-C₁₈, giving the title product (56%).

APCI-MS m/z: 521.2, 523.2 [MH⁺].

¹H-NMR (400 MHz, DMSO-d₆): δ 8.00 (s, 1H), 7.99 (s, 1H), 7.89 (d, J 8.8 Hz, 2H), 7.02 (d, J 8.9 Hz, 2H), 6.97 (d, J 8.9 Hz, 2H), 6.63 (d, J 9.0 Hz, 2H), 4.12 (t, J 5.7 Hz, 2H), 3.56 (t, J 4.6 Hz, 4H), 3.33-3.29 (m, 4H), 2.68 (t, J 5.7 Hz, 2H), 2.45 (t, J 4.5 Hz, 4H), 1.10 (t, J 7.0 Hz, 6H).

EXAMPLE 232

N-{4-[(6-Chloro-2-4-[2-(4-morpholinyl)ethoxy]phenyl}-1H-imidazo[4,5-b]pyridin-7-yl)amino]phenyl}acetamide 6,7-Dichloro-2-[4-(2-morpholin-4-ylethoxy)phenyl]-3H-imidazo[4,5-b]pyridine (Example 206) (0.020 g, 0.051 mmol) and 4-aminoacetanilide (0.1 g) were heated to 180° C. for 2 h. The reaction mixture was diluted with diethyl ether (5 ml) and extracted with 2M HCl (20-ml). The aqueous phase was basified with 10M NaOH and extracted with EtOAc. The organic phase was evaporated in vacuo and the residue was dissolved in CH₃CN (2 ml) and purified by HPLC-C₁₈, giving the title product as the bis(trifluoroacetate) (5 mg, 13%).

APCI-MS m/z: 507.3, 509.2 [MH⁺].

¹H-NMR (400 MHz, DMSO-d₆): δ 9.83 (s, 1H), 8.37 (s, 1H), 8.13 (s, 1H), 7.98 (d, J 8.8 Hz, 2H), 7.45 (d, J 8.8 Hz, 2H), 7.12 (d, J 8.9 Hz, 2H), 7.07 (d, J 8.8 Hz, 2H), 4.41 (t, J 4.5 Hz, 2H), 4.03-3.91 (m, 4H), 3.55-3.45 (m, 2H), 3.27-3.12 (m, 4H), 2.02 (s, 3H).

EXAMPLE 223

6-Chloro-2-{4-[2-(4-morpholinyl)ethoxy]phenyl)□-7-phenoxy-1H-imidazo[4,5-b]pyridine 6,7-Dichloro-2-[4-(2-morpholin-4-ylethoxy)phenyl]-3H-imidazo[4,5-b]pyridine (Example 206) (0.030 g, 0.076 mmol) and phenol (0.3 g) were heated to 180° C. for 15 h. The reaction mixture was diluted with CH₃CN and aqueous NH₃, and purified by HPLC-C₁₈, giving the title product (0.015 g, 44%).

APCI-MS m/z: 451.2, 453.3 [MH⁺].

¹H-NMR (400 MHz, DMSO-d₆): δ 8.39 (s, 1H), 8.03 (d, J 8.3 Hz, 2H), 7.36-7.32 (m, 2H), 7.11 (t, J 7.4 Hz, 1H), 7.07 (d, J 8.9 Hz, 2H), 6.98 (d, J 7.9 Hz, 2H), 4.14 (t, J 5.7 Hz, 2H), 3.56 (t, J 4.6 Hz, 4H), 2.69 (t, J 5.7 Hz, 2H), 2.46 (t, J 4.5 Hz, 4H).

EXAMPLE 234

6-Chloro-2-{4-[2-(4-morpholinyl)ethoxy]phenyl}-7-[2-(1-pyrrolidinyl)ethoxy]-1H-imidazo[4,5-b]pyridine 6,7-Dichloro-2-[4-(2-morpholin-4-ylethoxy)phenyl]-3H-imidazo[4,5-b]pyridine (Example 206) (0.010 g, 0.025 mmol), 1-(2-hydroxyethyl)pyrrolidine (0.5 ml) and sodium hydride were heated to 120° C. for 3 h. The reaction mixture was diluted with CH₃CN and purified by HPLC-C₁₈, giving the title product (0.006 g, 50%)

APCI-MS m/z: 472.2, 474.3 [MH⁺].

¹H-NMR (400 MHz, DMSO-d₆): δ 8.14-8.10 (m, 3H), 7.11 (d, J 8.9 Hz, 2H), 5.19 (t, J 5.2 Hz, 2H), 4.16 (t, J 5.7 Hz, 2H), 3.57 (t, J 4.6 Hz, 4H), 2.89 (t, J 5.8 Hz, 2H), 2.71 (t, J 5.7 Hz, 2H), 2.55 (t, J 5.5 Hz, 4H), 2.48-2.46 (m, 4H), 1.66 (quintet, J 3.3 Hz, 4H).

EXAMPLE 235

6-Chloro-2-[4-(2-morpholin-4-ylethoxy)phenyl]-N-(2-morpholin-4-ylethyl)-3H-imidazo[4,5-b]pyridin-7-amine 6,7-Dichloro-2-[4-(2-morpholin-4-ylethoxy)phenyl]-3H-imidazo[4,5-b]pyridine (Example 206) (0.010 g, 0.025 mmol) was dissolved in 2-morpholin-4-ylethanamine (1 ml, 8 mmol) and heated in a sealed vial at 180° C. for 40 min. The excess amine was removed under reduced pressure, and the solid residue was washed with methanol, giving the title product (0.005 g, 41%).

APCI-MS m/z: 487 [MH⁺].

¹H-NMR (DMSO-d₆): δ 13.0 (1H, bs), 8.06 (2H, d), 7.89 (1H, s), 7.09 (2H, d), 6.24 (1H, bs), 4.22-4.14 (4H, m), 3.59 (8H, t), 2.74-2.60 (2H, m), 2.65-2.60 (2H, m), 2.54-2.44 (8H, m).

EXAMPLE 236

6-Chloro-2-[4-(2-morpholin-4-ylethoxy)phenyl]-7-pyrrolidin-1-yl-3H-imidazo[4,5-b]pyridine 6,7-Dichloro-2-[4-(2-morpholin-4-ylethoxy)phenyl]-3H-imidazo[4,5-b]pyridine (Example 206) (0.010 g, 0.025 mmol) and pyrrolidine (0.03 ml, 0.4 mmol) were dissolved in DMF (1 ml) and heated in a sealed vial at 150° C. for 3 h. The excess amine and the solvent were removed under reduced pressure, and the solid residue was washed with CH₃CN, giving the title product (0.002 g, 19%).

APCI-MS m/z: 428 [MH⁺].

¹H-NMR (DMSO-d₆): δ 13.1 (1H, bs), 8.06 (2H, d), 7.89 (1H, s), 7.08 (2H, d), 4.16 (2H, t), 4.10 (4H, t), 3.59 (4H, t), 2.71 (2H, t), 2.51-2.47 (4H, m), 1.92 (4H, q).

EXAMPLE 237

6-Chloro-2-[4-(2-morpholin-4-ylethoxy)phenyl]-N-(1-phenylethyl)-3H-imidazo[4,5-b]pyridin-7-amine 6,7-Dichloro-2-[4-(2-morpholin-4-ylethoxy)phenyl]-3H-imidazo[4,5-b]pyridine (Example 206) (0.030 g, 0.072 mmol) was dissolved in 1-phenylethylamine (1 ml, 7.83 mmol) and heated in a sealed vial at 200° C. for 2 h. The excess amine was removed under reduced pressure, and the solid residue was washed with diethyl ether, NH₃ (28% in water) and CH₃CN, giving the title product (0.018 g, 52%).

APCI-MS m/z: 478 [MH⁺].

¹H-NMR (DMSO-d₆): δ 8.09 (2H, d), 7.92 (1H, s), 7.50 (2H, d), 7.27 (2H, t), 7.16-7.09 (4H, m), 6.63-6.58 (1H, m), 6.31 (1H, d), 4.17 (2H, t), 3.59 (4H, t), 2.72 (2H, t), 2.51-2.47 (4H, m), 1.63 (3H, d).

EXAMPLE 238

6-Chloro-7-(4-methylphenyl)-2-[4-(2-morpholin-4-ylethoxy)phenyl]-3H-imidazo[4,5-b]pyridine 6,7-Dichloro-2-[4-(2-morpholin-4-ylethoxy)phenyl]-3H-imidazo[4,5-b]pyridine (Example 206) (0.050 g, 0.13 mmol), 4-methylphenylboronic acid (0.027 g, 0.19 mmol), K₂CO₃ (0.097 g, 0.70 mmol) and Pd(PPh₃)₄ (0.029 g, 0.025 mmol) were mixed in a vial. Dioxane (3 ml) was added and the reaction mixture was heated to 100° C. under argon for 4 h. EtOAc (50 ml) was added and the solution was washed with water. Drying (Na₂SO₄) and evaporation gave crude material which was purified by column chromatography (dichloromethane/methanol, 95:5), giving the title product (0.019 g, 33%).

APCI-MS m/z: 449 [MH$^+$].

$^1$H-NMR (DMSO-d$_6$): δ 13.60 (1H, br.s), 8.39 (1H, s), 8.09 (2H, d), 7.57 (2H, d), 7.37 (2H, d), 7.09 (2H, d), 4.17 (2H, t), 3.58 (4H, t), 2.71 (2H, t), 2.50-2.47 (4H, m), 2.47 (3H, s).

EXAMPLE 239

6-Chloro-7-(3-methoxyphenyl)-2-[4-(2-morpholin-4-ylethoxy)phenyl]-3H-imidazo[4,5-b]pyridine By a procedure similar to Example 238 but using 3-methoxyphenylboronic acid, the title compound was prepared. Purification was achieved by recrystallization (CH$_3$CN).

APCI-MS m/z: 465 [MH$^+$].

$^1$H-NMR (DMSO-d$_6$): δ 13.60 (1H, bs), 8.40 (1H, s), 8.11 (2H, d), 7.49 (1H, t), 7.23-7.16 (3H, m), 7.09 (2H, d), 4.17 (2H, t), 3.83 (3H, s), 3.58 (4H, t), 2.71 (2H, t), 2.50-2.47 (4H, m).

EXAMPLE 240

N-(3-6-Chloro-2-[4-(2-morpholin-4-ylethoxy)phenyl]-3H-imidazo[4,5-b]pyridin-7-yl}phenyl)acetamide By a procedure similar to Example 238 but using 3-(acetylamino)phenylboronic acid, the title compound was prepared. Purification was achieved by recrystallization (CH$_3$CN).

APCI-MS m/z: 492 [MH$^+$].

$^1$H-NMR (DMSO-d$_6$): δ 10.1 (1H, s), 8.39 (1H, s), 8.12 (2H, d), 7.81-7.75 (2H, m), 7.48 (1H, t), 7.28 (1H, d), 7.09 (2H, d), 4.16 (2H, t), 3.58 (4H, t), 2.71 (2H, t), 2.50-2.46 (4H, m), 2.07 (3H, s).

EXAMPLE 241

6-Chloro-2-[4-(2-morpholin-4-ylethoxy)phenyl]-7-thien-3-yl-3H-imidazo[4,5-b]pyridine By a procedure similar to Example 238 but using thien-3-ylboronic acid, the title compound was prepared.

APCI-MS m/z: 441 [MH$^+$].

$^1$H-NMR (DMSO-d$_6$): δ 10.0 (1H, bs), 8.41 (1H, s), 8.26-8.18 (3H, m), 7.77-7.73 (2H, m), 7.20 (2H, d), 4.46 (2H, t), 4.04-3.94 (2H, m), 3.78-3.66 (2H, m), 3.62 (2H, bs), 3.58-3.50 (2H, m), 3.30-3.18 (2H, m).

EXAMPLE 242

2-[4-(2-Morpholin-4-ylethoxy)phenyl]-3H-imidazo[4,5-b]pyridine 6,7-dicarbonitrile 6,7-Dichloro-2-[4-(2-morpholin-4-ylethoxy)phenyl]-3H-imidazo[4,5-b]pyridine (Example 206) (0.021 g, 0.053 mmol), Zn(CN)$_2$ (0.0055 g, 0.047 mmol), Pd$_2$(dba)$_3$ (0.012 g, 0.013 mmol) and dppf (0.012 g, 0.022 mmol) were mixed in a vial. DMF (2 ml) was added and the reaction mixture was heated to 120° C. under argon for 3 h. EtOAc (20 ml) was added and the solution was washed with water. Drying (Na$_2$SO$_4$) and evaporation delivered crude material which was purified by HPLC-C$_{18}$, giving the title product (0.002 g, 10%).

APCI-MS m/z: 375 [MH$^+$].

EXAMPLE 243

7-Chloro-2-[4-(2-morpholin-4-ylethoxy)phenyl]-3H-imidazo[4,5-b]pyridine-6-carbonitrile 6,7-Dichloro-2-[4-(2-morpholin-4-ylethoxy)phenyl]-3H-imidazo[4,5-b]pyridine (Example 206) (0.063 g, 0.16 mmol), Zn(CN)$_2$ (0.018 g, 0.153 mmol), Pd$_2$(dba)$_3$ (0.036 g, 0.039 mmol) and dppf (0.036 g, 0.065 mmol) were mixed in a vial. DMF (6 ml) was added and the reaction mixture was heated to 120° C. under argon for 3 h. EtOAc (50 ml) was added and the solution was washed with water. Drying (Na$_2$SO$_4$) and evaporation delivered crude material which was purified by HPLC-C$_{18}$, giving the title product (0.015 g, 24%).

APCI-MS m/z: 384 [MH$^+$].

$^1$H-NMR (400 MHz, DMSO-d$_6$): δ 10.1 (1H, bs), 8.56 (1H, s), 8.29 (2H, d), 7.25 (2H, d), 4.49 (2H, t), 4.08-3.94 (2H, m), 3.78-3.66 (2H, m), 3.62 (2H, bs), 3.58-3.48 (2H, m), 3.30-3.18 (2H, m).

EXAMPLE 244

7-Anilino-2-(4-{2-[(2-methoxyethyl)(methyl)amino]ethoxy}phenyl)-3H-imidazo[4,5-b]pyridine-6-carbonitrile 7-Chloro-2-[4-(2-morpholin-4-ylethoxy)phenyl]-3H-imidazo[4,5-b]pyridine-6-carbonitrile (Example 243) (0.050 g, 0.13 mmol) was dissolved in aniline (2 ml) and heated at 180° C. for 3 h in a sealed vial. The excess aniline was evaporated and the crude product was purified by HPLC-C$_{18}$, giving the title product (0.001 g, 2%).

APCI-MS m/z: 441 [MH$^+$].

$^1$H-NMR (400 MHz, DMSO-d$_6$): δ 9.97 (1H, bs), 9.24 (1H, s), 8.32 (1H, s), 8.08 (2H, d), 7.33 (2H, t), 7.26 (2H, d), 7.12-7.21 (3H, m), 4.44 (2H, t), 4.06-3.93 (2H, m), 3.76-3.65 (2H, m), 3.61 (2H, bs), 3.57-3.58 (2H, m), 3.27-3.15 (2H, m).

EXAMPLE 245

6-Bromo-2-[4-(2-morpholin-4-ylethoxy)-3-nitrophenyl]-3H-imidazo[4,5-b]pyridine

5-Bromopyridine-2,3-diamine (0.5 g, 2.7 mmol) and 4-(2-morpholin-4-ylethoxy)-3-nitrobenzoic acid (1.0 g, 2.7 mmol) were dissolved in POCl$_3$ (10 ml) and heated to 105° C. for 10 h. The excess of POCl$_3$ was evaporated off, the residue was dissolved in EtOAc and aqueous NaHCO$_3$ and the aqueous phase was basified with 10M KOH. The aqueous phase was extracted three times with EtOAc. The combined organic phases were washed with brine, dried (Na$_2$SO$_4$) and evaporated in vacuo. The residue was purified by HPLC-C$_{18}$, giving the title product as a bis(trifluoroacetate (0.02 g, 1%).

APCI-MS m/z: 448.01450.1 [MH$^+$].

$^1$H-NMR (400 MHz, DMSO-d$_6$): δ 8.80 (s, 1H), 8.53 (d, J 9.0 Hz, 1H), 8.45 (s, 1H), 8.32 (s, 1H), 7.68 (d, J 9.0 Hz, 1H), 4.67 (t, J 4.3 Hz, 2H), 4.09-3.92 (m, 2H), 3.78-3.61 (m, 4H), 3.58-3.48 (m, 2H), 3.34-3.22 (m, 2H).

a) 4-(2-Morpholin-4-ylethoxy)-3-nitrobenzoic acid

Methyl 4-(2-morpholin-4-ylethoxy)benzoate (Example 206c) (30 g, 110 mmol) was dissolved in conc. sulfuric acid (70 ml) and cooled to 0° C. Nitric acid (d=1.52, 4.7 ml, 110 mmol) was added and the mixture was allowed to assume room temperature within 1 h. The reaction mixture was poured onto an ice water mixture (600 g) whereupon crystals formed. The crystals were collected by filtration and washed with water to give the pure product as a white powder (25 g, 80%).

APCI-MS m/z: 297.0 [MH+].

$^1$H-NMR (400 MHz, DMSO-$d_6$): δ 9.94 (s, 1H), 8.38 (d, J 2.1 Hz, 1H), 8.20 (dd, J 8.8, 2.1 Hz. 1H), 7.51 (d, J 9.0 Hz, 1H), 4.66-4.63 (m, 2H), 3.98 (d, J 12.2 Hz, 2H), 3.73-3.62 (m, 4H), 3.52 (d, J 12.2 Hz, 2H), 3.25 (t, J 10.7 Hz, 2H).

EXAMPLE 246

6,7-Dichloro-2-4-[2-(4-morpholinyl)ethoxy]-3-nitrophenyl}-1H-imidazo[4,5-b]pyridine 6,7-Dichloro-2-[4-(2-morpholin-4-ylethoxy)phenyl]-3H-imidazo[4,5-b]pyridine (Example 206) (393 mg, 1 mmol) was dissolved in conc. sulfuric acid (5 ml) and cooled to 5° C. Nitric acid (d=1.52, 0.10 ml, 2 mmol) was added and the mixture was allowed to assume room temperature (30 min) whereupon it was poured onto an ice/water mixture (100 g). The resulting solution was neutralized with $K_2CO_3$ (s) (pH 8). The crystals formed were collected and suspended in acetone (100 ml) and filtered. The filtrate was evaporated in vacuo and the residue was suspended in hot water and the product collected by filtration and washed with water and dried in vacuo. This yielded 75 mg (17%) of an off-white powder.

APCI-MS m/z: 438.0, 440.0 [MH+].

$^1$H-NMR (400 MHz, DMSO-$d_6$): δ 8.71 (d, J 1.7 Hz, 1H), 8.46 (d, J 10.5 Hz, 1H), 8.41 (s, 1H), 7.59 (d, J 9.0 Hz, 1H), 4.37 (t, J 5.5 Hz, 2H), 3.54 (t, J 4.4 Hz, 4H), 2.74 (t, J 5.5 Hz, 2H), 2.47 (m, 4H).

EXAMPLE 247

5-(6,7-Dichloro-1H-imidazo[4,5-b]pyridin-2-yl)-2-[2-(4-morpholinyl)ethoxy]aniline 6,7-Dichloro-2-{4-[2-(4-morpholinyl)ethoxy]-3-nitrophenyl}-1H-imidazo[4,5-b]pyridine (Example 246) (200 mg), zinc powder (200 mg) and anhydrous $CaCl_2$ (500 mg) were mixed in 95% EtOH (20 ml) and heated (70° C., 4 h). The reaction mixture was allowed to cool and then filtered and evaporated in vacuo. The residue was dissolved in acetonitrile and subjected to semi-preparative HPLC-$C_{18}$. The appropriate fraction was evaporated in vacuo and the residue dissolved in EtOAc (5 ml). This solution was washed with saturated aqueous $NaHCO_3$ (5 ml) and brine (2 ml). The organic phase was dried ($MgSO_4$) and evaporated in vacuo to afford the pure product (2 mg, 1%).

APCI-MS m/z: 408.2, 410.2 [MH+].

$^1$H-NMR (400 MHz, DMSO-$d_6$): δ 13.71 (s, 1H), 8.38 (s, 1H), 7.61 (d, J 2.4 Hz, 1H), 7.42 (d, J 8.1 Hz, 1H), 6.99 (d, J 8.9 Hz. 1H), 5.02 (s, 2H), 4.15 (t, J 5.7 Hz, 2H), 3.58 (t, J 4.6 Hz, 4H), 2.74 (t, J 5.7 Hz, 2H), 2.49 (m, 4H).

EXAMPLE 248

4-(6-Chloro-7-methyl-3H-imidazo[4,5-b]pyridin-2-yl)-2-nitrophenol 2,3-Diamino-5-chloro-4-methylpyridine (prepared by a method similar to Example 206a) (3.2 g, 20.3 mmol), was dissolved in acetonitrile (150 ml). 4-Hydroxy-3-nitrobenzaldehyde (3.1 g) was added, followed by p-toluenesulfonic acid monohydrate (0.7 g) and the resulting mixture was heated to reflux overnight. The solvent was then removed in vacuo and the residue dissolved in a mixture of dichloromethane and methanol (1:1). To this solution was added silica gel and the solvents were evaporated in vacuo. The silica-supported product mixture was then applied to column chromatography, eluting with first dichloromethane and then a mixture of dichloromethane and methanol 4:1. This afforded the title compound of approx. 75% purity. This material was suspended in hot EtOAc and filtered while still hot. The collected solid was approx. 95% pure. An analytical sample was prepared by semi-preparative HPLC-$C_{18}$.

APCI-MS m/z: 305.2, 307.3 [MH+].

EXAMPLE 249

2-Amino-5-(6-chloro-7-methyl-3H-imidazo[4,5-b]pyridin-2-yl)phenol 5-(6-Chloro-7-methyl-3H-imidazo[4,5-b]pyridin-2-yl)-2-nitrophenol (Example 248) (0.50 g, 1.6 mmol) was dissolved in warm methanol (100 ml). A catalytic amount of Raney-Nickel was added. The mixture was shaken for 2 h under hydrogen pressure (3 atm). The catalyst was filtrated off and washed. Purification by HPLC-$C_{18}$ gave the title product.

APCI-MS m/z: 275.0, 277.0 [MH+].

$^1$H-NMR (400 MHz, DMSO-$d_6$): δ 9.84 (s, 1H), 8.31 (s, 1H), 7.62 (d, J 1.7 Hz, 1H), 7.56 (dd. J 8.2; 1.7 Hz, 1H), 6.85 (d, J 8.3 Hz, 1H), 2.62 (s, 3H).

a) 5-(6-Chloro-7-methyl-3H-imidazo[4,5-b]pyridin-2-yl)-2-nitrophenol

5-Chloro-4-methylpyridine-2,3-diamine (prepared by a method similar to Example 206a) (2.0 g, 12.7 mmol) was dissolved in DMF (40 ml) and heated to 100° C. 3-Hydroxy-4-nitrobenzaldehyde (2.10 g, 12.7 mmol) dissolved in DMF (10 ml) was added slowly (10 min). Air was bubbled through the reaction mixture. After 16 h, the DMF was evaporated off and the residue was purified by column chromatography (EtOAc/methanol, 10:1) giving the title compound (0.7 g, 18%).

APCI-MS m/z: 305.0, 307.0 [MH+].

b) 5-Chloro-4-methylpyridine-2,3-diamine

The title compound was prepared by reduction of 2-amino-5-chloro-4-methyl-3-nitropyridine (prepared according to the route described in Example 206) using Raney Nickel as described above.

APCI-MS m/z: 158.0 [MH+].

EXAMPLE 250

5-(6-Chloro-7-methyl-3H-imidazo[4,5-b]pyridin-2-yl)-2-{[(2R)-pyrrolidin-2-ylmethyl]amino}phenol tert-Butyl (2R)-2-([{4-(6-chloro-7-methyl-3H-imidazo[4,5-b]pyridin-2-yl)-2-hydroxyphenyl]amino}methyl)pyrrolidine-1-carboxylate (Example 250a) (0.017 g, 0.037 mmol) was dissolved in dichloromethane (3 ml) and trifluoroacetic acid (1 ml). After 3 h, the reaction mixture was evaporated and the residue was purified by HPLC-$C_{18}$, giving the title product as a bis(trifluoroacetate) (0.012 g, 55%).

APCI-MS m/z: 358.2, 360.1 [MH+].

$^1$H-NMR (400 MHz, DMSO-$d_6$): δ 9.95 (s, 1H), 8.96 (s, 1H), 8.46 (s, 1H), 8.23 (s, 1H), 7.66-7.60 (m, 2H), 6.77 (d, J 8.3 Hz, 1H), 3.84-3.73 (m, 1H), 3.52-3.38 (m, 2H), 3.29-3.13 (m, 2H), 2.61 (s, 3H), 2.17-2.05 (m, 1H), 2.02-1.82 (m, 2H), 1.74-1.62 (m, 1H).

a) tert-Butyl (2R)-2-({[4-(6-chloro-7-methyl-3H-imidazo[4,5-b]pyridin-2-yl)-2-hydroxyphenyl]amino}methyl)pyrrolidine-1-carboxylate 2-Amino-5-(6-chloro-7-methyl-3H-imidazo[4,5-b]pyridin-2-yl)phenol (Example 249) (0.050 g, 0.18 mmol) and tert-butyl (2R)-2-formylpyrrolidine-1-carboxylate (0.036 g, 0.18 mmol) were dissolved in NMP (1.0 ml) and acetic acid (0.10 ml). TMSCl (0.046 ml, 0.36 mmol) and NaBH(OAc)$_3$ (0.072 g, 0.36 mmol) were added and the mixture stirred overnight. The crude mixture was purified by HPLC-C$_{18}$ giving the title compound (0.017 g, 21%).

APCI-MS m/z: 458.4, 460.3 [MH$^+$].

EXAMPLE 251

[5-(6-Chloro-7-methyl-3H-imidazo[4,5-b]pyridin-2-yl)-2-(2-morpholin-4-ylethoxy)phenyl][(2R)-pyrrolidin-2-ylmethyl]amine 6-Chloro-7-methyl-2-[4-(2-morpholin-4-ylethoxy)-3-nitrophenyl]-3H-imidazo[4,5-b]pyridine (100 mg) was dissolved in methanol (100 ml) and hydrogenated (50 psi, 3 h) with Raney nickel as catalyst. The catalyst was removed by filtration and the solvent removed in vacuo. The residue was dissolved in acetonitrile (50 ml) and Boc-Pro-CHO (100 µl), HOAc (0.5 ml) and NaHB(OAc)$_3$ (200 mg) were added. This mixture was heated at 60° C. for 3 h and then allowed to cool. It was filtered and the solvent evaporated in vacuo. The residue was dissolved in dichloromethane (40 ml) and TFA (1 ml) was added and the mixture heated to reflux and then left standing at room temperature for 14 h, whereupon it was filtered and evaporated in vacuo. The residue was applied to semi-preparative HPLC-C$_8$ to afford the pure title compound 1.0 mg (1%).

APCI-MS m/z: 471.3, 473.2 [MH$^+$].

$^1$H-NMR (300 MHz, DMSO-d$_6$): δ 8.23 (s, 1H), 7.50 (d, J 8.6 Hz, 1H), 7.42 (s, 1H), 7.00 (d, J 8.6 Hz, 1H), 4.18 (t, J 5.5 Hz, 2H), 3.58 (t, J 4.7 Hz, 4H), 2.89-2.82 (m, 2H), 2.79-2.70 (m, 3H), 2.62, (s, 3H), 2.55-2.38 (m, 8H), 2.27-2.25 (m, 2H).

a) 6-Chloro-7-methyl-2-[4-(2-morpholin-4-ylethoxy)-3-nitrophenyl]-3H-imidazo[4,5-b]pyridine 4-(6-Chloro-7-methyl-3H-imidazo[4,5-b]pyridin-2-yl)-2-nitrophenol (Example 248) (105 mg, 0.34 mmol), 4-(2-chloroethyl)morpholine hydrochloride (74 mg, 0.40 mmol) and sodium hydride (29 mg, 1.2 mmol) were dissolved in DMF (13 ml). The reaction mixture was stirred at 100° C. overnight and then quenched with water (5 ml) and evaporated. The residue was dissolved in CH$_3$CN (4 ml) and a drop of TFA and purified by HPLC C$_{18}$. The appropriate fractions were collected and concentrated in vacuo to afford the subtitle compound (100 mg, 60%).

APCI-MS m/z: 471.3, 473.3 [MH$^+$].

EXAMPLE 252

4-(6-Chloro-7-methyl-3H-imidazo[4,5-b]pyridin-2-yl)-N$^1$-(2-morpholin-4-ylethyl)benzene-1,2-diamine 5-Chloro-4-methylpyridine-2,3-diamine (Example 249b) (1.47 g, 9 mmol) and 4-fluoro-3-nitrobenzoic acid (1.73 g, 9 mmol) were mixed in phosphorous oxychloride (50 ml) and heated to 110° C. for 64 h. When cool, the excess phosphorous oxychloride was removed in vacuo to afford a brown semi-solid (about 4 g) consisting of 6-chloro-2-(4-fluoro-3-nitrophenyl)-7-methyl-3H-imidazo[4,5-b]pyridine and various inorganic material. To 1.0 g of this crude material, (2-morpholin-4-ylethyl)amine (2 ml) was added and the mixture heated in the microwave oven (180° C., 20 min).

The reaction mixture was diluted with DMF and subjected to semi-preparative HPLC-C$_{18}$ affording the product as a TFA salt. The salt was dissolved in EtOAc (10 ml) and washed with aqueous 10% NaHCO$_3$ solution (5 ml), brine (5 ml) and dried (MgSO$_4$). Evaporation of the solvent yielded the product (using these conditions the nitro group was reduced and no trace of the nitro compound could be isolated) as an off-white powder (34 mg, 39%).

APCI-MS m/z: 387.3, 389.3 [MH$^+$].

$^1$H-NMR (300 MHz, DMSO-d$_6$): δ 13.10 (s, 1H), 8.14 (s, 1H), 7.50 (s, 1H), 7.42 (d, J 8.4 Hz, 1H), 6.54 (d, J 8.2 Hz, 1H), 5.00 (s, 1H), 4.76 (s, 2H), 3.60 (t, J 4.6 Hz, 4H), 3.28-3.22 (m, 2H), 2.62-2.53 (m, 5H), 2.45 (t, J 4.4 Hz, 4H).

EXAMPLE 253

[5-(6-Chloro-7-methyl-3H-imidazo[4,5-b]pyridin-2-yl)-2-(4-methylpiperazin-1-yl)phenyl]amine Crude 6-chloro-2-(4-fluoro-3-nitrophenyl)-7-methyl-3H-imidazo[4,5-b]pyridine (Example 252) (333 mg) and 1-methylpiperazine (1.0 ml) were mixed and left at room temperature for 15 min, whereupon it was diluted with EtOAc (50 ml) and washed with water (100 ml). The aqueous phase was extracted with EtOAc (50 ml) and the combined organic phase was evaporated in vacuo. The yellow oily residue was dissolved in methanol (100 ml) and hydrogenated in a Parr apparatus (Raney nickel, 60 psi, 5 h). The catalyst was removed by filtration and the solvent removed in vacuo. The residue was purified by semi-preparative HPLC-C$_{18}$ affording the product as a trifluoroacetate. The salt was dissolved in EtOAc (10 ml) and washed with aqueous 10% NaHCO$_3$ solution (5 ml), brine (5 ml) and dried (MgSO$_4$). Evaporation of the solvent yielded the product as an off-white powder (67 mg, 25%).

APCI-MS m/z: 357.3, 359.2 [MH$^+$].

$^1$H-NMR (300 MHz, DMSO-d$_6$): δ 13.39 (bs, 1H), 12.80 (bs, 1H), 8.21 (s, 1H), 7.60 (s, 1H). 7.40 (d, J 8.3 Hz, 1H), 7.00 (d, J 8.3 Hz, 1H), 4.93 (s, 2H), 2.89 (m, 4H), 2.60 (s, 3H), 2.58 (m, 4H), 2.29 (s, 3H).

EXAMPLE 254

6,7-Dichloro-2-[4-(4-morpholinyl)phenyl]-1H-imidazo[4,5-b]pyridine 2,3-Diamino-4,5-dichloropyridine (Example 206a) (0.10 g, 0.56 mmol) and 4-morpholin-4-ylbenzoic acid (0.12 g, 0.56 mmol) were dissolved in POCl$_3$ (5 ml) and heated to 105° C. for 5 h. The excess of POCl$_3$ was evaporated off and the residue was dissolved in EtOAc and aqueous K$_2$CO$_3$. The aqueous phase was extracted three times with EtOAc. The combined organic phases were washed with brine, dried (Na$_2$SO$_4$), evaporated in vacuo and the residue was purified by HPLC-C$_{18}$. The product crystallized from the chromatography fraction and was filtered off and dried to yield a white powder (0.040 g, 20%).

APCI-MS m/z 349.2, 351.1 [MH$^+$].

$^1$H-NMR (400 MHz, DMSO-d$_6$): δ 13.68 (s, 1H), 8.37 (s, 1H), 8.11 (d, J 8.8 Hz, 2H), 7.09 (d, J 9.0 Hz, 2H), 3.75 (t, J 4.8 Hz, 4H), 3.27 (t, J 4.8 Hz, 4H).

EXAMPLE 255

[5-(6,7-Dichloro-3H-imidazo[4,5-b]pyridin-2-yl)-2-morpholin-4-ylphenyl]amine 2,3-Diamino-4,5-dichloropyridine (Example 206a) (177 mg, 1.0 mmol) and 4-morpholin-4-yl-3-nitrobenzaldehyde (236 mg, 1 mmol) were dissolved in DMF (50 ml). p-Toluenesulfonic acid monohydrate (38 mg, 0.20 mmol) was added and the mixture heated to 100° C. overnight. The solvent was removed in vacuo and the residue purified by column chromatography on silica gel (dichloromethane/methanol 1:0 to 3:7) to afford the nitro intermediate as a yellow solid (118 mg). This intermediate was suspended in methanol (100 ml) and Raney nickel (approx. 0.2 g) was added and the mixture hydrogenated in a Parr apparatus (3 atm., 6 h). The catalyst was removed by filtration and the pale yellow reaction mixture evaporated in vacuo. The residue was purified by semi-preparative HPLC-$C_{18}$ affording the product as a trifluoroacetate. The salt was dissolved in EtOAc (10 ml) and washed with aqueous 10% $NaHCO_3$ solution (5 ml), brine (5 ml) and dried ($MgSO_4$). Evaporation of the solvent yielded the product as a yellow powder (17 mg, 5%).

APCI-MS m/z: 364.2, 366.1 [$MH^+$].

$^1$H-NMR (400 MHz, DMSO-$d_6$): δ 13.75 (s, 1H), 8.40 (s, 1H), 7.65 (s, 1H), 7.45 (d, J 58.0 Hz, 1H), 7.02 (d, J 8.2 Hz, 1H), 5.06 (s, 2H), 3.77 (t, J 4.4 Hz, 4H), 2.88 (t, J 4.4 Hz, 4H).

EXAMPLE 256

2-(4-Aminophenyl)-6-chloro-N-phenyl-3H-imidazo[4,5-b]pyridin-7-amine

6-Chloro-2-(4-nitrophenyl)-N-phenyl-3H-imidazo[4,5-b]pyridin-7-amine (0.35 g, 1.0 mmol) was dissolved in 50 ml methanol. A catalytic amount of Raney-Nickel was added. The solution was shaken for 45 min under hydrogen pressure (3 atm). The catalyst was filtered off and the solvent removed in vacuo. The crude product was purified by column chromatography on silica, eluting with EtOAc/MeOH 9:1, giving the title product (0.29 g, 85%).

APCI-MS m/z: 336.0, 338.0 [$MH^+$].

$^1$H-NMR (400 MHz, DMSO-$d_6$): δ 8.36 (s, 1H), 8.06 (s, 1H), 7.76 (d, J 8.5 Hz, 2H), 7.21 (t, J 7.8 Hz, 2H), 7.02 (d, J 7.9 Hz, 2H), 6.90 (t, J 7.3 Hz, 1H), 6.59 (d, J 8.6 Hz, 2H), 5.57 (s, 2H).

a) 6-Chloro-2-(4-nitrophenyl)-N-phenyl-3H-imidazo[4,5-b]pyridin-7-amine 6,7-Dichloro-2-(4-nitrophenyl)-3H-imidazo[4,5-b]pyridine (0.73 g, 2.4 mmol), aniline (0.70 ml) and a catalytical amount of p-toluenesulfonic acid monohydrate were dissolved in o-dichlorobenzene (4.0 ml) and heated to 180° C. for 5 h. Ethyl acetate and methanol were added, the mixture stirred and the solid filtered off to afford the title compound (0.68 g, 77%).

APCI-MS m/z: 366.0, 368.0 [$MH^+$].

b) 6,7-Dichloro-2-(4-nitrophenyl)-3H-imidazo[4,5-b]pyridine 2,3-Diamino-4,5-dichloropyridine (Example 206a) (2.5 g, 14 mmol) and 4-nitrobenzoic acid (2.3 g, 14 mmol) were dissolved in $POCl_3$ (40 ml) and heated to 105° C. for 5 h. The excess of $POCl_3$ was evaporated off and the residue was dissolved in EtOAc and aqueous $K_2CO_3$. The aqueous phase was basified with 10M KOH and extracted three times with EtOAc. The combined organic phase was washed with brine, dried ($Na_2SO_4$) and evaporated in vacuo to afford the title compound (2.5 g, 58%).

APCI-MS m/z: 308.9, 310.9 [$MH^+$].

EXAMPLE 257

N-[4-(6,7-Dichloro-3H-imidazo[4,5-b]pyridin-2-yl)phenyl]-N-(2-morpholin-4-ylethyl)amine 2,3-Diamino-4,5-dichloropyridine (Example 206a) (0.10 g, 0.56 mmol) and 4-[(2-morpholin-4-ylethyl)amino]benzoic acid (prepared in a manner analogous to Example 206c) (0.14 g, 0.56 mmol) were dissolved in $POCl_3$ (5 ml) and heated to 105° C. for 5 h. The excess of $POCl_3$ was evaporated off and the residue was dissolved in EtOAc and aqueous $K_2CO_3$. The aqueous phase was extracted three times with EtOAc. The combined organic phases were washed with brine, dried ($Na_2SO_4$), evaporated in vacuo and the residue was purified by HPLC-$C_{18}$, giving the title product (0.006 g, 2%).

APCI-MS m/z 392.2/394.2 [$MH^+$].

$^1$H-NMR (400 MHz, DMSO-$d_6$): δ 13.53 (s, 1H), 8.31 (s, 1H), 7.97 (d, J 8.7 Hz, 2H), 6.71 (d, J 8.8 Hz, 2H), 6.25 (t, J 5.1 Hz, 1H), 3.59 (t, J 4.2 Hz, 4H), 3.23 (q, J 6.3 Hz, 2H), 2.56-2.50 (m, 2H), 2.46-2.38 (m, 4H).

EXAMPLE 258

6-Bromo-7-methyl-2-[4-(2-piperidin-1-ylethoxy)phenyl]-3H-imidazo[4,5-b]pyridine

5-Bromo-4-methylpyridin-2,3-diamine[2] (0.50 g, 2.5 mmol) was dissolved in DMF (7.0 ml). Iron(III)chloride hexahydrate (0.033 g, 0.12 mmol) was added and the mixture heated to 80° C. 4-(2-Piperidin-1-ylethoxy)benzaldehyde (0.58 g, 2.5 mmol) dissolved in DMF (3.0 ml) was added dropwise and the reaction mixture was heated at 120° C. for 5 h with air bubbling through the solution. The solvent was removed by evaporation and the solid residue was washed with 1M NaOH and diethyl ether. The crude product was purified by column chromatography (EtOAc/heptane, 1:1), giving the title product (0.20 g, 19%).

APCI-MS m/z: 415, 417 [$MH^+$].

[2]U.S. Pat. No. 5,290,943

$^1$H-NMR (DMSO-$d_6$): δ 13.3 (1H, bs), 8.34 (1H, s), 8.17 (2H, d), 7.13 (2H, d), 4.16 (2H, t), 3.31 (3H, s), 2.68 (2H, t), 2.46-2.42 (4H, m), 1.53-1.49 (4H, m), 1.41-1.38 (2H, m).

EXAMPLE 259

6-Bromo-7-methyl-2-(4-nitrophenyl)-1H-imidazo[4,5-b]pyridine

5-Bromo-4-methylpyridine-2,3-diamine[2] (6.2 g, 31 mmol) and 4-nitrobenzoyl chloride (5.8 g, 31 mmol) were dissolved in THF (150 ml). Hünig's base (5 ml, 31 mmol) was added dropwise over 25 min. and the reaction mixture was stirred at room temperature overnight. The reaction mixture was filtered through a short plug of silica and washed with EtOAc, followed by evaporation. This intermediate was dissolved in methanesulfonic acid (170 ml) and was heated to 100° C. After cooling to room temperature, water was added to the reaction mixture under stirring. The brown precipitate was filtered off, re-dissolved in KOH-solution and extracted with EtOAc. After drying ($Na_2SO_4$), filtration and evaporation of the organic phase, the title compound was isolated (8.77 g, 81%).

APCI-MS m/z: 332.9, 335.0 [MH+].
$^1$H-NMR (400 MHz, DMSO-d$_6$): δ 14.08 (bs, 0.34H), 13.47 (bs, 0.66H), 8.45 (m, 5H), 2.68 (s, 3H).
$^2$U.S. Pat. No. 5,290,943

EXAMPLE 260

4-(6-Bromo-7-methyl-1H-imidazo[4,5-b]pyridin-2-yl)aniline

6-Bromo-7-methyl-2-(4-nitrophenyl)-1H-imidazo[4,5-b]pyridine (Example 259) (0.11 g, 0.34 mmol) was dissolved in methanol (15 ml) and iron powder (0.097 g, 1.70 mmol) was added. Conc. HCl (1.8 ml) was added dropwise over 15 min. and the reaction mixture was stirred at room temperature for 2 h. Methanol was partly removed by evaporation, after which water and ammonia were added. The aqueous phase was extracted with CHCl$_3$, dried (Na$_2$SO$_4$), filtered and evaporated to yield the product (81.2 mg, 78%).

APCI-MS m/z: 303.0, 305.0 [MH+].
$^1$H-NMR (400 MHz, DMSO-d$_6$): δ 13.28 (bs, 0.69H), 12.66 (bs, 0.31H), 8.28 (s, 1H), 7.91 (d, 2H), 6.67 (d, 2H), 5.77 (s, 2H), 2.61 (s, 3H).

EXAMPLE 261

N-[4-(6-Bromo-7-methyl-1H-imidazo[4,5-b]pyridin-2-yl)phenyl]-3-cyanobenzenesulfonamide 4-(6-Bromo-7-methyl-1H-imidazo[4,5-b]pyridin-2-yl)aniline (Example 260) (0.020 g, 0.07 mmol) was dissolved in pyridine and 3-cyanobenzenesulfonyl chloride (0.013 g, 0.07 mmol) was added. The mixture was heated to 60° C. for 3 h. Thereafter the solvent was removed in vacuo and the residue was submitted to HPLC-C$_{18}$ purification. Yield: 0.006 g (15%) of the title compound as the trifluoroacetate.

APCI-MS m/z: 467.9, 469.9 [MH+].
$^1$H-NMR (400 MHz, DMSO-d$_6$): δ 13.56 (s, 1H), 10.88 (s, 1H), 8.36 (m, 2H), 8.11 (t, J 8.0 Hz, 4H), 7.78 (m, 1H), 7.29 (d, J 8.4 Hz, 2H), 2.62 (s, 3H).

EXAMPLE 262

N-[4-(6-Bromo-7-methyl-1H-imidazo[4,5-b]pyridin-2-yl)phenyl]-4-cyanobenzenesulfonamide By a procedure similar to Example 261 but using 4-cyanobenzenesulfonyl chloride the title compound was obtained as the bis(trifluoroacetate).

APCI-MS m/z: 468.1, 470.1 [MH+].
$^1$H-NMR (400 MHz, DMSO-d$_6$) δ 10.96 (s, 1H), 8.38 (s, 1H), 8.09 (m, 4H), 7.98 (dd, J 6.7, 2.0 Hz; 2H), 7.29 (d, J 8.8 Hz, 2H), 2.62 (s, 3H).

EXAMPLE 263

N-[4-(6-Bromo-7-methyl-1H-imidazo[4,5-b]pyridin-2-yl)phenyl]quinoline-8-sulfonamide By a procedure similar to Example 261 but using quinoline-8-sulfonyl chloride the title compound was obtained as the bis(trifluoroacetate).

APCI-MS m/z: 494.1, 496.2 [MH+].
$^1$H-NMR (DMSO-d$_6$): δ (1H, d), 8.67 (1H, d), 8.26 (1H, dd), 8.12 (1H, d), 8.04 (1H, dd), 7.44 (1H, dt), 7.10 (1H, d), 7.03 (1H, t), 5.08 (1H, t).

EXAMPLE 264

N-[4-(6-Bromo-7-methyl-1H-imidazo[4,5-b]pyridin-2-yl)phenyl]-4-methoxybenzenesulfonamide By a procedure similar to Example 261 but 4-methoxybenzenesulfonyl chloride the title compound was obtained as the trifluoroacetate.

APCI-MS m/z: 473.1, 475.2 [MH+].
$^1$H-NMR (400 MHz, DMSO-d$_8$): δ 10.58 (s, 1H), 8.36 (s, 1H), 8.07 (d, J 8.8 Hz, 2H), 7.77 (dd, J 6.9, 2.1 Hz, 2H), 7.27 (d, J 8.8 Hz, 2H), 7.08 (dd, J 7.0, 2.1 Hz, 2H), 3.78 (s, 3H), 2.62 (s, 3H).

EXAMPLE 265

N-[4-(6-Bromo-7-methyl-1H-imidazo[4,5-b]pyridin-2-yl)phenyl]-4-(2-cyanoethoxy)benzenesulfonamide By a procedure similar to Example 261 but using 4-(2-cyanoethoxy)benzenesulfonyl chloride the title compound was obtained as the trifluoroacetate.

APCI-MS m/z: 512.0, 514.0, 513.0 [MH+].
$^1$H-NMR (400 MHz, DMSO-d$_6$): δ 10.60 (s, 1H), 8.36 (s, 1H), 8.08 (d, J 8.7 Hz, 2H), 7.78 (dd, J 7.0, 1.9 Hz, 2H), 7.27 (d, J 8.8 Hz, 2H), 7.12 (dd, J 7.0, 2.0 Hz, 2H), 4.23 (t, J 6.0 Hz, 2H), 3.00 (t, J 5.9 Hz, 2H), 2.62 (s, 3H).

EXAMPLE 266

N-[4-(6-Bromo-7-methyl-1H-imidazo[4,5-b]pyridin-2-yl)phenyl]-1-methyl-1H-imidazole-4-sulfonamide By a procedure similar to Example 261 but using 1-methyl-1H-imidazole-4-sulfonyl chloride the title compound was obtained as the trifluoroacetate.

APCI-MS m/z: 447.0, 449.0, 448.0 [MH+].
$^1$H-NMR (400 MHz, DMSO-d$_6$): δ 10.96 (s, 1H), 8.38 (s, 1H), 8.09 (m, 4H), 7.98 (dd, J 6.7, 2.0 Hz, 2H), 7.29 (d, J 8.8 Hz, 2H), 2.62 (s, 3H).

EXAMPLE 267

N-[4-(6,7-Dichloro-1H-imidazo[4,5-b]pyridin-2-yl)phenyl]-4-methoxybenzenesulfonamide By a procedure similar to Example 261 but using 4-(6,7-dichloro-1H-imidazo[4,5-b]pyridin-2-yl)aniline and 4-methoxybenzenesulfonyl chloride the title compound was obtained as the trifluoroacetate.

APCI-MS m/z: 449.0, 451.0 [MH+].
$^1$H-NMR (400 MHz, DMSO-d$_6$): δ 10.63 (s, 1H), 8.44 (s, 1H), 8.10 (d, J 8.8 Hz, 2H), 7.77 (m, 2H), 7.28 (d, J 8.8 Hz, 2H), 7.08 (dd, J 7.1, 1.9 Hz, 2H), 3.79 (s, 3H).

a) 4-(6,7-Dichloro-1H-imidazo[4,5-b]pyridin-2-yl)aniline

By at procedure similar to Examples 258 and 259 but starting from 2,3-diamino-4,5-dichloropyridine (Example 206a) and 4-nitrobenzoyl chloride, the title compound was obtained.

APCI-MS m/z: 279.0 [MH+].

EXAMPLE 268

6-Chloro-2-4-[(2-morpholin-4-ylethyl)amino]phenyl}-N-phenyl-3H-imidazo[4,5-b]pyridin-7-amine 2-(4-Aminophenyl)-6-chloro-N-phenyl-3H-imidazo[4,5-b]pyridin-7-amine (Example 256) (23.7 mg, 0.07 mmol) and NaCNBH$_3$ (8.8 mg, 0.14 mmol) were dissolved in NMP/MeCN (1:5, 2 ml). Chloroacetaldehyde (0.0046 ml, 0.07 mmol), MgSO$_4$ (50 mg) and more NMP/MeCN (1:1 mixture, 1 ml) were added to the reaction mixture. The pH was adjusted to 4 using a few drops of conc. H$_2$SO$_4$ and the reaction mixture was stirred at room temperature for 1 h. The reaction mixture was filtered through a short plug of silica gel eluting with MeCN. Evaporation of the solvent gave an intermediate that was dissolved in morpholine (3 ml) and was heated to 130° C. for 15 min in a microwave oven. The reaction mixture was evaporated to dryness and the residue purified by HPLC-C$_8$ to afford the product, after freeze drying, as a white powder. Yield: 2 mg (6%, two steps).

APCI-MS m/z: 449.1 [MH$^+$].

$^1$H-NMR (400 MHz, CD$_3$OD): δ 8.20 (s, 1H), 7.76 (d, J 8.8 Hz, 2H), 7.31 (t, J 7.8 Hz, 2H), 7.13-7.02 (m, 3H), 6.69 (d, J 8.8 Hz, 2H), 3.72 (t, J 4.6 Hz, 4H), 3.31 (m, 2H), 2.63 (t, J 6.6 Hz, 2H), 2.57-2.50 (m, 4H).

EXAMPLE 269

6-Chloro-7-methoxy-2-[4-(2-morpholin-4-ylethoxy)phenyl]-3H-imidazo[4,5-b]pyridine 6-Chloro-2-[4-(2-chloroethoxy)phenyl]-7-methoxy-3H-imidazo[4,5-b]pyridine (0.27 g, 0.8 mmol), morpholine (0.22 ml, 2.52 mmol) and Hünig's base (1.42 ml, 8.15 mmol) were dissolved in NMP (20 ml) and the mixture was heated at 100° C. for 9 h. The NMP was partly removed by evaporation, after which water was added. The precipitated crude material was purified by column chromatography (dichloromethane/methanol 95:5), giving the title product (0.022 g, 7%).

APCI-MS m/z: 389 [MH$^+$].

$^1$H-NMR (DMSO-d$_6$): δ 13.5 (1H, bs), 8.16 (1H, s), 8.14 (2H, d), 7.12 (2H, d), 4.64 (3H, s), 4.18 (2H, t), 3.59 (4H, t), 2.72 (2H, t), 2.51-2.47 (4H, m).

a) 6-Chloro-2-[4-(2-chloroethoxy)phenyl]-7-methoxy-3H-imidazo[4,5-b]pyridine 2-[4-(6-Chloro-7-methoxy-3H-imidazo[4,5-b]pyridin-2-yl)phenoxy]ethanol (0.26 g, 0.8 mmol) was dissolved in SOCl$_2$ (10 ml). The reaction mixture was refluxed for 3 h, after which the excess SOCl$_2$ was removed by evaporation. Repetitive co-evaporation with toluene yielded pure title compound (0.275 g, 100%).

APCI-MS m/z: 338,340 [MH$^+$].

$^1$H-NMR (DMSO-d$_6$): δ 8.18 (1H, s), 8.16 (2H, d), 7.16 (2H, d), 4.64 (3H, s), 4.36 (2H, t), 3.99 (2H, t).

b) 2-[4-(6-Chloro-7-methoxy-3H-imidazo[4,5-b]pyridin-2-yl)phenoxy]ethanol

5-Chloro-4-methoxypyridin-2,3-diamine (0.498 g, 2.9 mmol) was dissolved in DMF (7 ml). Iron(III)chloride hexahydrate (0.06 g, 0.2 mmol) was added and the mixture heated to is 80° C. 4-(2-Hydroxyethoxy)benzaldehyde (0.48 g, 2.9 mmol) dissolved in DMF (4 ml) was added dropwise, and the reaction mixture was heated at 110° C. for 11 h with air bubbling through the solution. The solvent was removed by evaporation, the solid residue was dissolved in warm methanol and filtered through a short plug of silica gel. Following evaporation and recrystallization (methanol), the title compound was isolated (0.26 g, 28%).

APCI-MS m/z: 320.1 [MH$^+$].

$^1$H-NMR (DMSO-d$_6$): δ 13.5 (1H, bs), 8.16 (1H, s), 8.14 (2H, d), 7.11 (2H, d), 4.91 (1H, t), 4.64 (3H, s), 4.08 (2H, t), 3.75 (2H, q).

c) 5-Chloro-4-methoxypyridine-2,3-diamine

By a procedure similar to Example 206(a, b) but starting from 5-chloro-4-methoxypyridin-2-amine, the title compound was obtained.

APCI-MS m/z: 174.1 [MH$^+$].

$^1$H-NMR (DMSO-d$_6$): δ 7.26 (1H, s), 5.62 (2H, bs), 4.72 (2H, bs), 3.71 (3H, s).

EXAMPLE 270

6-Chloro-2-{4-[di(3-cyanobenzyl)amino]phenyl}-7-methoxy-1-yl-3H-imidazo[4,5-b]pyridine 4-(6-Chloro-7-methoxy-3H-imidazo[4,5-b]pyridin-2-yl)aniline (0.486 g, 1.77 mmol) was dissolved in NMP (5 ml). 3-Cyanobenzaldehyde (0.235 g, 1.79 mmol), acetic acid (0.5 ml), TMSCl (0.45 ml, 3.6 mmol) and NaBH(OAc)$_3$ (0.752 g, 3.55 mmol) were added and the reaction mixture was stirred at room temperature for 3 h. Following addition of 1M NaOH (5 ml), the crude product was filtered off and purified by recrystallisation (methanol) followed by filtration through a short plug of silica, giving the title product (0.060 g, 7%).

APCI-MS m/z: 505 [MH$^+$].

$^1$H-NMR ((DMSO-4): δ 13.3 (1H, bs), 8.10 (1H, s), 7.96 (2H, d), 7.75-7.55 (8H, m), 6.82 (2H, d), 4.91 (4H, s), 4.59 (3H, s).

a) 4-(6-Chloro-7-methoxy-3H-imidazo[4,5-b]pyridin-2-yl)aniline

6-Chloro-7-methoxy-2-(4-nitrophenyl)-3H-imidazo[4,5-b]pyridine (0.56 g, 1.8 mmol) was dissolved in methanol (30 ml). (NH$_4$)$_2$S (20% in water, 5 ml, 15 mmol) was added and the mixture was heated to reflux for 5 h. The methanol was removed under reduced pressure and the resulting precipitate was filtered off and washed with ice-cold water giving 0.486 g (96%) of the subtitle compound.

APCI-MS m/z: 275 [MH$^+$].

$^1$H-NMR (DMSO-d$_6$): δ 13.15 (1H, bs), 8.08 (1H, s), 7.88 (2H, d), 6.67 (2H, d), 5.70 (2H, bs), 4.61 (3H, s).

b) 6-Chloro-7-methoxy-2-(4-nitrophenyl)-3H-imidazo[4,5-b]pyridine

5-Chloro-4-methoxypyridin-2,3-diamine (0.500 g, 2.88 mmol) was dissolved in DMF (7 ml). Iron(III)chloride hexahydrate (0.062 g, 0.23 mmol) was added and the mixture heated to 80° C. 4-Nitrobenzaldehyde (0.434 g, 2.87 mmol) dissolved in DMF (4 ml) was added dropwise, and the reaction mixture was heated at 110° C. for 11 h with air bubbling through the solution. The DMF was removed by evaporation, the solid residue was dissolved in warm methanol and filtered through a short plug of silica gel. Following evaporation and recrystallization (methanol) the subtitle compound was isolated. Yield: 0.569 g (65%).

APCI-MS m/z: 305 [MH$^+$].

¹H-NMR (DMSO-d₆): δ 14.1 (1H, bs), 8.48-8.41 (4H, m), 8.29 (1H, s), 4.68 (3H, s).

EXAMPLE 271

3-([{4-(6-Chloro-7-methoxy-1H-imidazo[4,5-b]pyridin-2-yl)phenyl]amino}methyl)benzonitrile)

4-(6-Chloro-7-methoxy-3H-imidazo[4,5-b]pyridin-2-yl)aniline (Example 270a) (0.050 g, 0.18 mmol) was dissolved in NMP (1 ml). 3-Cyanobenzaldehyde (0.018 g, 0.14 mmol), acetic acid (0.5 ml), TMSCl (0.046 ml, 0.36 mmol) and NaBH(OAc)₃ (0.077 g, 0.36 mmol) were added and the reaction mixture was stirred at room temperature for 1 h. The reaction mixture was diluted with CH₃CN/TFA/water and purified by HPLC-C₁₈, giving the title product as the trifluoroacetate. (0.025 g, 22%).

APCI-MS m/z: 390.1, 392.1 [MH⁺].
¹H-NMR (400 MHz, DMSO-d₆): δ 8.08 (s, 1H), 7.90 (d, J 8.8 Hz, 2H), 7.80 (s, 1H), 7.72-7.69 (m, 2H), 7.55 (t, J 7.7 Hz. 1H), 6.69 (d, J 8.8 Hz, 2H), 4.62 (s, 3H), 4.46 (s, 2H).

EXAMPLE 272

N-[4-(6-Chloro-7-methoxy-1H-imidazo[4,5-b]pyridin-2-yl)phenyl]-4-cyanobenzenesulfonamide By a procedure similar to Example 261 but using 4-(6-chloro-7-methoxy-3H-imidazo[4,5-b]pyridin-2-yl)aniline (Example 270a) and 4-cyanobenzenesulphonyl chloride, the title compound was obtained as the trifluoroacetate.

APCI-MS m/z: 440.0, 442.1 [MH⁺].
¹H-NMR (400 MHz, DMSO-d₆): δ 10.92 (s, 1H), 8.17 (s, 1H), 8.05 (t, J 13.4 Hz, 4H), 7.96 (d, J 14.6 Hz, 2H), 7.25 (d, J 8.8 Hz, 2H), 4.59 (s, 3H).

EXAMPLE 273

6-Chloro-7-methoxy-2-[4-(2-piperidin-1-ylethoxy)phenyl]-3H-imidazo[4,5-b]pyridine By a procedure similar to Example 269 but using 5-chloro-4-methoxypyridin-2,3-diamine and 4-(2-piperidin-1-ylethoxy)benzaldehyde, the title compound was obtained as the bis(trifluoroacetate).

APCI-MS m/z: 387.1 [MH⁺].
¹H-NMR (400 MHz, CD₃OD): δ 8.12 (d, J 10.3 Hz, 2H), 8.11 (s, 1H), 7.12 (d, J 9.0 Hz, 2H), 4.63 (s, 3H), 4.43 (t, J 4.9 Hz, 2H), 3.63 (d, J 11.7 Hz, 2H), 3.57 (t, J 4.8 Hz, 2H), 3.05 (dd, J 12.2, 10.1 Hz, 2H), 1.97 (d, J 13.8 Hz, 2H), 1.91-1.73 (m, 0.3H), 1.53 (mult, 1H).

EXAMPLE 274

5-(6-Bromo-3H-imidazo[4,5-b]pyridin-2-yl)-N,N-diethyl-1,3-thiazol-2-amine

5-Bromopyridine-2,3-diamine (0.1 g, 0.53 mmol) was dissolved in NMP (0.5 ml) and heated to 170° C. 2-(Diethylamino)-1,3-thiazole-5-carbaldehyde (0.098 g, 0.53 mmol) dissolved in nitrobenzene (1.0 ml) was added slowly (20 min). After 2 h, the reaction mixture was diluted with CH₃CN/water and purified by HPLC-C₁₈, giving the title product (0.01 g, 6%).

APCI-MS m/z: 352.0/354.1 [MH⁺].
¹H-NMR (400 MHz, DMSO-d₆): δ 8.31 (s, 1H), 8.08 (s, 1H), 8.00 (s, 1H), 3.52 (q, J 7.1 Hz, 4H), 1.19 (t, J 7.1 Hz, 6H).

EXAMPLE 275

6-Chloro-2-(5-nitro-2-thienyl)-3H-imidazo[4,5-b]pyridine

5-Chloropyridine-2,3-diamine (4.0 g, 28 mmol) was dissolved in NMP (3 ml) and heated to 170° C. 5-Nitrothiophene-2-carbaldehyde (4.4 g, 28 mmol) dissolved in nitrobenzene (3 ml) and NMP (2 ml) was added slowly over 30 min. After 3 h, the reaction mixture was diluted with EtOAc and purified by dry flash chromatography (0%, 10%, 50%, 70% EtOAc in toluene), giving the title product (2 g, 25%).

APCI-MS m/z: 280.9/282.9 [MH⁺].
¹H-NMR (400 MHz, DMSO-d₆): δ 8.42 (d, J 2.2 Hz, 1H), 8.25 (d, J 2.1 Hz, 1H), 8.24 (d, J 4.5 Hz, 1H), 7.93 (d, J 4.4 Hz, 1H).

EXAMPLE 276

[5-(6-Chloro-3H-imidazo[4,5-b]pyridin-2-yl)-2-thienyl]amine

6-Chloro-2-(5-nitro-2-thienyl)-3H-imidazo[4,5-b]pyridine (Example 275) (0.10 g, 0.36 mmol) was dissolved in methanol (10 ml). A catalytic amount of Raney nickel was added. The solution was shaken for 2 h under hydrogen pressure (3 atm.). The catalyst was filtered off and the crude material was purified by column chromatography (EtOAc) to give the title product (0.04 g, 44%).

APCI-MS m/z: 251.0/253.0 [MH⁺].
¹H-NMR (400 MHz, CD₃OD): δ 8.15 (s, 1H), 7.76 (d, J 1.9 Hz, 1H), 7.46 (d, J 4.1 Hz, 1H), 6.10 (d, J 4.0 Hz, 1H).

EXAMPLE 277

{4-[5-(6-Bromo-3H-imidazo[4,5-b]pyridin-2-yl)-2-furyl]phenyl}amine

6-Bromo-2-[5-(4-nitrophenyl)-2-furyl]-3H-imidazo[4,5-b]pyridine (0.060 g, 0.16 mmol) was dissolved in DMSO (3 ml) and a drop of water. Sodium dithionite (140 mg, 0.8 mmol) was added and the slurry was heated to 50° C. for 2 h. The slurry was diluted with EtOAc and first purified by column chromatography and then by HPLC-C₁₈, giving the title product as the bis(trifluoroacetate. (0.01 g, 11%).

APCI-MS m/z: 355.1/357.1 [MH⁺].
¹H-NMR (400 MHz, DMSO-d₆): δ 8.38 (d, J 2.2 Hz, 1H), 8.20 (d, J 2.1 Hz; 1H), 7.69 (d, J 8.5 Hz, 2H), 7.39 (d, J 3.6 Hz. 1H), 6.93 (d, J 3.5 Hz, 1H), 6.79 (d, J 8.5 Hz, 2H).

a) 6-Bromo-2-[5-(4-nitrophenyl)-2-furyl]-3H-imidazo[4,5-b]pyridine

By a procedure similar to Example 274 but starting from 5-bromopyridine-2,3-diamine and 5-(4-nitrophenyl)-2-furaldehyde, the title compound was obtained.

APCI-MS m/z: 385.0/387.1 [MH⁺].
¹H-NMR (400 MHz, DMSO-d₆): δ 8.43 (s, 1H), 8.35 (d, J 9.0 Hz, 2H), 8.29 (s, 1H), 8.19 (d, J 9.0 Hz, 2H), 7.57 (d, J 3.7 Hz, 1H), 7.50 (d, J 3.7 Hz, 1H).

EXAMPLE 278

6-Chloro-2-[4-(2-piperidin-1-ylethoxy)phenyl]-3H-imidazo[4,5-b]pyridine

5-Chloropyridin-2,3-diamine (0.200 g, 1.39 mmol) was dissolved in DMF (5 ml). Iron(III)chloride hexahydrate (0.025 g, 0.092 mmol) was added and the mixture heated to 80° C. 4-(2-Piperidin-1-ylethoxy)benzaldehyde (0.33 g, 1.41 mmol) dissolved in DMF (2 ml) was added dropwise, and the reaction mixture was heated at 120° C. for 5 h with air bubbling through the solution. The DMF was removed by evaporation and the solid residue was washed with 1M NaOH and diethyl ether. The crude product was purified by column chromatography (EtOAc/heptane, 1:1), giving the title product (0.017 g, 3%).

APCI-MS m/z: 357 [MH$^+$].

$^1$H-NMR (400 MHz, DMSO-d$_6$): δ 13.4 (1H, br. s); 8.28 (1H, s); 8.16 (2H, d); 8.06 (1H, br.s); 7.13 (2H, d); 4.16 (2H, t), 2.68 (2H, t); 2.45-2.43 (4H, m); 1.53-1.48 (4H, m); 1.41-1.37 (2H, m).

SCREEN

Itk LANCE TRF Assay

The Itk kinase assay utilized recombinant human Itk kinase domain fused with GST (Glutathione S-Transferase). The protein was expressed in High five insect cells, purified in one step on an affinity chromatography glutathione column and stored in 50 mM Tris/HCl (pH 7.6), 150 mM NaCl, 5% (w/v) mannitol, 1 mM DTT, 30% glycerol at −70° C. The kinase substrate used in the assay was a biotinylated peptide derived from the Src-optimal substrate (Nair et al, J. Med. Chem., 38: 4276, 1995; biotin-AEEEIYGEFEAKKKK).

The assay additions were as follows: Test compounds (or controls; 1 μL in 100% DMSO) were added to black 96-well flat-bottomed plates (Greiner 655076) followed by 20 μL Itk in assay buffer and the reaction was started by adding 20 μL ATP and peptide substrate in assay buffer. The assay buffer constitution during, phosphorylation was: 50 mM HEPES (pH 6.8), 10 mM MgCl$_2$, 0.015% Brij 35, 1 mM DTT, 10% glycerol, 160 ng/well Itk, 2 μM peptide substrate and 50 μM ATP. The assay was stopped after 50 minutes (RT) by adding 150 μL ice-cold Stop solution (50 mM Tris/HCl, pH 7.5, 10 mM EDTA, 0.9% NaCl and 0.1% BSA) together with LANCE reagents (2 nM PT66-Eu$^{3+}$, Wallac AD0069 and 5 μg/mL Streptavidin-APC, Wallac AD0059. Both concentrations were final in stopped assay solution). The plates were measured on a Wallac 1420 Victor 2 instrument with TRF settings after 1 h incubation, and the ratio (665 signal/615 signal)*10000 was used to calculate the inhibition values. IC$_{50}$ values were determined using XLfit.

When tested in the above screens, the compounds of Examples 1 to 278 gave IC$_{50}$ values for inhibition of Itk activity of less than 25 μM, indicating that the compounds of the invention are expected to possess useful therapeutic properties.

Representative results are shown in the following Table:

| Compound | Inhibition of Kinase Itk (IC$_{50}$ μM) |
|---|---|
| Example 124 | 0.43 |
| Example 29 | 0.31 |
| Example 104 | 0.24 |
| Example 162 | 0.53 |
| Example 180 | 0.29 |
| Example 236 | 0.41 |
| Example 238 | 0.35 |
| Example 267 | 0.26 |

The invention claimed is:

1. A compound of formula (Id)

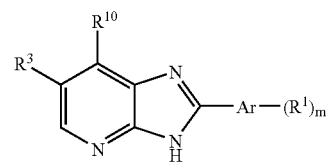

(Id)

wherein:
R$^3$ represents halogen, CN, C1 to 3 alkyl or C1 to 3 alkoxy;
Ar represents phenyl, a 5- or 6-membered heteroaromatic ring or an indole ring; said
heteroaromatic ring incorporating 1 to 3 heteroatoms independently selected from O, N and S;
R$^1$ represents H, halogen, CN, C1 to 6 alkyl, NO$_2$, SO$_2$Me, C1 to 6 alkynyl, CH$_2$OH, OR$^2$, (CH$_2$)$_n$NR$^4$R$^5$ or phenyl optionally substituted by NH$_2$;
m represents an integer 1 or 2; and when m represents 2, each R$^1$ may be selected independently;
n represents an integer 0 or 1;
R$^2$ represents H or C1 to 4 alkyl; said C1 to 4 alkyl being optionally further substituted by a group selected from Ar$^1$, CONH$_2$, CO$_2$Et, OH, NR$^6$R$^7$, halogen and epoxy; and when substituted by NR$^6$R$^7$ or halogen, said alkyl is optionally further substituted by OH;
R$^4$ represents H, C1 to 4 alkyl or CH$_2$Ar$^2$;
R$^5$ represents H, C1 to 6 alkyl, C2 to 6 alkanoyl, SO$_2$—Ar$^5$ or CH$_2$Ar$^2$; said alkyl group
being optionally further substituted by a 5 to 7 membered saturated azacyclic ring optionally incorporating one additional heteroatom selected from O, S and NR$^8$;
or the group —NR$^4$R$^5$ together represents a 5 to 7 membered saturated azacyclic ring optionally incorporating one additional heteroatom selected from O, S and NR$^8$;
R$^6$ represents H, C1 to 4 alkyl or CH$_2$CH$_2$OCH$_3$;
R$^7$ represents H, C1 to 6 alkyl, C3 to 6 cycloalkyl, Ar$^3$, a 5 or 6 membered saturated or partially unsaturated heterocyclic ring incorporating 1 or 2 heteroatoms selected independently from O, N and S and optionally substituted by Me, Et or CO$_2$Et; said C1 to 6 alkyl being optionally substituted by one or more groups selected independently from OH, CN, CONMe$_2$, CONHMe, C1 to 4 alkoxy, halogen, NMe$_2$, Ar$^4$, and a 5 or 6 membered saturated heterocyclic ring incorporating 1 or 2 heteroatoms selected independently from O, N and S and optionally also incorporating a carbonyl group; said C3 to 6 cycloalkyl being optionally substituted by OH or CN;
or the group —NR$^6$R$^7$ together represents a 5 to 7 membered saturated azacyclic ring optionally incorporating 1 additional heteroatom selected from O and NR$^9$; and
optionally substituted by one or more substituents selected independently from OH, NMe$_2$, CONH$_2$, CH$_2$OH, CH$_2$CH$_2$OH, phenyl, pyridyl, piperidinyl or methoxyphenyl;
R$^8$ represents H, C1 to 6 alkyl or CH$_2$Ph;
R$^9$ represents CH$_2$CH$_2$OH, COCH$_3$, Me, CO$_2$Et, CH$_2$CH$_2$OMe or a six membered aromatic or azaaromatic ring optionally further substituted by one or more substituents selected independently from Cl, CN, OMe and CF$_3$;

R¹⁰ represents halogen, CN, C1 to 4 alkyl, C1 to 4 alkoxy, NR¹⁴R¹⁵ or a group —X—Y—Z;
R¹⁴ and R¹⁵ independently represent H or C1 to 4 alkyl; said alkyl being optionally further substituted by OH;
X represents O, S, a bond or NR¹⁶ wherein R¹⁶ represents H or C1 to 4 alkyl; said alkyl being optionally further substituted by OH;
Y represents C1 to 4 alkyl or a bond;
Z represents:
i) phenyl, naphthyl or a 5- or 6-membered heteroaromatic ring system containing one to three heteroatoms independently selected from O, N and S; or
ii) a five- or six-membered saturated heterocyclic ring containing one or two heteroatoms independently selected from O, N and S; said ring optionally being benzo fused; or
iii) C3 to 6 cycloalkyl;
said ring Z being optionally substituted by one or more substituents independently selected from halogen, OH, C1 to 4 alkyl, C1 to 4 alkoxy, hydroxymethyl, methylsulphonyl and NR¹⁷R¹⁸;
R¹⁷ and R¹⁸ independently represent H, C1 to 4 alkyl, formyl or C2 to alkanoyl; or the group NR¹⁷R¹⁸ together represents a saturated 5 to 7 membered azacyclic ring optionally containing one further heteroatom selected from O, N and S;
Ar¹ represents phenyl, thiazolyl or thiadiazolyl, optionally further substituted by halogen;
Ar² represents phenyl, a 5- or 6-membered heteroaromatic ring or a benzimidazole ring;
said heteroaromatic ring incorporating 1 to 3 heteroatoms independently selected from O, N and S; said phenyl or heteroaromatic or benzimidazole ring being optionally further substituted by one or two groups independently selected from halogen, C1 to 4 alkyl, CN, CH₂OH, C1 to 4 alkoxy, CO₂Me, CH₂OAc and pyridyl;
Ar³ represents thiazolyl, triazolyl or tetrazolyl;
Ar⁴ represents phenyl, a 5- or 6-membered heteroaromatic ring or an indole ring; said heteroaromatic ring incorporating 1 to 3 heteroatoms independently selected from O, N and S; said phenyl, heteroaromatic or indole ring being optionally further substituted by one or two groups independently selected from halogen and OMe;
Ar⁵ represents phenyl, a 5- or 6-membered heteroaromatic ring or a quinoline ring; said heteroaromatic ring incorporating 1 to 3 heteroatoms independently selected from O, N and S; said phenyl or heteroaromatic or quinoline ring being optionally further substituted by halogen, C1 to 4 allyl, CN, C1 to 4 alkoxy, and OCH₂CH₂CN;
with the proviso that when R¹⁰ represents halogen, C1 to 4 alkyl, C1 to 4 alkoxy or NH₂;
and Ar represents phenyl; then said phenyl is not substituted at the 4-position by C1 to 2 alkoxy, OH, halogen or C1 to 4 alkyl.

2. A compound according to claim 1 that is:
6,7-dichloro-2-[4-(2-morpholin-4-ylethoxy)phenyl]-3H-imidazo[4,5-b]pyridine
6-chloro-N-(2-methoxyphenyl)-2-{4-[2-(4-morpholinyl)ethoxy]phenyl}-1H-imidazo[4,5-b]pyridin-7-amine
2-[(6-chloro-2-{4-[2-(4-morpholinyl)ethoxy]phenyl}-1H-imidazo[4,5-b]pyridin-7-yl)amino]phenol
6-chloro-N-[1-(methylsulfonyl)-3-pyrrolidinyl]-2-{4-[2-(4-morpholinyl)ethoxy]phenyl}-1H-imidazo[4,5-b]pyridin-7-amine
6-chloro-N-cyclopentyl-2-{4-[2-(4-morpholinyl)ethoxy]phenyl}-1H-imidazo[4,5-b]pyridin-7-amine
N-benzyl-6-chloro-2-{4-[2-(4-morpholinyl)ethoxy]phenyl}-1H-imidazo[4,5-b]pyridin-7-amine
6-chloro-2-{4-[2-(4-morpholinyl)ethoxy]phenyl}-1H-imidazo[4,5-b]pyridin-7-amine
6-chloro-2-{4-[2-(4-morpholinyl)ethoxy]phenyl}-7-(1H-pyrrol-1-yl)-1H-imidazo[4,5-b]pyridine
1-(6-chloro-2-{4-[2-(4-morpholinyl)ethoxy]phenyl}-1H-imidazo[4,5-b]pyridin-7-yl)-3-pyrrolidinamine
1-(6-chloro-2-{4-[2-(4-morpholinyl)ethoxy]phenyl}-1H-imidazo[4,5-b]pyridin-7-yl)-3-pyrrolidinylformamide
6-chloro-N-(2-ethylphenyl)-2-{4-[2-(4-morpholinyl)ethoxy]phenyl}-1H-imidazo[4,5-b]pyridin-7-amine
6-chloro-7-(2,3-dihydro-1H-indol-1-yl)-2-{4-[2-(4-morpholinyl)ethoxy]phenyl}-1H-imidazo[4,5-b]pyridine
6-chloro-7-(4-morpholinyl)-2-{4-[2-(4-morpholinyl)ethoxy]phenyl}-1H-imidazo[4,5-b]pyridine
6-chloro-2-[4-(2-morpholin-4-ylethoxy)phenyl]-N-pyridin-3-yl-3H-imidazo[4,5-b]pyridin-7-amine
[3-({6-chloro-2-[4-(2-morpholin-4-ylethoxy)phenyl]-3H-imidazo[4,5-b]pyridin-7-yl}amino)phenyl]methanol
6-chloro-N-(2-fluorophenyl)-2-[4-(2-morpholin-4-ylethoxy)phenyl]-3H-imidazo[4,5-b]pyridin-7-amine
6-chloro-2-{4-[2-(4-morpholinyl)ethoxy]phenyl}-N-phenyl-1H-imidazo[4,5-b]pyridin-7-amine
6-chloro-N-(3-ethylphenyl)-2-{4-[2-(4-morpholinyl)ethoxy]phenyl}-1H-imidazo[4,5-b]pyridin-7-amine
2-[benzyl(6-chloro-2-{4-[2-(4-morpholinyl)ethoxy]phenyl}-1H-imidazo[4,5-b]pyridin-7-yl)amino]ethanol
2-[(6-chloro-2-{4-[2-(4-morpholinyl)ethoxy]phenyl}-1H-imidazo[4,5-b]pyridin-7-yl)amino]ethanol
N-benzyl-6-chloro-N-methyl-2-{4-[2-(4-morpholinyl)ethoxy]phenyl}-1H-imidazo[4,5-b]pyridin-7-amine
6-chloro-N-methyl-2-{4-[2-(4-morpholinyl)ethoxy]phenyl}-1H-imidazo[4,5-b]pyridin-7-amine
7-(benzylthio)-6-chloro-2-{4-[2-(4-morpholinyl)ethoxy]phenyl}-1H-imidazo[4,5-b]pyridine
6-chloro-N-[4-(methylsulfonyl)phenyl]-2-{4-[2-(4-morpholinyl)ethoxy]phenyl}-1H-imidazo[4,5-b]pyridin-7-amine
6-chloro-2-{4-[2-(4-morpholinyl)ethoxy]phenyl}-N-[4-(4-morpholinyl)phenyl]-1H-imidazo[4,5-b]pyridin-7-amine
N'-(6-chloro-2-{4-[2-(4-morpholinyl)ethoxy]phenyl}-1H-imidazo[4,5-b]pyridin-7-yl)-N,N-diethyl-1,4-benzenediamine
N-{4-[(6-chloro-2-{4-[2-(4-morpholinyl)ethoxy]phenyl}-1H-imidazo[4,5-b]pyridin-7-yl)amino]phenyl}acetamide
6-chloro-2-{4-[2-(4-morpholinyl)ethoxy]phenyl}-7-phenoxy-1H-imidazo[4,5-b]pyridine
6-chloro-2-{4-[2-(4-morpholinyl)ethoxy]phenyl}-7-[2-(1-pyrrolidinyl)ethoxy]-1H-imidazo[4,5-b]pyridine
6-chloro-2-[4-(2-morpholin-4-ylethoxy)phenyl]-N-(2-morpholin-4-ylethyl)-3H-imidazo[4,5-b]pyridin-7-amine
6-chloro-2-[4-(2-morpholin-4-ylethoxy)phenyl]-7-pyrrolidin-1-yl-3H-imidazo[4,5-b]pyridine
6-chloro-2-[4-(2-morpholin-4-ylethoxy)phenyl]-N-(1-phenylethyl)-3H-imidazo[4,5-b]pyridin-7-amine
6-chloro-7-(4-methylphenyl)-2-[4-(2-morpholin-4-ylethoxy)phenyl]-3H-imidazo[4,5-b]pyridine
6-chloro-7-(3-methoxyphenyl)-2-[4-(2-morpholin-4-ylethoxy)phenyl]-3H-imidazo[4,5-b]pyridine
N-(3-{6-chloro-2-[4-(2-morpholin-4-ylethoxy)phenyl]-3H-imidazo[4,5-b]pyridin-7-yl}phenyl)acetamide
6-chloro-2-[4-(2-morpholin-4-ylethoxy)phenyl]-7-thien-3-yl-3H-imidazo[4,5-b]pyridine 2-[4-(2-morpholin-4-ylethoxy)phenyl]-3H-imidazo[4,5-b]pyridine-6,7-dicarbonitrile
7-chloro-2-[4-(2-morpholin-4-ylethoxy)phenyl]-3H-imidazo[4,5-b]pyridine-6-carbonitrile
7-anilino-2-(4-{2-[(2-methoxyethyl)(methyl)amino]ethoxy}phenyl)-3H-imidazo[4,5-b]pyridine-6-carbonitrile
6,7-dichloro-2-{4-[2-(4-morpholinyl)ethoxy]-3-nitrophenyl}-1H-imidazo[4,5-b]pyridine
5-(6,7-dichloro-1H-imidazo[4,5-b]pyridin-2-yl)-2-[2-(4-morpholinyl)ethoxy]aniline
2-amino-5-(6-chloro-7-methyl-3H-imidazo[4,5-b]pyridin-2-yl)phenol
5-(6-chloro-7-methyl-3H-imidazo[4,5-b]pyridin-2-yl)-2-{[(2R)-pyrrolidin-2-ylmethyl]amino}phenol
[5-(6-chloro-7-methyl-3H-imidazo[4,5-b]pyridin-2-yl)-2-(2-morpholin-4-ylethoxy)phenyl][(2R)-pyrrolidin-2-ylmethyl]amine
4-(6-chloro-7-methyl-3H-imidazo[4,5-b]pyridin-2-yl)-N'-(2-morpholin-4-ylethyl)benzene-1,2-diamine
[5-(6-chloro-7-methyl-3H-imidazo[4,5-b]pyridin-2-yl)-2-(4-methylpiperazin-1-yl)phenyl]amine
6,7-dichloro-2-[4-(4-morpholinyl)phenyl]-1H-imidazo[4,5-b]pyridine
[5-(6,7-dichloro-3H-imidazo[4,5-b]pyridin-2-yl)-2-morpholin-4-ylphenyl]amine
2-(4-aminophenyl)-6-chloro-N-phenyl-3H-imidazo[4,5-b]pyridine-7-amine
N-[4-(6,7-dichloro-3H-imidazo[4,5-b]pyridin-2-yl)phenyl]-N-(2-morpholin-4-ylethyl)amine
6-bromo-7-methyl-2-[4-(2-piperidin-1-ylethoxy)phenyl]-3H-imidazo[4,5-b]pyridine
6-bromo-7-methyl-2-(4-nitrophenyl)-1H-imidazo[4,5-b]pyridine
4-(6-bromo-7-methyl-1H-imidazo[4,5-b]pyridin-2-yl)aniline
N-[4-(6-bromo-7-methyl-1H-imidazo[4,5-b]pyridin-2-yl)phenyl]-3-cyanobenzenesulfonamide
N-[4-(6-bromo-7-methyl-1H-imidazo[4,5-b]pyridin-2-yl)phenyl]-4-cyanobenzenesulfonamide
N-[4-(6-bromo-7-methyl-1H-imidazo[4,5-b]pyridin-2-yl)phenyl]quinoline-8-sulfonamide
N-[4-(6-bromo-7-methyl-1H-imidazo[4,5-b]pyridin-2-yl)phenyl]-4-methoxybenzenesulfonamide
N-[4-(6-bromo-7-methyl-1H-imidazo[4,5-b]pyridin-2-yl)phenyl]-4-(2-cyanoethoxy)benzenesulfonamide
N-[4-(6-bromo-7-methyl-1H-imidazo[4,5-b]pyridin-2-yl)phenyl]-1-methyl-1H-imidazole-4-sulfonamide
N-[4-(6,7-dichloro-1H-imidazo[4,5-b]pyridin-2-yl)phenyl]-4-methoxybenzenesulfonamide
6-chloro-2-{4-[(2-morpholin-4-ylethyl)amino]phenyl}-N-phenyl-3H-imidazo[4,5-b]pyridine-7-amine
6-chloro-7-methoxy-2-[4-(2-morpholin-4-ylethoxy)phenyl]-3H-imidazo[4,5-b]pyridine
6-chloro-2-{4-[di(3-cyanobenzyl)amino]phenyl}-7-methoxy-1-yl-3H-imidazo[4,5-b]pyridine
3-({[4-(6-chloro-7-methoxy-1H-imidazo[4,5-b]pyridin-2-yl)phenyl]amino}methyl)benzonitrile)
N-[4-(6-chloro-7-methoxy-1H-imidazo[4,5-b]pyridin-2-yl)phenyl]-4-cyanobenzenesulfonamide
6-chloro-7-methoxy-2-[4-(2-piperidin-1-ylethoxy)phenyl]-3H-imidazo[4,5-b]pyridine
or a pharmaceutically acceptable salts thereof.

3. A pharmaceutical formulation comprising a therapeutically effective amount of a compound of formula (Id) according to claim 1, or a pharmaceutically acceptable salt thereof, in admixture with a pharmaceutically acceptable adjuvant, diluent or carrier.

4. A process for the preparation of a compound of formula (Id) according to claim 1 which comprises:
a) reaction of a compound of the general formula (II):

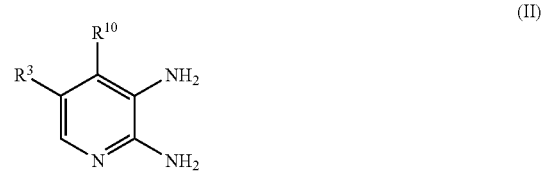

in which R³ and R¹⁰ are as defined in claim 1, with a compound of formula (III):

in which m, R¹ and Ar are as defined in claim 1, in the presence of an oxidizing agent to give a compound of formula (1d); or b) reaction of a compound of the general formula (II):

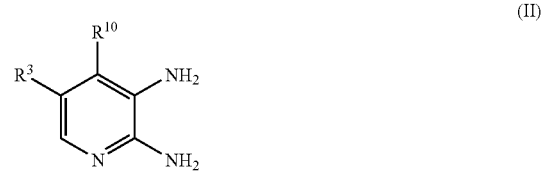

in which R³ and R¹⁰ are as defined in claim 1, with a compound of formula (IV):

in which m, R¹ and Ar are as defined in claim 1, in the presence of POCl₃ to give a compound of formula (1d); or c) reaction of a compound of formula (V):

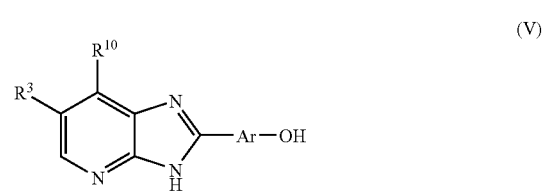

in which R³, R¹⁰ and Ar are as defined in claim 1; with a compound of formula (VI):

in which $R^2$ is as defined in claim 1 and LG represents a leaving group, to give a compound of formula (1 d) wherein m is 1 and $R^1$ is $OR^2$ in which $R^2$ is as defined in claim 1; or d) reaction of a compound of the general formula (VII):

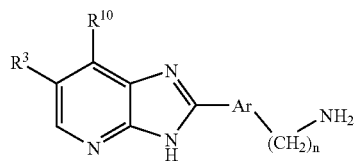
(VII)

in which n, $R^3$, $R^{10}$ and Ar are as defined in claim 1, with a compound of formula (VIII):

 (VIII)

in which $Ar^2$ is as defined in claim 1, to give a compound of formula (1 d) wherein m is 1 and $R^1$ is $(CH_2)_n NR^4 R^5$ in which $R^4$ is $CH_2 Ar^2$ and $R^5$ is H or $CH_2 Ar^2$ and $Ar^2$ is as defined in claim 1; or e) reaction of a compound of the general formula (IX):

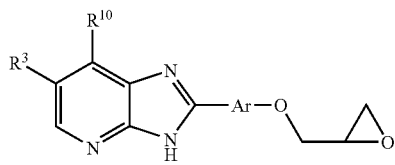
(IX)

in which $R^3$, $R^{10}$ and Ar are as defined in claim 1; with a compound of formula (X):

 (X)

in which $R^6$ and $R^7$ are as defined in claim 1, to give a compound of formula (1 d) wherein m is 1 and $R^1$ is $OR^2$ in which $R^2$ is $C_3$-alkyl being substituted by OH and $NR^6 R^7$ and where $R^6$ and $R^7$ are as defined in claim 1;

and where desired or necessary converting the resultant compound of formula (Id) or another salt thereof, into a pharmaceutically acceptable salt thereof or converting one compound of formula (Id) into another compound of formula (Id); and where desired converting the resultant compound of formula (Id) into an optical isomer thereof.

* * * * *